United States Patent [19]

Tomino et al.

[11] Patent Number: 5,192,799
[45] Date of Patent: Mar. 9, 1993

[54] COUMARAN GROUP CONTAINING AMINE COMPOUNDS AND THEIR ACID ADDITION SALTS AND QUATERNARY AMMONIUM SALTS AND THE USE THEREOF AS ANTI ARRHYTHMIC AGENTS AND AS PSYCHOTROPIC AGENTS

[75] Inventors: Ikuo Tomino, Ohtake; Masaharu Ishiguro, Ohtake; Takumi Kitahara, Ohtake; Keiichi Yokoyama, Iwakuni; Joji Kamiya, Mobara; Kanji Yoshihara, Mobara; Masaaki Ishii, Mobara; Akira Mizuchi, Mobara; Kazutoshi Horikomi, Mobara; Akira Awaya; Takuo Nakano, both of Yokohama, all of Japan

[73] Assignee: Mitsui Petrochemical Industries, Ltd., Tokyo, Japan

[21] Appl. No.: 895,417

[22] Filed: Jun. 5, 1992

Related U.S. Application Data

[63] Continuation of Ser. No. 780,546, Oct. 22, 1991, abandoned, which is a continuation of Ser. No. 392,964, Aug. 3, 1989, abandoned.

[30] Foreign Application Priority Data

Dec. 11, 1987 [JP] Japan .................... 62-312113
Dec. 14, 1987 [JP] Japan .................... 62-314234

[51] Int. Cl.$^5$ .................... C07D 307/80; C07D 307/83; A61K 31/34
[52] U.S. Cl. .................... 514/469; 514/470; 540/585; 540/596; 544/62; 544/153; 544/280; 544/360; 544/376; 546/19; 546/20; 546/148; 546/164; 546/192; 546/196; 546/200; 546/236; 546/237; 548/473; 548/476; 548/575; 548/314.7; 548/311.7; 548/311.4; 548/312.1; 549/33; 549/289; 549/398; 549/401; 549/440; 549/460; 549/462; 549/466; 549/471; 560/106; 560/142; 564/282; 564/287; 564/324; 564/353

[58] Field of Search .................... 549/462, 466; 514/469, 514/470

[56] References Cited

U.S. PATENT DOCUMENTS 3,853,923 12/1974 Ito et al. .................... 549/471

FOREIGN PATENT DOCUMENTS 2431491  3/1980 France .................... 514/469
0258174 12/1985 Japan .................... 549/462

OTHER PUBLICATIONS

The Merck Index, 11th ed., Budavari (ed), Merck and Co., Inc., p. 1035, No. 1032 (1989).
Chemical Abstracts: vol. 80, No. 108354 (1973); vol. 81, No. 58184b, (1974), vol. 92, No. 369b (1979); vol. 94, No. 57953h (1981); vol. 100, No. 203141c, (1983).

Primary Examiner—John M. Ford
Assistant Examiner—Philip I. Datlow
Attorney, Agent, or Firm—Sherman and Shalloway

[57] ABSTRACT

Amine represented by the following formula (1), or their acid addition salts or their quaternary ammonium salts.

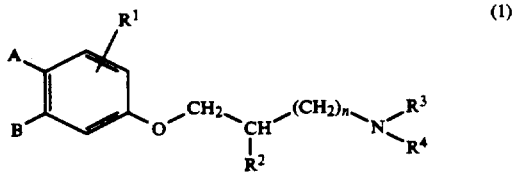

The amines of formula (1) or their pharmaceutically acceptable acid addition salts or quaternary ammonium salts are useful for the treatment and prevention of heart diseases of animals, particularly arrhythima, myocardial infarction, angina pectoris and heart failure and psychoneurological diseases.

16 Claims, No Drawings

COUMARAN GROUP CONTAINING AMINE COMPOUNDS AND THEIR ACID ADDITION SALTS AND QUATERNARY AMMONIUM SALTS AND THE USE THEREOF AS ANTI ARRHYTHMIC AGENTS AND AS PSYCHOTROPIC AGENTS

This application is a continuation of application Ser. No. 07/780,546, filed Oct. 22, 1991 now abandoned which is a continuation of Ser. No. 07/392,964, filed Aug. 3, 1989, now abandoned.

TECHNOLOGICAL FIELD

This invention relates to amines represented by general formula (1). More specifically, it relates to an amine represented by general formula (1) or its pharmaceutically acceptable acid addition salt or quaternary ammonium salt, and a drug containing it as an active ingredient, which is useful for the treatment and prevention of heart diseases of animals, particularly, arrhythmia, myocardial infarction, angina pectoris, heart failure and psychoneurological diseases of animals such as mania, depression, schizophrenia, delirium, dementia and anxiety.

BACKGROUND TECHNOLOGY

Disorder in the regularity of the systolic motion of the heart is called arrhythmia. Conditions of arrhythmia include one in which the cardiac output extremely decreases to induce ischemia in the whole body, one which invokes a danger of aggravating to serious arrhythmia, and one which has a strong subjective symptom. Treatment of arrhythmia is mainly by chemotherapy, and many anti-arrhythmic drugs have been clinically applied. Heretofore, the following proposals have been made with regard to anti-arrhythmic drugs.

Japanese Laid-Open Patent Publication No. 42815/1974 discloses a method of producing a compound having anti-arrhythmic activity which is represented by the formula

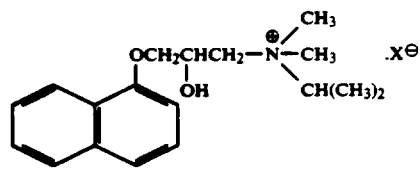

wherein X⁻ is an anion such as a halide, sulfate, methyl sulfate, alkylsulfonate (where the alkyl moiety has 1 to 4 carbon atoms), or ortho-, meta- or pyrro-phosphate ion, which comprises contacting a tertiary amine represented by the following formula

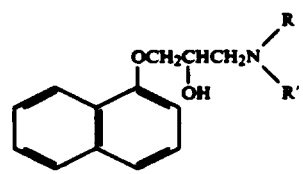

wherein R represents methyl and R' represents methyl or isopropyl, with a compound represented by (alkyl)X wherein one of the alkyl and R' is methyl and the other is isopropyl, and X is as defined.

Japanese Patent Publication No. 9952/1986 discloses a benzo(b)furan derivative represented by the following formula and its salt

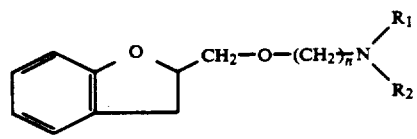

wherein $R_1$ and $R_2$, independently from each other, represent alkyl, or form a 4- to 8-membered saturated heterocycle which may contain an oxygen or nitrogen atom as a second hetero atom together with the nitrogen atom to which they are bonded, the nitrogen atom may be substituted by phenyl which may be substituted by halogen, trifluoromethyl, alkyl or alkoxy, and n is 2 or 3.

This patent document describes that the above compounds have anti-arrhythmic activity as well as analgesic activity.

Japanese Patent Publication No. 14538/1987 discloses the use of a quaternary ammonium salt of a phenylalkylamine represented by the following formula

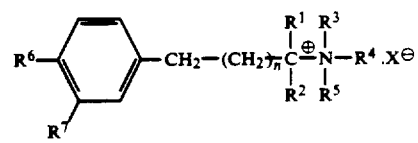

wherein n is 1 or 2; $R^1$ represents H or $C_1$-$C_2$ alkyl; $R^2$ represents H or $C_1$-$C_3$ alkyl; R represents $C_1$-$C_4$ alkyl or phenyl-$C_1$-$C_4$alkyl; $R^4$ represents $C_1$-$C_8$ alkyl; $R^5$ represents $C_1$-$C_{10}$ alkyl; $R^6$ and $R^7$, independently from each other, represent H, OH, halogen, $NO_2$, $C_1$-$C_3$ alkoxy or $C_1$-$C_3$ alkyl (with the proviso that at least one of $R^6$ and $R^7$ is H, and when n is 1 and both $R^6$ and $R^7$ are $NO_2$, $R^5$ is $C_6$-$C_{10}$alkyl); and X represents a phamaceutically acceptable anion,
as an anti-arrhythmic agent.

Japanese Laid-Open Patent Publication 252783/1987 discloses compounds of the following formula

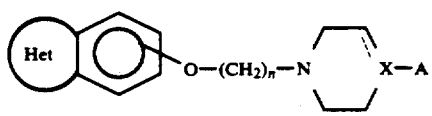

wherein
Het is selected from the following groups

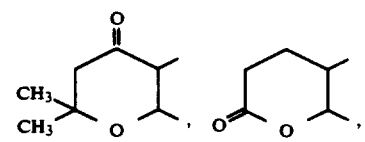

-continued

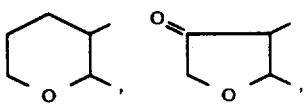

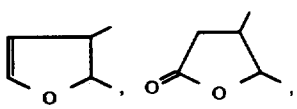

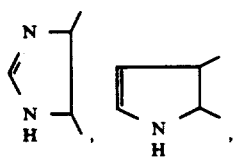

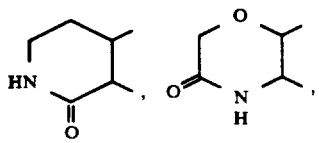

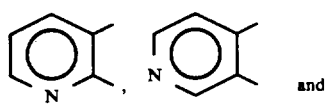

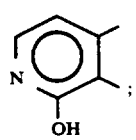

n is an integer of 2 to 5;
⸺ represents a single or double bond;
X represents C or N; and
A represents phenyl or phenyl substituted by lower alkyl, lower alkoxy, lower thioalkoxy, halogen or trifluoromethyl; 2-, 3- or 4-pyridinyl or 2-, 3- or 4-pyridinyl substituted by lower alkyl, lower alkoxy or halogen; 2-, 4- or 5-pyrimidinyl or 2-, 4- or 5-pyrimidinyl substituted by lower alkyl, lower alkoxy or halogen; 2-pyrazinyl or 2-pyrazinyl substituted by lower alkyl, lower alkoxy or halogen; 2- or 3-thienyl or 2- or 3-thienyl substituted by lower alkyl or halogen; 2- or 3-furanyl or 2- or 3-furanyl substituted by lower alkyl or halogen; or 2- or 5-thiazolyl or 2- or 5-thiazolyl substituted by lower alkyl or halogen,
or pharmaceutically acceptable acid addition salts thereof (excepting compounds of the above formula in which X is N, Het is

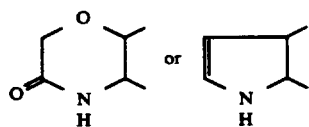 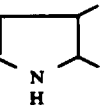

and A is phenyl or substituted phenyl). This patent document describes that these compounds have a pharmacological efficacy as antipsychotic agents.

Anti-arrhythmic agents are classified by the differences in their action on the potential difference between the inside and outside of the myocardial cell membrane, which differences occur when the antiarrhythmic agents bind to various ion channels of the myocardial cell membrane to change ion's permeability to these channels. Vaughan Williams classified antiarrhythmic agents as classes I, II, III and IV on the basis of their electrophysiological characteristics, and this classification has generally been used.

A series of changes in membrane potential which occur when a myocardial cell in a stationary state is stimulated and gets excited and returns to the stationary state are called action potential, and the time required from the occurrence of the action potential until the stationary state is restored is known as action potential duration (APD for short).

The cardiac muscles cannot be re-excited immediately after, or during, the occurrence of an action potential. This is called refractoriness, and the time during which even a great stimulation cannot induce excitation is called the effective refractory period, or ERP. This refractory period has closely to do with the duration of the action potential.

Anti-arrhythmic agents belonging to class I are a sodium channel blocker, and are sub-classified into Ia, Ib and Ic by the mechanism of their action on APD and ERP. Ia denotes a drug which prolongs APD and ERP and includes, for example, quinidine, procainamide and disopyramide. Ib is a drug which shortens APD and ERP and includes, for example, lidocaine and mexiletine. Ic is a drug which maintains APD and ERP unchangeable, and includes, for example, flecainide.

Anti-arrhythmic agents belonging to class II are sympathiotonia inhibitors which correspond to many beta-blockers. Anti-arrhythmic agents of class III are drugs which markedly prolong APD and ERP, and include, for example, amiodarone, bretylium, and sotalol, but have not yet been marketed in Japan. Anti-arrhythmic agents belonging to class IV are calcium channel blockers and include, for example, verapamil, diltiazem and nicardipine.

The excitation of the heart is successively transmitted through a stimulation transmitting system ranging from the stinoatrial node to the Purkinje fiber, and contracts the atrium and ventricle. Swinging of the excitation transmission as a result of the stimulation transmitting system getting out of order is called reentry. If the excitation swinging ends through one turn, extrasystole occurs, and if it continues, tachycardia occurs. If reentry occurs here and there simultaneously, flutter and fibrillation result.

It is suggested that drugs which markedly prolong APD and ERP can inhibit or prevent such ventricular extrasystole, tachycardia, ventricular fibrillation, etc. Annual Reports in Medicinal Chemistry, H. J. Hess ed., Academic Press, New York, N.Y.; see General Review of J. Thomis et al. in Vol. 18, Chapter 11 (1983).]

The anti-arrhythmic agents of class III correspond to these drugs, and are useful for treating and preventing ventricular arrhythmia which are serious or on which the other class of drugs are ineffective, but the research and development of these drugs fall behind the research and development of the anti-arrhythmic agents of classes I, II and IV, particularly class I.

Clofilium [Japanese Laid-Open Patent Publication No. 95520/1979, Japanese Patent Publication No. 14538/1987, U.S. patent application Ser. No. 861789 (1977) now abandoned, European Patent Application No. 2604 (1979), melperone, meobentine, pirmentol, and the above-mentioned amiodarone, bretylium, and sotalol are among known anti-arrhythmic agents of class III. Some of them have strong class I activity, and it is only the last three compounds which are actually applied clinically. The reason which can be cited is that many of these drugs have strong toxicity and poor transport to tissues and concurrently inhibit the function of the heart in effective concentrations, and may induce undesirable central nervous side-effects. Furthermore, these compounds are not orally administrable because of their properties, and this prevents their clinical application. The aforesaid drugs now clinically applied more or less entail the above various problems.

On the other hand, psychotic diseases such as mania, depression, schizophrenia, delirium, dementia and anxiety are widely treated by chemotherapy using various psychotropic drugs. It is expected to develop drugs having higher safety and duration and being easier to use, or psychotropic drugs having a new action mechanism, a broad action spectrum and a novel chemical structure.

It is an object of this invention to provide novel amines, acid addition salts and quaternary ammonium salts thereof.

Another object of this invention is to provide a novel and useful class III anti-arrhythmic agents comprising the above compounds of this invention which have very favorable biological activity, prolong APD and ERP markedly and exhibit anti-arrhythmic activity in various arrhythmic models.

Still another object of this invention is to provide novel and useful drugs for central nervous system and pyschotropic drugs, such as anti-depressants, antianxiety agents, sedatives and anti-dementia agents.

Further objects of the invention along with its advantages will become apparent from the following description.

DISCLOSURE OF THE INVENTION

According to this invention, the above objects and advantages of the invention are achieved by amines of the following formula (1), acid addition salts thereof or quaternary ammonium salts thereof,

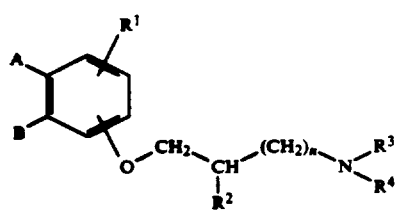

(1)

wherein

A and B, taken together, represent a group selected from groups of the following formulae (a) to (q)

$-CO-CR^5R^6-O-$ (a)

$-CO-CR^7R^8-CR^9R^{10}-$ (b)

$-CR^{11}=CR^{12}-O-$ (c)

$-CR^{13}R^{14}-CR^{15}R^{16}-O-$ (d)

$-CH(OH)-CR^{17}R^{18}-O-$ (e)

$-CH(OH)-CR^{19}R^{20}-CR^{21}R^{22}-$ (f)

$-CR^{23}R^{24}-CR^{25}=CR^{26}-O-$ (g)

$-O-CO-CR^{27}=CR^{28}-$ (h)

$-O-CR^{32}R^{33}-O-$ (j)

$-(CR^{34}R^{35})_m-$ (k)

$-CO-CR^{36}R^{37}-CR^{38}R^{39}-O-$ (l)

$-O-CO-CR^{40}R^{41}-CR^{42}R^{43}-$ (m)

$-CR^{44}R^{45}-CR^{46}R^{47}-CR^{48}R^{49}-O-$ (n)

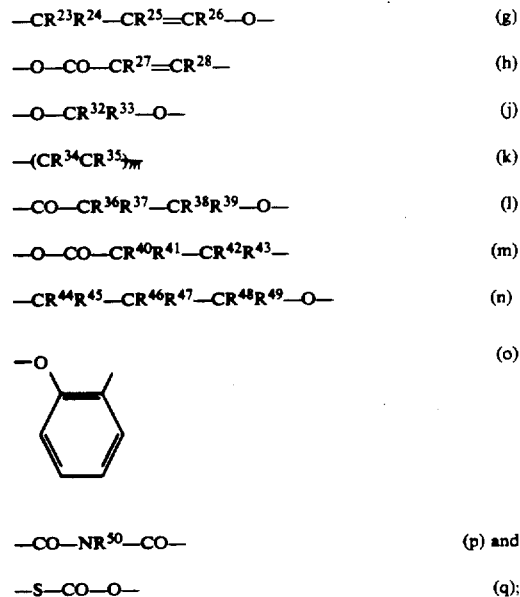

(o)

$-CO-NR^{50}-CO-$ (p) and $-S-CO-O-$ (q);

or A represents a group selected from the class consisting of lower alkenyl, lower acyl, lower acylvinyl and alpha,alpha-di-lower alkylbenzyl, and B is hydrogen, lower acyloxy, lower alkoxy or benzoyloxy;

$R^1$ is hydrogen, lower alkyl, lower alkoxy, halogen, amino, nitro or lower alkylsulfamoyl;

$R^2$ is hydrogen, hydroxyl or lower alkyl;

$R^3$ is hydrogen, alkyl, lower alkoxy-lower alkyl, lower alkoxy-lower alkoxy-lower alkyl, lower alkoxycarbonyl-lower alkyl, lower acyl-lower alkyl, ethylenedioxy lower alkyl, lower alkenyl, lower alkynyl, cycloalkyl, phenyl, benzyl, $$-\underset{\underset{SR^{51}}{|}}{C}=N-CN,$$

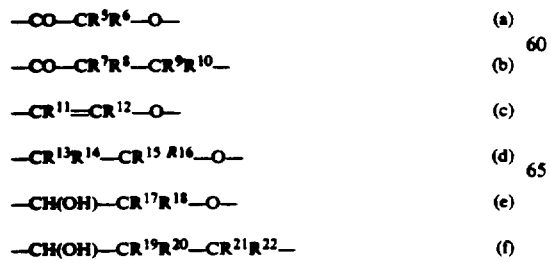

$R^4$ is alkyl, lower alkenyl, lower alkynyl, lower alkoxy-lower alkyl, hydroxyalkyl, cycloalkyl, benzyl, phenethyl, cyclohexyloxy, 2-bicyclo[2.2.1]heptanyl, adamantyl, piperidino which may be substituted, or 2-tetrahydrofuranylmethyl, or $R^3$ and $R^4$, taken together with the nitrogen atom to which they are bonded may form a 4- to 8-membered ring represented by the following formula

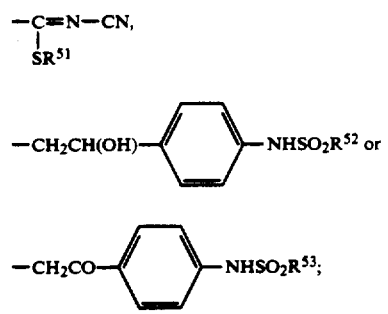

$R^5$–$R^{10}$, $R^{13}$–$R^{27}$, $R^{29}$–$R^{32}$ and $R^{34}$–$R^{49}$ are identical or different, and each represents hydrogen or lower alkyl;

$R^{11}$ is hydrogen, hydroxyl, lower alkoxy, lower acyloxy or lower alkyl;

$R^{12}$ is hydrogen, lower alkyl, lower acyl or benzoyl;

$R^{28}$ and $R^{50}$ are identical or different and each represents hydrogen, phenyl or lower alkyl;

$R^{33}$ is hydrogen, lower alkyl or lower alkoxy;

$R^{51}$–$R^{53}$ are identical or different and each represents lower alkyl;

X and Y are identical or different and each represents lower alkylene;

Z is methylene, imino, oxygen or sulfur;

$R^{05}$ and $R^{06}$ are substituents on X, Y or Z, and, independently from each other, represent hydrogen, lower alkyl, hydroxy-lower alkyl, lower alkoxy, cyclohexyl, hydroxyl, carboxyl, carbamoyl, lower alkoxycarbonyl, lower alkylsulfonamide, di-lower alkylcarbamoyl, lower alkylamide, aryl which may be substituted, benzyl which may be substituted, benzoyl which may be substituted, or heteroaryl which may be substituted, or $R^{05}$ and $R^{06}$, bonded to each other, may form oxo (=O), lower alkylene, ethylenedioxy or —CONHCH$_2$N(C$_6$H$_5$)—, or when they are present on adjacent carbon atoms, they may form a benzene ring together with the carbon atoms;

n is a number of 0, 1, 2, 3 or 4; and m is 3 or 4 (the plurality of $R^{34}$ and $R^{35}$ groups may be identical or different); provided that when $R^3$ and $R^4$ form the above 4- to 8-membered ring together with the nitrogen atom to which they are bonded, A and B together represent a group of formula (a), (c), (h) or (p), or A is lower acyl and B is lower alkoxy, or A and B together represent the group of formula (a), and when $R^3$ and $R^4$ form a 6-membered ring together with the nitrogen atom to which they are bonded, it is not a 6-membered ring in which the fourth position counted from the nitrogen atom bonded to –(CH$_2$)$_n$ as the first position is lower alkylimino, phenylimino, 2-pyridinylimino, lower alkylmethylene or benzyl. Compounds represented by formula (1) can be divided, for the sake of convenience, into two groups of compounds represented by the following formulae (1)-1 and (1)-2.

Formula (1)-1

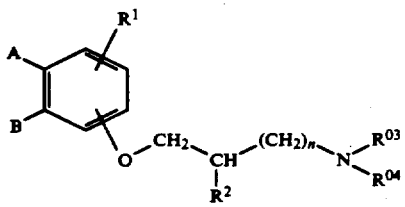
(1)-1 wherein

A, B, $R^1$, $R^2$ and n are the same as defined in formula (1);

$R^{03}$ is hydrogen, alkyl, lower alkoxy-lower alkyl, lower alkoxy-lower alkoxy-lower alkyl, lower alkoxycarbonyl-lower alkyl, lower acyl-lower alkyl, ethylenedioxy-lower alkyl, lower alkenyl, lower alkynyl, cyloalkyl, phenyl, benzyl,

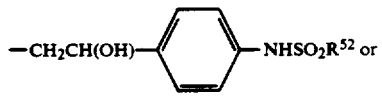

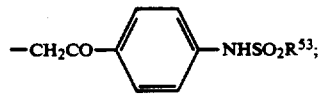

$R^{04}$ is alkyl, lower alkenyl, lower alkynyl, lower alkoxy-lower alkyl, hydroxyalkyl, cycloalkyl, benzyl, phenethyl, cyclohexyloxy, 2-bicyclo[2.2.1-]heptanyl, adamantyl, piperidino which may be substituted, or 2-tetrahydrofuranylmethyl; and, $R^{51}$, $R^{52}$ and $R^{53}$ are as defined as in formula (1);

and acid addition salts or quaternary ammonium salts thereof.

Formula (1)-2

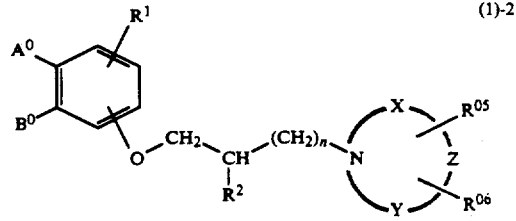
(1)-2 wherein $A^0$ and $B^0$, independently from each other, represents the group (a), (c), (h) or (p) in formula (1), or $A^0$ is lower acyl and $B^0$ is lower alkoxy;

$R^1$, $R^2$, n, $R^{05}$, $R^{06}$, X, Y and Z are as defined in formula (1);

provided that when $A^0$ and $B^0$ together represent the group (a) and the ring formed by N, X, Y and Z is a 6-membered ring, it is not a 6-membered ring in which the fourth position counted from the nitrogen atom bonded to —CH$_2$—$_n$ as the first position is lower alkylimino, phenylimino, 2-pyridinylimino, lower alkylmethylene or benzyl;

and acid addition salts or quaternary ammonium salts

In formulae 1) and (1)-1 above, A and B, taken together, may represent a group selected from the class consisting of groups of formulae (a) to (q) above.

The left-side portion of the formulae (1) and (1)-1

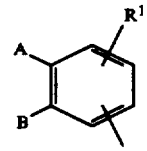

shows the following portions when A and B ar groups (a) (q).

When A and B represent the group (a),

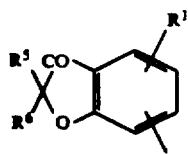

When A and B represent the group (b),

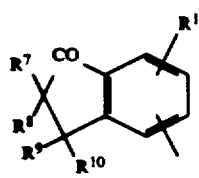

When A and B represent the group (c),

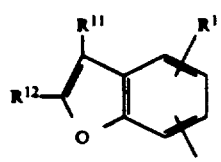

When A and B represent the group (d),

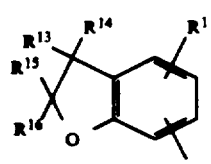

When A and B represent the group (e),

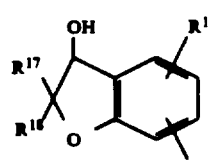

When A and B represent the group (f),

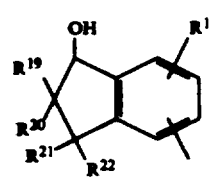

When A and B represent the group (g),

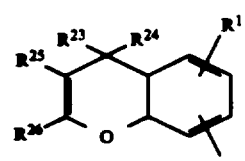

When A and B represent the group (h),

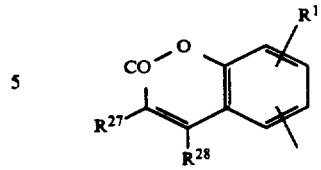

When A and B represent the group (j),

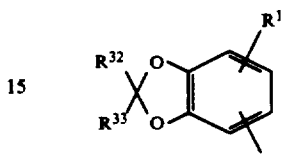

When A and B represent the group (k),

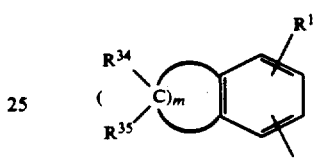

When A and B represent the group (l),

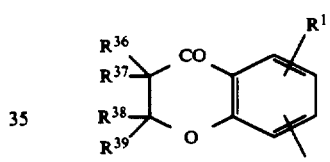

When A and B represent the group (m),

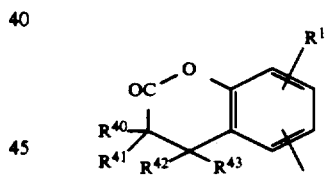

When A and B represent the group (n),

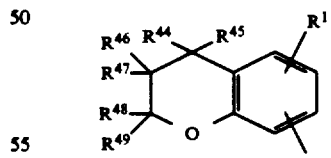

When A and B represent the group (o),

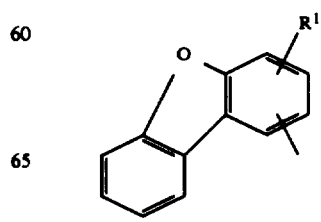

When A and B represent the group (p),

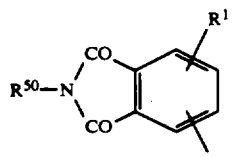

When A and B represent the group (q),

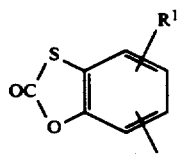

Furthermore, in formulae (1) and (1)-1, A may be a group selected from lower alkenyl, lower acyl, lower acylvinyl and alpha,alpha-di-lower alkylbenzyl and B, hydrogen, lower acyloxy or benzoyl. The right-side portion in formulae (1) and (1)-1, for example, the following portion in formula (1)

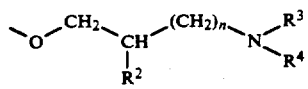

is desirably bonded to the benzene ring to which A and B are bonded in such a manner that it is para to A or B.

For example, when A and B are bonded to form the group (a), the formula (1) is preferably expressed as

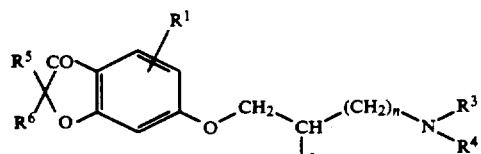

or

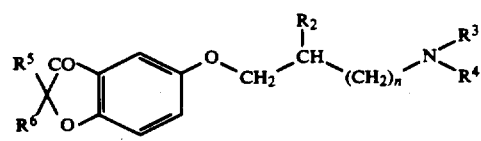

Likewise, when A and B are bonded to form the group (m), the formula (1) is preferably expressed as

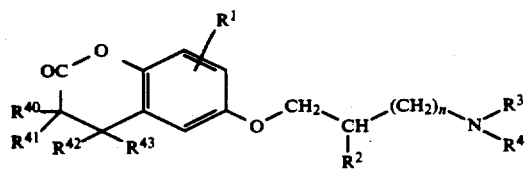

or

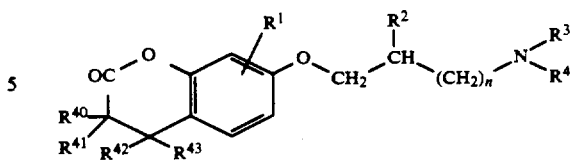

In formulae (1 and (1)-1, the lower alkenyl which A can represent preferably has 2 to 4 carbon atoms. Examples of the lower alkenyl are vinyl, propenyl, allyl and butenyl.

The lower acyl preferably has 2 to 4 carbon atoms. Examples are acetyl, propionyl and butyryl.

The lower acylvinyl is preferably one in which the lower acyl moiety has 2 to 4 carbon atoms. Examples include acetylvinyl, propionylvinyl and butyrylvinyl.

The alpha,alpha-di-lower alkylbenzyl is preferably one in which the lower alkyl moiety has 1 to 3 carbon atoms. The two lower alkyl groups may be identical or different. Examples of the alpha,alpha-di-lower alkylbenzyl include alpha,alpha-dimethylbenzyl, alpha,alpha-diethylbenzyl, alpha,alpha-dipropylbenzyl and alpha,alpha-methylethylbenzyl. B in formulae (1) and (1)-1 is hydrogen, lower acyloxy, lower alkoxy or benzoyloxy.

The lower acyloxy preferably has 2 to 4 carbon atoms. Examples include acetyloxy, propionyloxy and butyryloxy.

Examples of the lower alkoxy may be the same as the examples of $R^1$ given below. Preferably, it is methoxy.

In formulae (1) and (1)-1, $R^1$ represents hydrogen, lower alkyl, lower alkoxy, halogen, amino, nitro or lower alkylsulfamoyl. The lower alkyl preferably has 1 to 4 carbon atoms, and may be linear or branched. Examples of the lower alkyl are methyl, ethyl, n-propyl, iso-propyl, n-butyl, sec-butyl, iso-butyl, and t-butyl.

The lower alkoxy preferably has 1 to 4 carbon atoms, and may be linear or branched.

Examples of preferred halogen atoms are fluorine, chlorine, bromine and iodine.

The lower alkylsulfamoyl preferably has 1 to 4 carbon atoms in the lower alkyl moiety. The lower alkyl moiety is linear or branched.

$R^2$ is hydrogen, hydroxyl or lower alkyl. Examples of the lower alkyl may be the same as those given above with regard to $R^1$.

$R^3$ in formula (1) and in formula (1)-1 are hydrogen, alkyl, lower alkoxy-lower alkyl, lower alkoxy-lower alkoxy lower alkyl, lower alkoxycarbonyl-lower alkyl, lower acyl-lower alkyl, ethylenedioxy-lower alkyl, lower alkenyl, lower alkynyl, cycloalkyl, phenyl, benzyl,

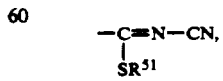

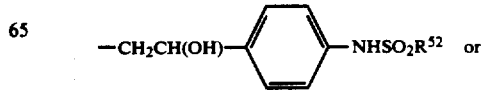

-continued

The alkyl may be a linear or branched alkyl group having 1 to 10 carbon atoms. Besides the lower alkyl exemplified as $R^1$, n-pentyl, iso-pentyl, n-hexyl, n-heptyl, n-octyl, n-nonyl and n-decyl may be cited as examples.

The lower alkoxy-lower alkyl preferably has 1 to 3 carbon atoms in the alkoxy moiety and the alkyl moiety. Examples of the alkoxy moiety are methoxy, ethoxy and propoxy, and examples of the alkyl moiety are methyl, ethyl, n-propyl, and iso-propyl.

The lower alkoxy-lower alkoxy-lower alkyl preferably has 1 to 3 carbon atoms in each alkoxy moiety and the alkyl moiety. Examples of the alkoxy moiety and the alkyl moiety are the same as those given above.

The lower alkoxycarbonyl-lower alkyl preferably has 1 to 3 carbon atoms in the lower alkoxy moiety and the lower alkyl moiety. Examples of these are the same as those given above.

The lower acyl-lower alkyl preferably has 2 to 4 carbon atoms in the lower acyl moiety and 1 to 3 carbon atoms in the lower alkyl moiety. Examples of this group may be the same as given above.

The ethylenedioxy-lower alkyl preferably has 2 to 3 carbon atoms in the lower alkyl moiety. Examples are beta-(ethylenedioxy)ethyl, gamma-(ethylenedioxy)ethyl and gamma-(ethylenedioxy)propyl.

Examples of the lower alkenyl may be the same as those given above with regard to A.

The lower alkynyl preferably has 2 to 4 carbon atoms, and includes, for example, ethynyl, propargyl and butynyl.

The cycloalkyl preferably has 5 to 7 carbon atoms, and examples may be cyclopentyl, cyclohexyl and cyclobutyl.

The lower alkyl represented by $R^{51}$ in

$R^{52}$ in 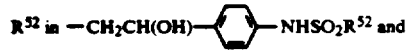 and $R^{53}$ in 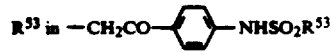

preferably has 1 to 3 carbon atoms. Its examples are the same as those given above.

$R^4$ in formula (1) and $R^{04}$ in formula (1)-1 is alkyl, lower alkenyl, lower alkynyl, lower alkoxy-lower alkyl, hydroxyalkyl, cycloalkyl, benzyl, phenethyl, cyclohexyloxy, 2-bicyclo[2.2.1]heptanyl, adamantyl, piperidino which may be substituted, or 2-tetrahydrofuranylmethyl.

Examples of the alkyl, lower alkenyl, lower alkynyl and cycloalkyl may be the same as those given above with regard to $R^3$.

The hydroxyalkyl preferably has 2 to 7 carbon atoms, and examples include hydroxyethyl, hydroxypropyl, hydroxybutyl, hydroxypentyl, hydroxyhexyl and hydroxyheptyl.

The substituent on the piperidino group may be, for example, methyl or ethyl.

In formulae (1) and (1)-1, $R^5$ through $R^{32}$ and $R^{34}$ through $R^{49}$ are identical or different, and each represents hydrogen or lower alkyl. Examples of the lower alkyl may be the same as those given above for $R^1$.

$R^{33}$ is hydrogen, lower alkyl or lower alkoxy. Examples of the lower alkyl and lower alkoxy may be the same as those given above with regard to $R^1$.

$R^{50}$ is hydrogen, phenyl or lower alkyl. Examples of the lower alkyl may be the same as those given above with regard to $R^1$.

$R^1$ and $R^2$ in formula (1)-2 may be same as those given above with regard to formulae (1) and (1)-1.

Groups $A^0$ and $B^0$ are either group (a), group (h) or group (p) described with regard to A and B. Alternatively, $A^0$ is lower acyl and $B^0$ is lower alkoxy. The lower acyl preferably has 2 to 4 carbon atoms, and the lower alkoxy preferably has 1 to 3 carbon atoms. Examples of these may be the same as those given above.

In formulae (1) and (1)-2, X and Y, independently from each other, represent lower alkylene. The lower alkylene preferably has 1 to 5 carbon atoms and includes, for example, methylene, dimethylene, trimethylene, tetramethylene and pentamethylene.

In formulae (1) and 1)-2, Z is methylene, amino, oxygen or sulfur.

In formulae (1) and (1)-2, and are each a substituent on X, Y or Z, and independently from each other, represent hydrogen, lower alkyl, hydroxy-lower alkyl, lower alkoxy, cyclohexyl, hydroxyl, carboxyl, carbamoyl, lower alkoxycarbonyl, lower alkylsulfonamide, di-lower alkylcarbamoyl, lower alkylamide, aryl which may be substituted, benzyl which may be substituted, benzoyl which may be substituted, or heteroaryl which may be substituted.

Examples of the lower alkyl and lower alkoxy may be the same as those given above with regard to $R^1$.

The hydroxy-lower alkyl preferably has 1 to 4 carbon atoms, and includes, for example, hydroxymethyl and hydroxyethyl.

The lower alkoxycarbonyl preferably has 1 to 3 carbon atoms in the lower alkoxy moiety, and includes, for example, methoxycarbonyl and ethoxycarbonyl.

The lower alkylsulfonamide preferably has 1 to 3 carbon atoms in the lower alkyl moiety, and includes, for example, methylsulfonamide and ethylsulfonamide.

The di-lower alkylcarbamoyl preferably has 1 to 3 carbon atoms in the lower alkyl moiety. The two lower alkyl groups may be identical or different. Examples of the di-lower alkylcarbamoyl are dimethylcarbamoyl, diethylcarbamoyl and methylethylcarbamoyl.

The lower alkylamide preferably has 1 to 3 carbon atoms, and examples include methylamide, ethylamide and n-propylamide.

The aryl which may be substituted may preferably be, for example, phenyl which may be substituted by lower alkoxy, halogen, nitro, amino, hydroxy, or acetamide.

The benzyl which may be substituted is, for example, benzyl which may be substituted by halogen, lower alkyl or lower alkoxy.

The benzoyl which may be substituted is, for example, benzoyl which may be substituted by halogen, lower alkyl or lower alkoxy.

Examples of the heteroaryl which may be substituted are furyl, pyrrolyl, thiophenyl, pyridyl, pyrimidyl, imidazolyl, thiazolyl, oxazolyl and piperidyl which may be substituted by lower alkyl, lower alkoxy or halogen.

$R^{05}$ and $R^{06}$ may be bonded to each other to form oxo (=O), lower alkylene, ethylenedioxy or —CONHCH$_2$N(C$_6$H$_5$)—, and when they are on adjacent carbon atoms, they may form a benzene ring together with the carbon atoms.

Examples of the lower alkylene may be the same as given above with regard to X.

In formulae (1) and (1)-2, the ring formed from N, X, Y and Z as ring members is a 4- to 8-membered ring, preferably a 5- to 7-membered ring. In the case of the 6-membered ring, it cannot be one in which the fourth position counted from the nitrogen atom bonded to —CH$_2$—$_n$ as the first position is lower alkylimino, phenylimino, 2-pyridinylimino, lower alkylmethylene or benzyl.

In formulae (1), (1)-1 and (1)-2, n is a number of 0, 1, 2, 3 or 4. In formulae (1) and (1)-1, m is a number of 3 or 4.

The following compounds may be cited as examples of the compounds of formula (1)-1 including formula (1)].

Compounds of formula (1)-1 represented by the following formulae

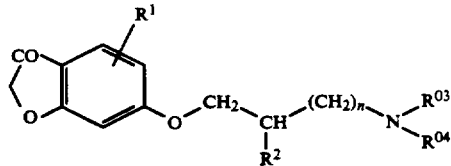

[corresponding to the case wherein A and B represent group (a)]:- In the following compounds exemplified, a moiety of the following structure is expressed by E for the sake of convenience.

   (100)

Hydrochloride of (100),   (102)

p-Toluenesulfonate of (100),   (104)

   (106)

p-Toluenesulfonate of (106),   (108)

   (110)

p-Toluenesulfonate of (110),   (112)

   (114)

Hydrochloride of (114),   (116)

E—CH$_2$—CH$_2$—NH-i-C$_4$H$_9$,   (118)

Hydrochloride of (118),   (120)

   (122)

Hydrochloride of (122),   (124)

   (126)

Hydrochloride of (126),   (128)

E—CH$_2$—CH$_2$—N(i-C$_4$H$_9$)$_2$,   (130)

Hydrochloride of (130),   (132)

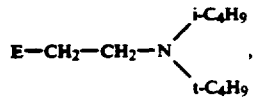                                                                                              (134)
Hydrochloride of (134),                                                                            (136)
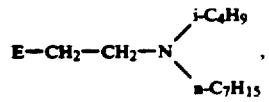                                                                                              (138)
Hydrochloride of (138),                                                                            (140)
E—CH₂—CH₂—N(n-C₄H₉)₂,                                                                (142)
p-Toluenesulfonate of (142),                                                                    (144)
E—CH₂—CH₂—N(CH₂—C≡CH)₂,                                                        (150)
Hydrochloride of (150),                                                                            (152)
E—CH₂—CH₂—N(CH₂—CH=CH₂)₂,                                                     (154)
Hydrochloride of (154),                                                                            (156)
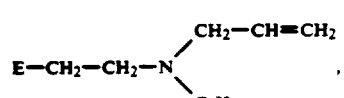                                                                                              (158)
Hydrochloride of (158),                                                                            (160)
E—CH₂—CH₂—N—(C₆H₁₁)₂,                                                                (162)
Hydrochloride of (162),                                                                            (164)
                                                                                                                   (166)
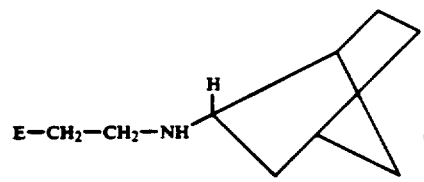
p-Toluenesulfonate of (166),                                                                    (168)
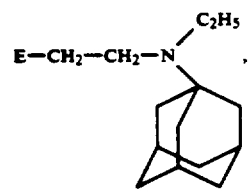                                                                                              (170)
Hydrochloride of (170),                                                                            (172)
E—CH₂—CH₂—N(CH₂C₆H₅)₂,                                                              (174)
Hydrochloride of (174),                                                                            (176)
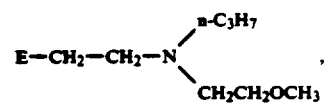                                                                                              (178)
Hydrochloride of (178),                                                                            (180)
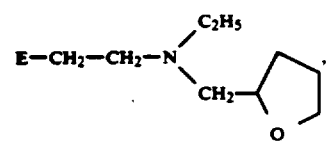                                                                                              (182)

-continued

| | |
|---|---|
| Hydrochloride of (182), | (184) |
| E—CH₂—CH₂—N(C₂H₅)(CH₂)₆OH | (186) |
| Hydrochloride of (186), | (188) |
| E—CH₂—CH₂—N(C₂H₅)—[2,2,6,6-tetramethylpiperidin-4-yl]NH, | (190) |
| p-Toluenesulfonate of (190), | (192) |
| E—CH₂—N(C₂H₅)(n-C₇H₁₅) | (194) |
| p-Toluenesulfonate of (194), | (196) |
| E—CH₂—N(C₂H₅)(n-C₉H₁₉) | (198) |
| p-Toluenesulfonate of (198), | (200) |
| E—CH₂—N(n-C₄H₉)₂, | (202) |
| p-Toluenesulfonate of (202), | (204) |
| E—CH₂—CH₂—N(C₂H₅)(n-C₅H₁₁) | (206) |
| p-Toluenesulfonate of (206), | (208) |
| E—CH₂—CH₂—N(C₂H₅)(n-C₇H₁₅) | (210) |
| p-Toluenesulfonate of (210), | (212) |
| E—CH(OH)—CH₂—N(C₂H₅)(n-C₇H₁₅) | (214) |
| p-Toluenesulfonate of (214), | (216) |
| E—CH(CH₃)—CH₂—N(C₂H₅)(n-C₇H₁₅) | (218) |
| p-Toluenesulfonate of (218), | (220) |
| [3-methyl-4-methylenedioxy-phenyl]—O—CH₂—CH₂—CH₂—N(C₂H₅)(n-C₇H₁₅) | (222) |
| Hydrochloride of (222), | (224) |

-continued
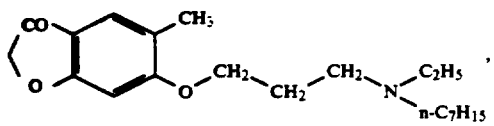 (226)
Hydrochloride of (226), (228)
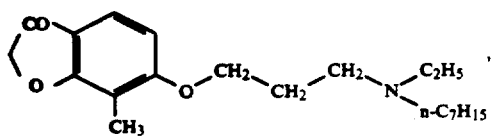 (230)
Hydrochloride of (230), (232)
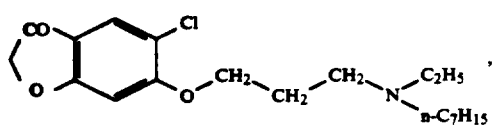 (234)
Hydrochloride of (234), (236)
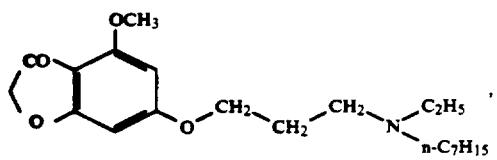 (238)
p-Toluenesulfonate of (238), (240)
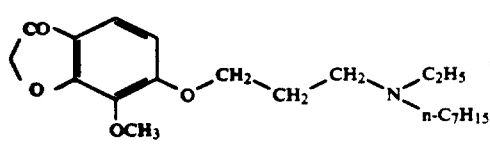 (242)
Hydrochloride of (242), (244)
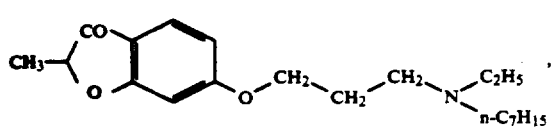 (246)
Hydrochloride of (246), (248)
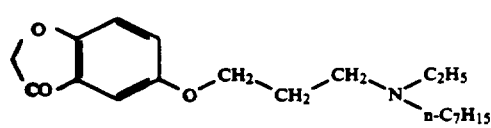 (250)
p-Toluenesulfonate of (250), (252)
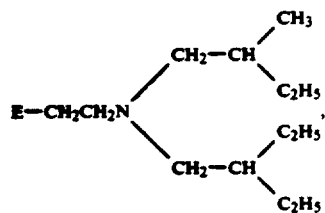 (253)
Hydrochloride of (254), (253)'
E—CH$_2$CH$_2$—NH-t-C$_4$H$_9$, (254)
Hydrochloride of (254), (254)'

-continued

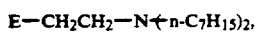 (255)

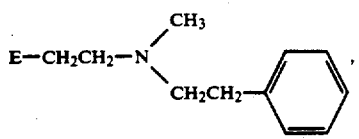 (256)

Hydrochloride of (256), (256)'

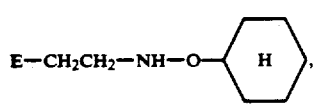 (257)

Hydrochloride of (257), (257)'

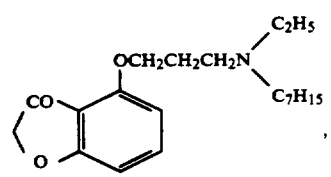 (258)

p-Toluenesulfonate of (258), (258)'

E—CH₂CH₂NH-isoC₃H₇, (259)

Hydrochloride of (259), (259)'

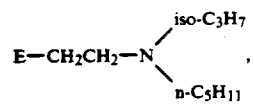 (260)

Hydrochloride of (260), (261)'

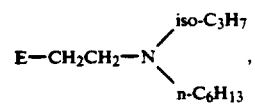 (261)

Hydrochloride of (261), (261)'

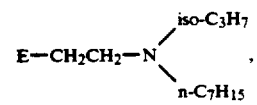 (262)

Hydrochloride of (262), (262)'

E—CH₂—NH-iso-C₃H₇, (263)

Hydrochloride of (263), (263)'

E—CH₂—NH(iso-C₃H₇)₂, (264)

Hydrochloride of (264), (264)'

E(CH₂)₇N(n-C₄H₉)₂, (265)

p-Toluenesulfonate of (265), (265)'

E(CH₂)₇N(n-C₄H₉)₂, (266)

p-Toluenesulfonate of (266), (266)'

E(CH₂)₇NHCH₃, (267)

E(CH₂)₇NHCH₃, (267)'

Hydrobromide of (267), (268)'

-continued
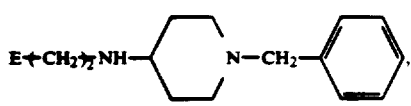  (268)
p-Toluenesulfonate of (268), (268)'
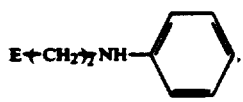  (269)
Hydrochloride of (269), (269)'
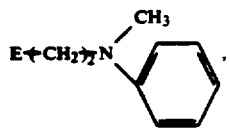  (270)
Hydrochloride of (270), (270)'
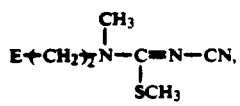  (271)
Hydrochloride of (271), (271)'
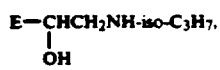  (272)
p-Toluenesulfonate of (272), (272)'
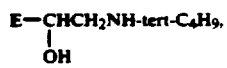  (273)
p-Toluenesulfonate of (273), (273)'
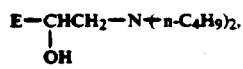  (274)
Hydrochloride of (274), (274)'
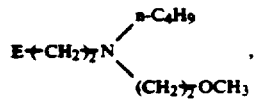  (275)
Hydrochloride of (275), (275)'
$E+CH_2\rightarrow_7 N+CH_2CH_2OCH_3)_2$, (276)
Hydrochloride of (276), (276)'
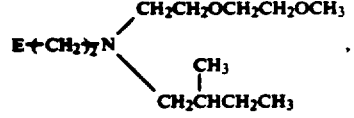  (277)
p-Toluenesulfonate of (277), (277)'
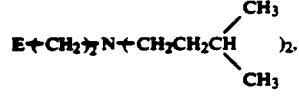  (278)
p-Toluenesulfonate of (278), (278)'

-continued

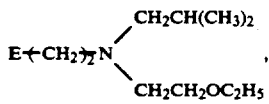 (279)

p-Toluenesulfonate of (279), (279)'

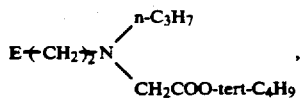 (280)

p-Toluenesulfonate of (280), (281)'

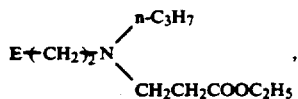 (281)

p-Toluenesulfonate of (281), (281)'

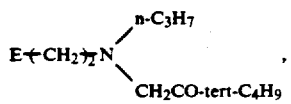 (282)

p-Toluenesulfonate of (282), (282)'

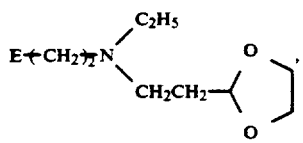 (283)

p-Toluenesulfonate of (283), (283)'

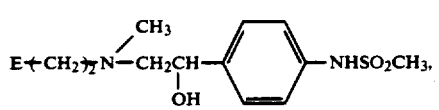 (284)

p-Toluenesulfonate of (284), (284)'

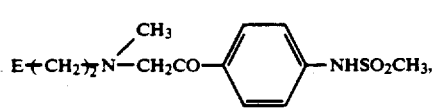 (285)

p-Toluenesulfonate of (285). (285)'

Compounds of formula (1)-1 [including formula (1)] in which A and B represent the group (b):

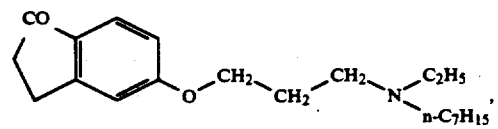 (300)

Hydrochloride of (300). (302)

Compounds of formula (1)-1 [including formula (1)] in which A and B represent the group (c):

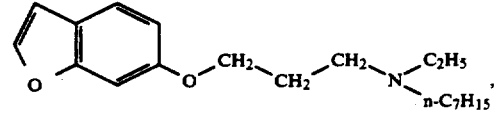 (350)

p-Toluenesulfonate of (350), (352)

-continued

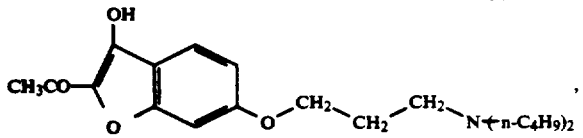 (354)

Hydrochloride of (354), (356)

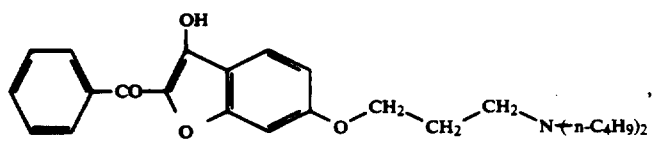 (358)

Hydrochloride of (358). (360)

Compounds of formula (1)-1 [including formula (1)]
in which A and B represent the group (d):

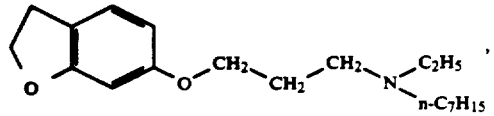 (400)

Hydrochloride of (400), (402)

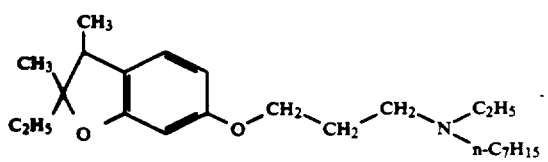 (404)

Compounds of formula (1)-1 [including formula (1)]
in which A and B represent the group (e):

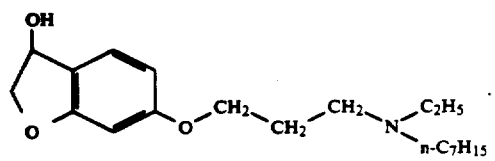 (450)

Compounds of formula (1)-1 [including formula (1)]
in which A and B represent the group (f):

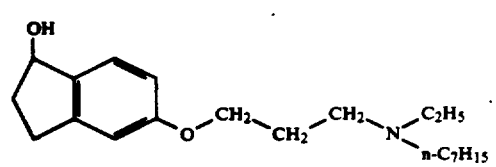 (500)

Compounds of formula (1)-1 [including formula (1)]
in which A and B represent the group (g):

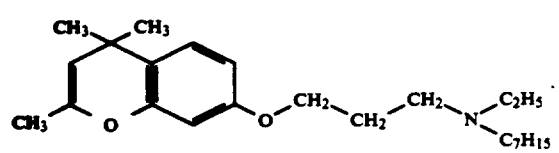 (550)

Compounds of formula (1)-1 [including formula (1)]
in which A and B represent the group (h):

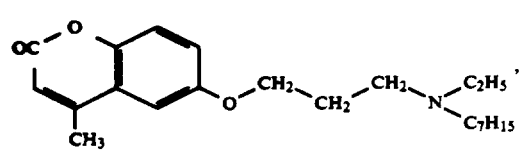 (600)

| | |
|---|---|
| Hydrochloride of (600), | (602) |
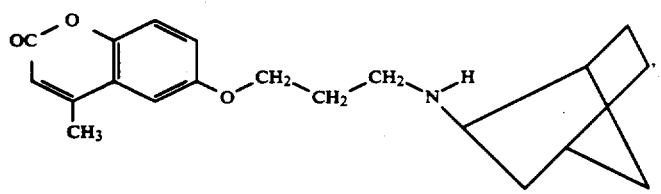 (604)
| | |
|---|---|
| Hydrochloride of (604), | (606) |
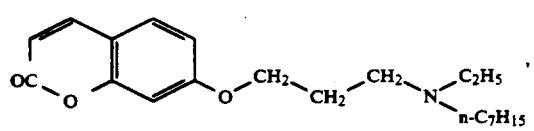 (608)
| | |
|---|---|
| Hydrochloride of (608), | (610) |
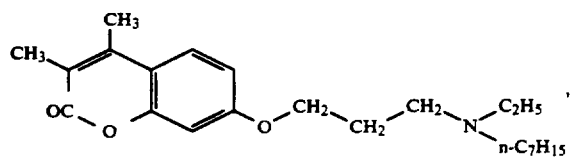 (612)
| | |
|---|---|
| Hydrochloride of (612), | (614) |
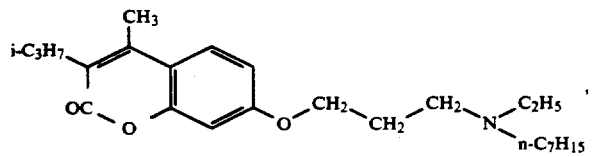 (616)
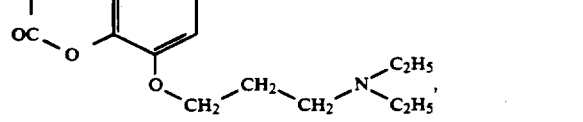 (618)
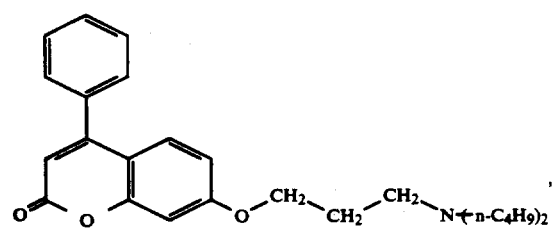 (616)
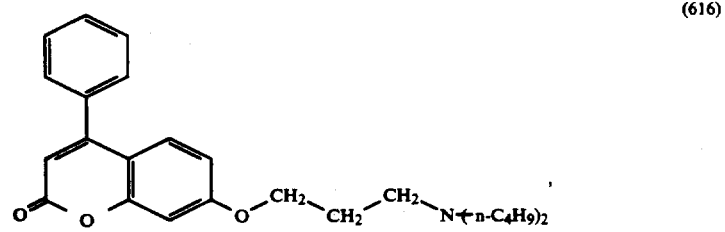
| | |
|---|---|
| Hydrochloride of (620). | (622) |
Compounds of formula (1)-1 [including formula (1)]
in which A and B represent the group (j):
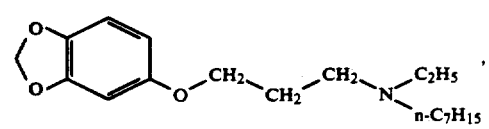 (700)
| | |
|---|---|
| Hydrochloride of (700), | (702) |

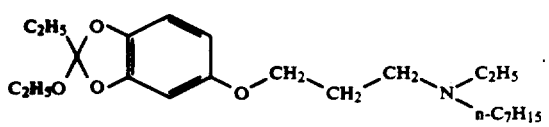
(704)

Compounds of formula (1)-1 [including formula (1)] in which A and B represent the group (k):

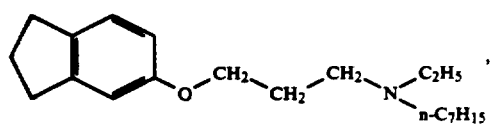
(750)

Hydrochloride of (750).
(752)

Compounds of formula (1)-1 [including formula (1)] in which A and B represent the group (l):

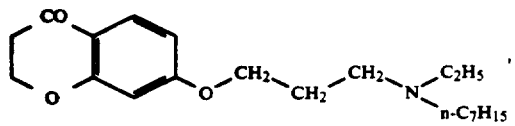
(800)

Hydrochloride of (800).
(802)

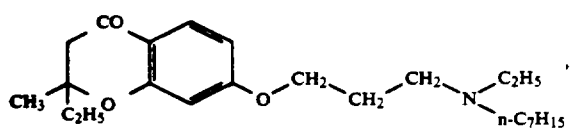
(804)

Hydrochloride of (804).
(806)

Compounds of formula (1)-1 [including formula (1)] in which A and B represent the group (m):

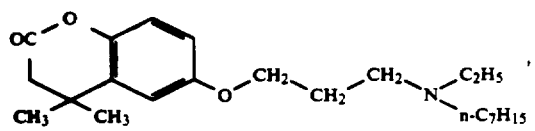
(850)

Hydrochloride of (850).
(852)

Compounds of formula (1)-1 [including formula (1)] in which A and B represent the group (n):

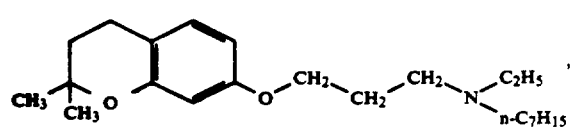
(900)

Hydrochloride of (900).
(902)

Compounds of formula (1)-1 [including formula (1)] in which A and B represent the group (o):

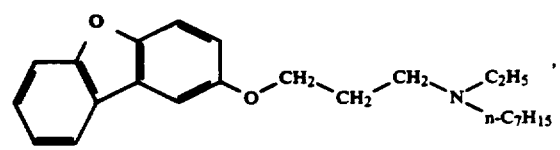
(930)

Hydrochloride of (930).
(932)

Compounds of formula (1)-1 [including formula (1)] in which A and B represent the group (p):

Hydrochloride of (940),  (941)

(942)

Hydrochloride of (942).  (943)

Compounds of formula (1)-1 [including formula (1)] in which A and B represent the group (q):

(950)

Hydrochloride of (950).  (952)

Examples of compounds of formula (1)-1 [including formula (1)] in which A and B are not directly bonded are as follows:-

(970)

(972)

(974)

Hydrochloride of (976),  (978)

p-Toluenesulfonate of (980),  (982)

(984)

p-Toluenesulfonate of (984).  (986)

Preferred as the quaternary ammonium salt of the compound of formula (1)-1 [including formula (1)] are compounds of the following formula (1)'-1 wherein A, B, $R^1$, $R^2$, $R^{03}$, $R^{04}$ and n are the same as defined in formula (1)-1; $R^{54}$ represents an alkyl group; and $X^\oplus$ represents a pharmaceutically acceptable one-equivalent anion.

Specific examples of $R^{54}$ may be the same as exemplified above with regard to $R^{03}$.

Examples of $X^\oplus$ are a chlorine ion, a bromine ion and an iodine ion.

Examples of the quaternary ammonium salt are given below.

(286)

-continued
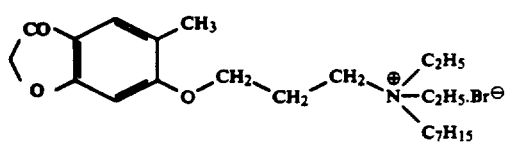  (287)
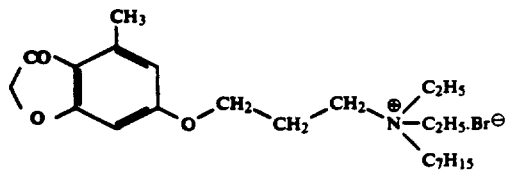  (288)
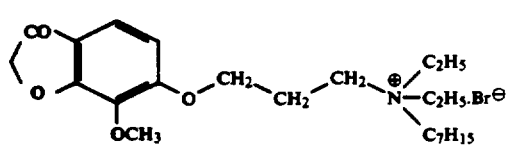  (289)
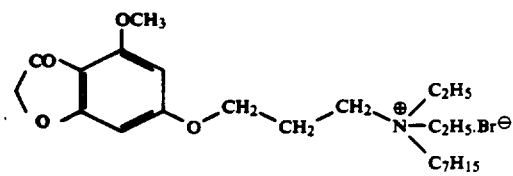  (290)
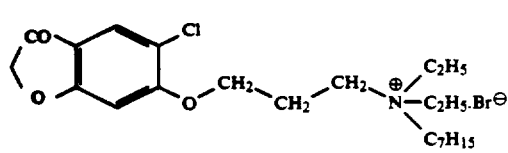  (291)
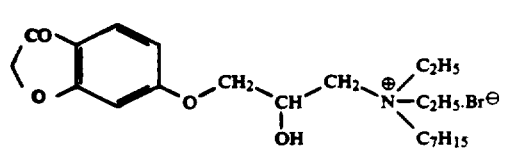  (292)
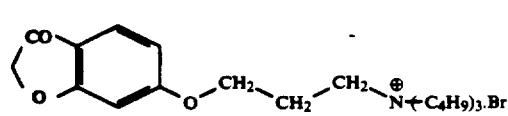  (293)
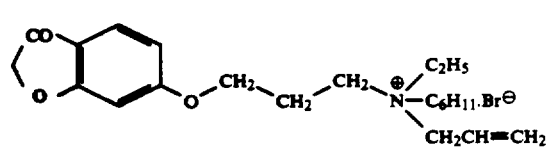  (294)
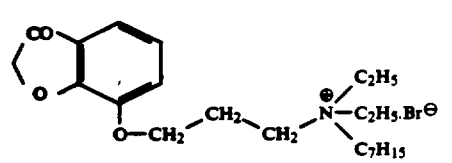  (295)
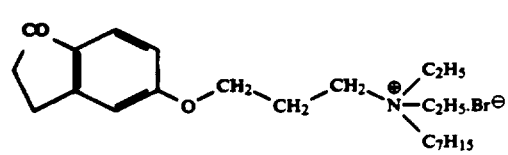  (320)

-continued
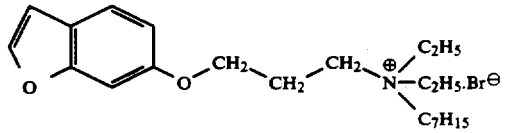 (370)
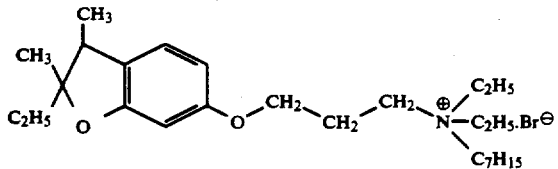 (420)
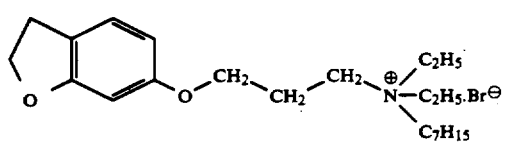 (422)
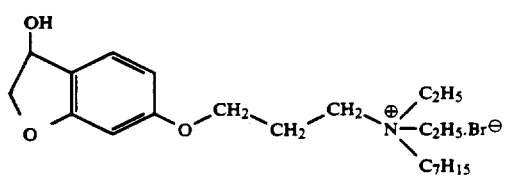 (470)
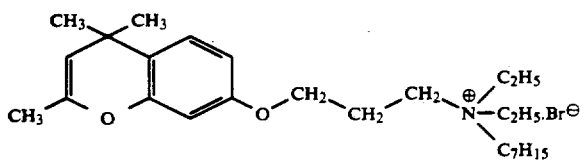 (570)
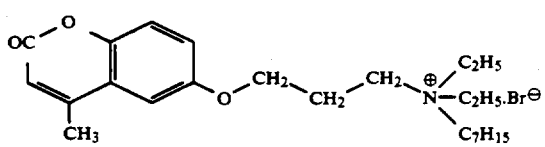 (630)
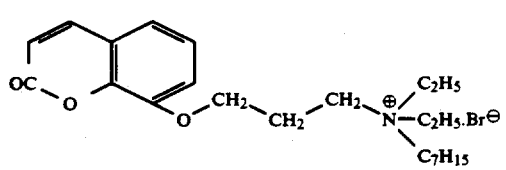 (632)
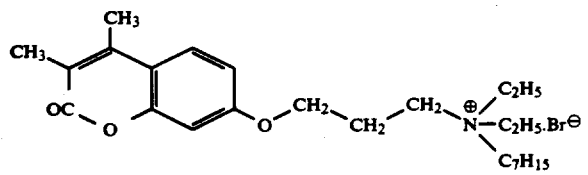 (634)
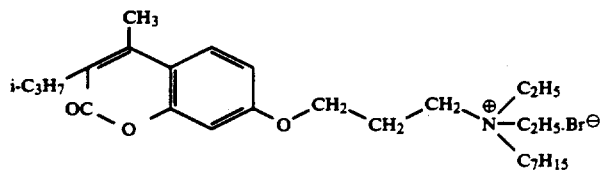 (636)

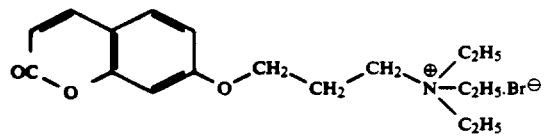
(638)
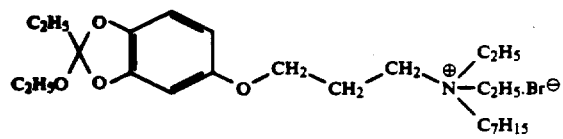
(720)
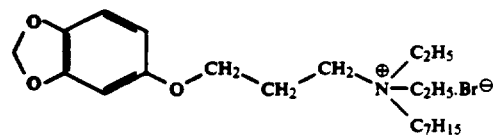
(722)
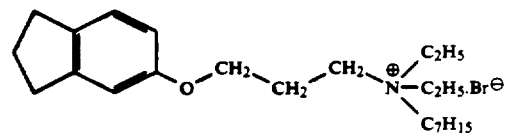
(770)
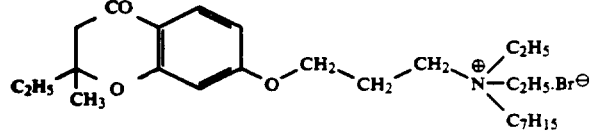
(820)
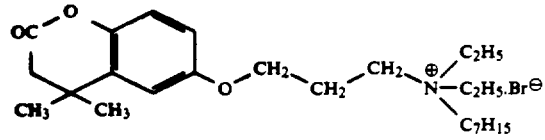
(870)
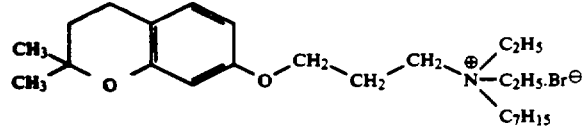
(920)
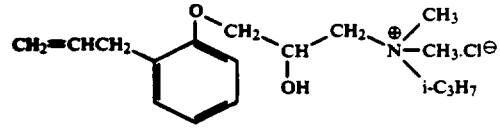
(1020)
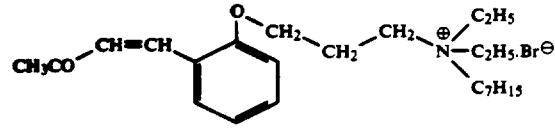
(1022)
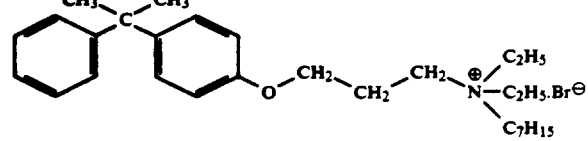
(1024)
Examples of the compounds of formula (1)-2 [including formula (1)], acid addition salts thereof and quaternary ammonium salts thereof are compounds of the following formulae. In compound (1104) and subsequent compounds, the moiety of the following structure is expressed as G.

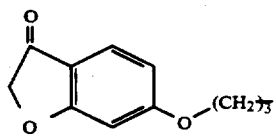
(1100)
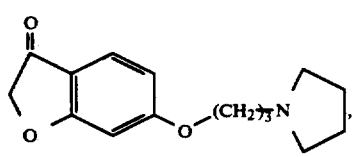
p-Toluenesulfonate of (1100), (1102)
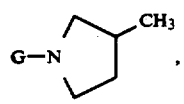 (1104)
Hydrochloride of (1104), (1106)
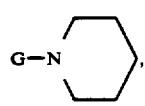 (1108)
Hydrochloride of (1108), (1110)
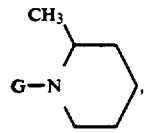 (1112)
Hydrochloride of (1112), (1114)
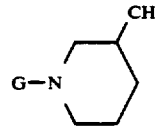 (1116)
Hydrochloride of (1116), (1118)
Quaternary ammonium salt of an ethyl bromide adduct of (1118), (1119)
Hydrochloride of 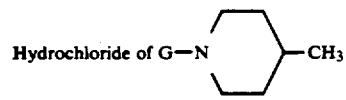 (1122)
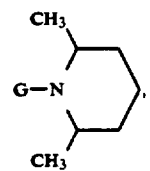 (1124)
Hydrochloride of (1124), (1126)
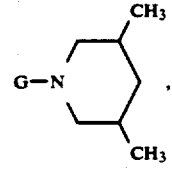 (1128)

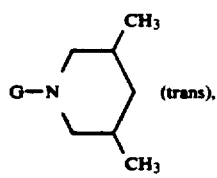 (1129)

Hydrochloride of (1128), (1130)

Hydrochloride of (1129), (1131)

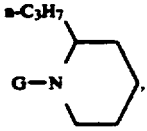 (1132)

Hydrochloride of (1132), (1134)

(1138)

Hydrochloride of 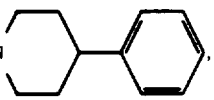, (1139)

p-Toluenesulfonate of G—N⟨piperidine⟩—⟨phenyl⟩, (1140)

Phosphate of G—N⟨piperidine⟩—⟨phenyl⟩, (1142)

Sulfate of G—N⟨piperidine⟩—⟨phenyl⟩,

Quaternary ammonium salt of an ethyl bromide adduct of (1143)

G—N⟨piperidine⟩—⟨phenyl⟩, (1144)

G—N⟨piperidine⟩—CH₂—⟨phenyl⟩,

Hydrochloride of (1144), (1146)

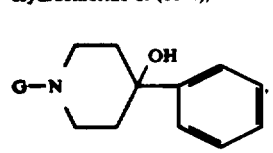 (1148)

Hydrochloride of (1148), (1150)

(1152)

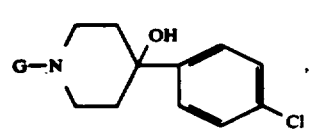

Hydrochloride of (1152), (1154)

-continued
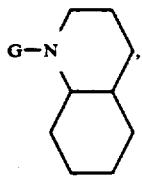 (1156)
Hydrochloride of (1156), (1158)
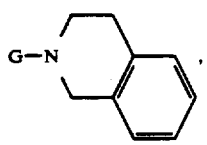 (1160)
Hydrochloride of (1160), (1162)
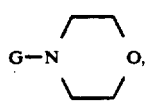 (1164)
p-Toluenesulfonate of (1164), (1166)
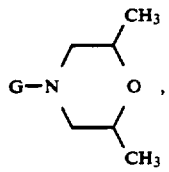 (1168)
p-Toluenesulfonate of (1168), (1170)
Quaternary ammonium salt of an ethyl bromide adduct of (1168), (1171)
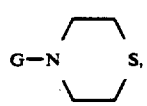 (1172)
p-Toluenesulfonate of (1172), (1174)
Quaternary ammonium salt of an ethyl bromide adduct of (1172), (1175)
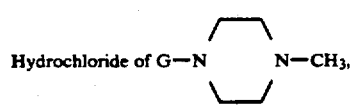 (1178)
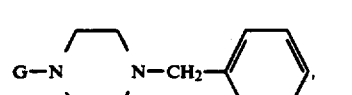 (1180)
Hydrochloride of (1180), (1182)
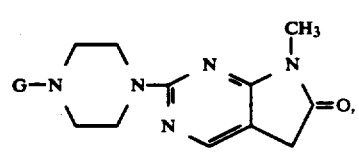 (1184)
Hydrochloride of (1184), (1186)

-continued
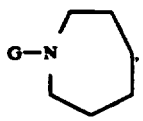  (1188)
p-Toluenesulfonate of (1188),  (1190)
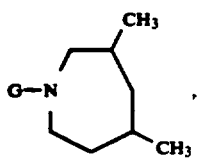  (1192)
Hydrochloride of (1192),  (1194)
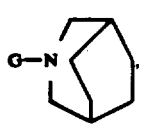  (1196)
Hydrochloride of (1196),  (1198)
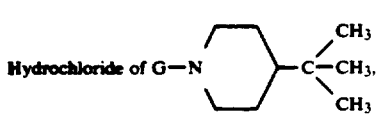  (1202)
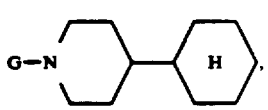  (1204)
Hydrochloride of compound No. (1204),  (1206)
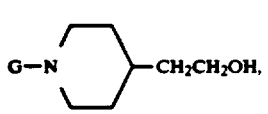  (1208)
Hydrochloride of compound No. (1208),  (1210)
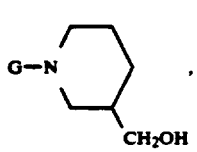  (1212)
Hydrochloride of compound No. (1212),  (1214)
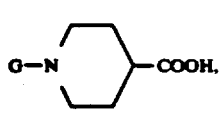  (1216)
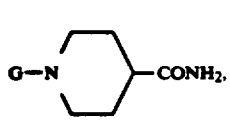  (1218)
Hydrochloride of compound No. (1218),  (1220)
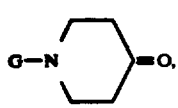  (1222)
Hydrochloride of compound No. (1222),  (1224)

-continued
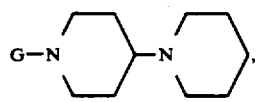 (1226)
Dihydrochloride of compound No. (1226), (1228)
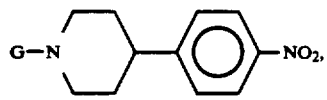 (1230)
Hydrochloride of compound No. (1230), (1232)
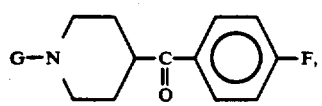 (1234)
Hydrochloride of compound No. (1234), (1236)
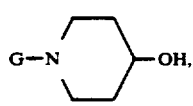 (1238)
Hydrochloride of compound No. (1238), (1240)
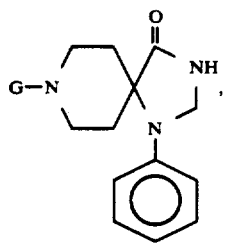 (1246)
Hydrochloride of compound No. (1246), (1248)
Hydrochloride of 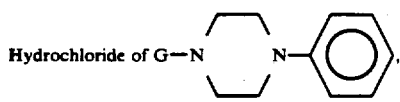 (1256)
Hydrochloride of 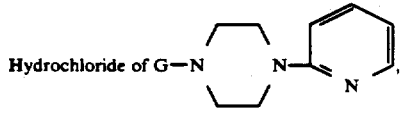 (1264)
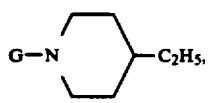 (1272)
Hydrochloride of (1272), (1274)
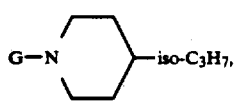 (1276)
Hydrochloride of (1276), (1278)
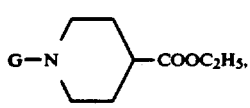 (1280)
Hydrochloride of (1280), (1282)

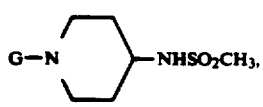 (1284)
Hydrochloride of (1284), (1286)
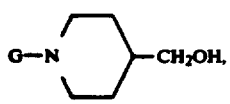 (1288)
Hydrochloride of (1288), (1290)
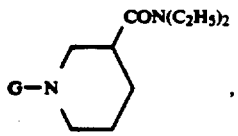 (1292)
p-Toluenesulfonate of (1292), (1294)
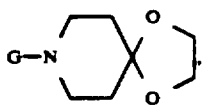 (1296)
p-Toluenesulfonate of (1296), (1298)
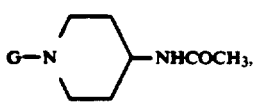 (1300)
Hydrochloride of (1300), (1302)
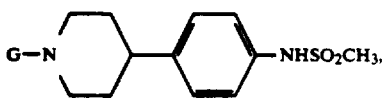 (1304)
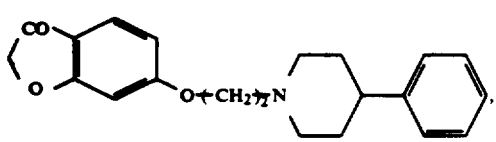 (1308)
Hydrochloride of (1308), (1310)
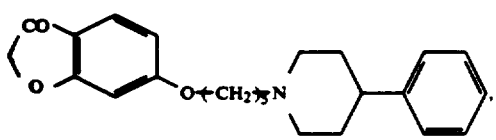 (1312)
p-Toluenesulfonate of (1312), (1314)
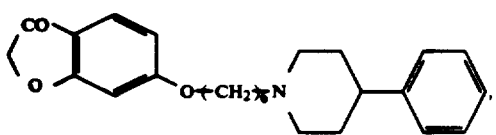 (1316)
p-Toluenesulfonate of (1316), (1318)

-continued
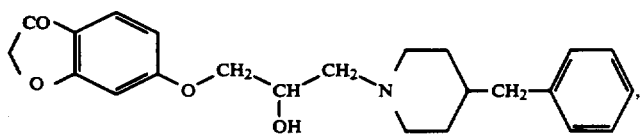 (1320)
Hydrochloride of (1320), (1322)
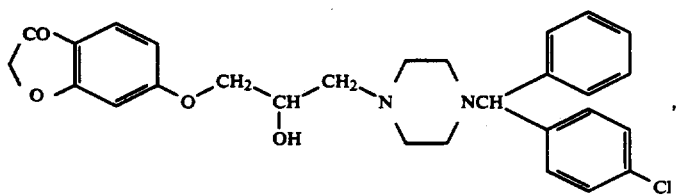 (1324)
Hydrochloride of (1324), (1326)
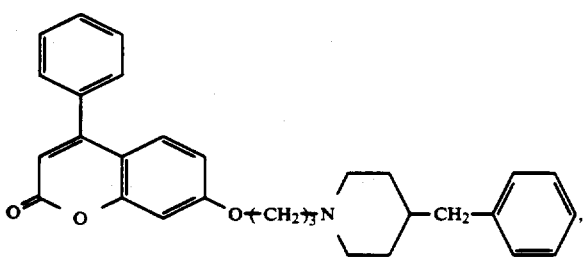 (1328)
Hydrochloride of (1328), (1330)
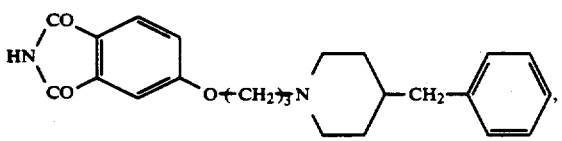 (1332)
Hydrochloride of (1332), (1334)
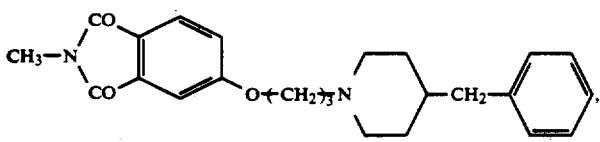 (1336)
Hydrochloride of (1336), (1338)
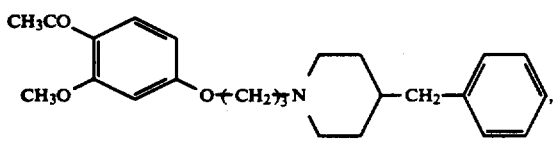 (1340)
Hydrochloride of (1340), (1342)
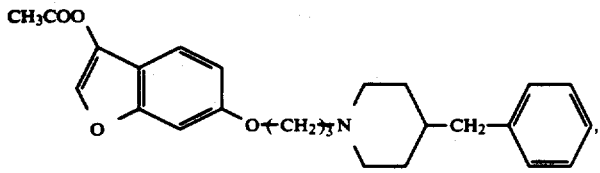 (1344)

The compounds of formula (1) can be produced by methods known per se.

For example, compounds of formula (1) in which A and B represent the group (a) can be produced by process (I), (II) or (III).

[Process I]

[Process II]

[Process III]

(X and Y, independently from each other, represent Cl, Br or I.)

(X = Cl or Br)

-continued

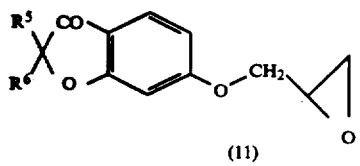

(11)

(11) + (6) ⟶

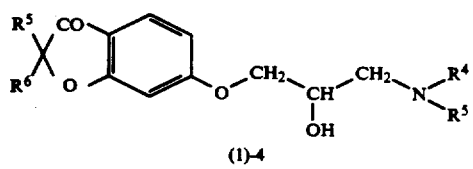

(1)-4

In process I, the reaction of compounds (2) and (3) may be carried out in accordance with the method of J. Am. Chem. Soc., 70, 3619 (1948). For example, compounds (2) and (3) are heated to a temperature of below about 30° C. in ether in the presence of $ZnCl_2$ while blowing HCl gas. Then, the reaction mixture is heated at the refluxing temperature in ethanol to form compound (4).

The reaction of compounds (5) and (6) is carried out at 40° to 120° C., preferably 60° to 100° C., for 1 to 20 hours, preferably 4 to 10 hours in the presence of an acid scavenger such as $K_2CO_3$ or $Na_2CO_3$ in a reaction medium, for example benzene, toluene, xylene, dimethylformamide, acetonitrile or ethyl acetate to form compound (7). The amounts of compounds (5) and (6) and the acid scavenger used are preferably nearly 1:1:1 by mole.

The reaction of compounds (4) and (7) is carried out in a reaction medium, for example benzene, toluene, xylene, acetonitrile, dimethylformamide or water, at room temperature, preferably 40° to 110° C. while using 1 to 2 equivalents, preferably 1 to 1.2 equivalents, each of compound (4) and the acid scavenger, per mole of compound (7). Thus, compound (1)-3 is formed.

In process II, the reaction of compounds (4) and (8) is carried out in the presence of an acid scavenger such as $K_2CO_3$ in a reaction medium, for example dimethylformamide, toluene or acetonitrile at a temperature of 40° to 100° C., preferably 60° to 80° C., for 1 to 10 hours, preferably 2 to 4 hours, to form compound (9).

The reaction of compound (9) with compound (6) is carried out in a reaction medium, for example dimethylformamide, acetonitrile or toluene at 40° to 100° C., preferably 60° to 80° C., for 4 to 60 hours, preferably 6 to 12 hours, to form compound (1)-3.

Process III is a process for producing compounds of formula (1) in which $R^2$ is hydroxyl.

The reaction of compounds (4) and (10) is carried out in a reaction medium such as acetonitrile or dimethylformamide at 40° to 100° C., preferably 60° to 80° C., for 1 to 8 hours, preferably 2 to 4 hours, to form compound (11).

The reaction of compound (11) with compound (6) is carried out in a reaction medium, for example acetonitrile or dimethylformamide, at 30° to 100° C., preferably 40° to 80° C., for 4 to 24 hours, preferably 6 to 15 hours, to form compound (1)-4.

Compounds of formula (1) in which A and B represent the other groups may also be produced by known reaction similar to the above-mentioned reactions.

These reactions are described in the following known publications.

J. Am. Chem. Soc., 94, 9166 (1972), J. Org. Chem. Soc., 26, 240 (1961), Angew. Chem. Int. Ed. Engl., 21, 247 (1982), and West German OLS No. 2550965.

The quaternary ammonium salts in this invention may also be produced by reactions known per se, for example the following reaction.

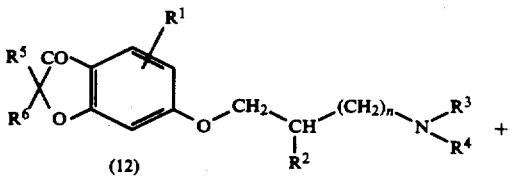

(12)

$R^{54}X \longrightarrow$ (13)

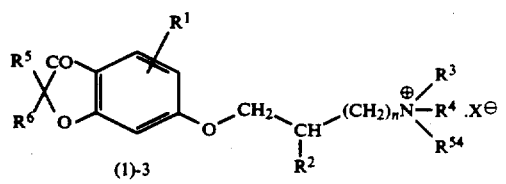

(1)-3

The reaction of compounds (12) and (13) is carried out in a reaction medium, for example acetonitrile, toluene, ethyl acetate or dimethylformamide at room temperature to 150° C., preferably 50° to 100° C., to form compound (1)-3.

The compounds of this invention represented by general formula (1) described above are valuable as anti-arrhythmic agents of class III having marked APD and ERP prolonging activity, and exhibit anti-arrhythmic activity in various arrhythmic models. Some of the compounds of general formula (I) also have the activity of suppressing the maximum rising speed (Vmax) of myocardial action potential, but the other compounds are pure class III anti-arrhythmic agents having no Vmax suppressing activity. Thus, the compounds of general formula (1) have valuable anti-arrhythmic activity and are used for the treatment and prevention of ischemic heart diseases, myocardial infarction, angina pectoris, cardiomyopathy, valvular disease of the heart, hypertensive heart disease and heart failure which induce, or possibly induce, arrhythmia.

Some of the compounds of this invention have hypotensive activity, beta-blocking activity, cardiotonic activity and pulse lowering activity and are expected to be applied to hypertension and heart failure.

Some of the compounds of this invention have anti-dopamine activity and anti-serotonin activity, and are used for the treatment and prevention of psychoneurologic diseases such as mania, depression, schizophrenia, delirium, dementia and anxiety as drugs for central nervous system and psychotropic drugs such as anti-depressants, anti-anxiety agents, sedatives and anti-dementia agents.

The compound of general formula (1) is used normally in the form of a pharmaceutical composition and administered to an animal through various routes such as oral, subcutaneous, intramuscular, intravenous, intraduodenum, intrarhinal, sublingual, skin permeating and intrarectal.

The present invention also provides a pharmaceutical preparation comprising a pharmaceutically acceptable carrier and as an active ingredient, the compound of general formula (1) or its pharmaceutically acceptable salt. The pharmaceutically acceptable salt includes, for example, acid addition salts.

Examples of the pharmaceutically acceptable salt of the compound of general formula (1) include salts formed from acids forming pharmaceutically acceptable nontoxic acid addition salts containing anions, such as hydrochloride, hydrobromides, sulfates, bisulfates, phosphates, acid phosphates, acetates, oxalates, maleates, fumarates, succinates, lactates, tartrates, benzoates, citrates, gluconates, saccharates, cyclohexylsulfamates, methanesulfonates, p-toluenesulfonates and naphthalenesulfonates.

Examples of the quaternary ammonium salt are salts formed between alkyl halides and the compounds of general formula (1).

The composition of this invention may be prepared in the form of a tablet, capsule, powder, granule, trouch, sublingual tablet, cachet wafer capsule, elixir, emulsion, solution, syrup, suspension, aerosol, ointment, eye drop, sterilized injectable solution, cataplasm, tape, soft or hard gelatin capsule, suppository, or sterile packed powder. Examples of the pharmaceutically acceptable carrier include lactose, glucose, sucrose, sorbitol, mannitol, corn starch, crystalline cellulose, gum arabic, calcium phosphate, crystalline cellulose, calcium phosphate, sodium alginate, calcium silicate, calcium sulfate, microcrystalline cellulose, polyvinyl pyrrolidone, tragacanth rubber, gelatin, syrup, methyl cellulose, carboxymethyl cellulose, sodium benzoate, methyl hydroxybenzoate, propyl hydroxybenzoate, talc, magnesium stearate, inert polymers, water, mineral oils, peanut oil acceptable for injection, and suppository bases such as glycerides.

The composition, whether solid or liquid, may contain a filler, a binder, a lubricant, a wetting agent, a disintegrant, an emulsifier, a suspending agent, a preservative, a sweetner or a flavor. The present composition may be prescribed such that after administration to a patient, the active component can be rapidly, continuously or delayed released.

In oral administration, the compound of general formula (1) is mixed with a carrier and a diluent, and formulated into the form of tablets, capsules, etc. In parenteral administration, the active ingredient is dissolved in 10 % aqueous glucose solution, isotonic aqueous salt solution, sterilized water or a similar liquid, and sealed up in a vial or ampoule for administration into the vein by drip infusion or injection, or into the muscles by injection. Advantageously, a dissolution aid, a local anesthetic, a preservative and a buffer may also be included in the medium. To enhance stability, the present composition can be lyophilized after it is filled into a vial or ampoule. In another case of parenteral administration, there is a preparation to be administered through the skin as an ointment or cataplasm. In this case, a molded cataplasma or a tape agent is advantageous.

The present composition contains 1 microgram to 1 g, generally 10 micrograms to 500 mg, of the active component per unit dosage form.

The composition of general formula (1) is effective over a wide dose range. For example, the dose per day usually falls within the range of 0.1 microgram/kg to 100 mg/kg. The amount of the compound to be actually administered is determined by a physician or veterinarian depending upon the age, body weight, response, symptom (for example in the case of arrhythmia, the type and strength of arrhythmia, and in the case of a central nervous disease, its symptom and history, etc.), and the administration route. Accordingly, the above range of the dose does not limit the scope of the invention. The suitable number of administrations per day is 1 to 6, usually 1 to 4.

The compound of general formula (1) is by itself an effective anti-arrhythmic agent, and is a therapeutic and prophylactic agent for ischemic heart diseases, myocardial infarction, angina pectoris and heart failure. As required, it may be administered in combination with one or several other equivalent drugs. Examples of the additional drugs include vasodilators such as dipyridamole, isosorbide dinitrate, molsidomine, trapidil, nicorandil, nitroglycerin, pentaerythritol tetranitrate, etafenone hydrochloride, oxyfedrine hydrochloride, trimetazidine hydrochloride, dilazep hydrochloride, carbocromene; calcium antagonists such as diltiazem hydrochloride, verapamil hydrochloride, nifedipine and nicardipine; cardiotonic agents such as digitoxin, digoxin, lanatoside, amrinone and milrinone; diuretics such as trichloromethiazide, hydrochlorothiazide, furosemide, bumetanide, mefruside, triamterene, clofenamide and spironolactone; hypotensive agents such as hydralazine hydrochloride, rauwolfia alkaloids, rescinnamine reserpine, dihydroergotoxin mesilate, prazosin hydrochloride, clonidine hydrochloride, Guanfacine hydrochloride, indapamide, labetalol, capropril, guanabenz acetate, tripamide, meticrane, methyldopa, guanethidine sulfate and betanidine sulfate; beta-blockers such as propranolol hydrochloride, pindolol and metoprolol tartrate; sympathomimetic agents such as ephedrine hydrochloride, etc. and the various antiarrhythmic agents described above.

The compound of general formula (1) is also itself an effective anti-psychotic agent, an antidepressant, an anti-anxiety agent, a sedative or an anti-dementia agent and is useful for treatment and prevention of psychoneurological diseases such as mania, depression, schizophrenia, delirium, dementia and anxiety. As required, it may be administered in combination with one or several other equivalent drugs. Examples of such additional drugs include psychotropic drugs such as haloperidol, butyrophenon, tiothixene, sulpiride, saltopride, zotepine, thioridazine hydrochloride, lithium carbonate, chloropromazine, fluphenazine hydrochloride, oxypertine, clotiapine, spiperone, chlorprothixene, timiperon, hydroxyzine hydrochloride, pimozide, bromperidol, perphenazine, carpiramine dimaleate, carpipramine hydrochloride, clocapramine dihydrochloride, imipramine, desipramine, amitriptyline, nortriptyline, amoxapine, doxepine, maprotiline, mianserin, nomifensine, viloxazine, L-5-HTP, pipamperone, etizolam, rofepramine, trimipramine, diazepam, medezepam, lorazepam, flutazolam, clotiazepam, bromazepam, mexazolam, chlordiazepoxide, cloxazolam, oxazolam, alprazolam, calcium hopantenate, lisuride, piracetam, aniracetam, $\gamma$-amino-$\beta$-hydroxybutyric acid, tymium, idebenone, tiapride, and bifemelane hydrochloride.

The following examples and experimental examples illustrate the formulation of the compound of general formula (1) and its biological activities. The present invention, however, is not limited to them. In the following examples of compositions, one of the compounds described in this invention, or another pharmaceutical compound encompassed within the general formula (1) are used as an active component. Examples and Referential Examples

REFERENTIAL EXAMPLE 1

Production of 6-hydroxycoumaran-3-one:-

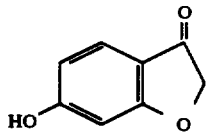

Hydrogen chloride gas was blown into a mixture of 150 g (1.36 moles) of resorcinol, 800 ml of dry ether, 100 g (1.32 moles) of chloroacetonitrile and 100 g (0.73 mole) of zinc chloride for about 2 hours. Crystals which precipitated were obtained by decantation. The crystals were washed with ether and 1500 ml of water was added. The mixture was refluxed for 1 hour and then cooled. The crystals were collected by filtration. Potassium acetate (130 g; 1.33 moles) and 850 ml of ethanol were added to the crystals, and the mixture was refluxed for 30 minutes. After cooling, 1500 ml of water was added, and the crystals were collected by filtration to give 107 g of the desired product (yield 54%).

Melting point: 240°–241° C.

$^1$H-NMR spectrum (DMSO-d$_6$-CDCl$_3$ solution, δppm): 4.60(3H, s), 6.50(1H, d, J=2 Hz), 6.63(1H, dd, J=2 and 9 Hz), and 7.44 (1H, d, J=9 Hz).

REFERENTIAL EXAMPLES 2 to 7

The compounds shown in Table 1 were obtained by operating as in Referential Example 1 except that 4-methylresorcinol, 5-methylresorcinol, 2-methoxyresorcinol, 2-methylresorcinol and 4-chlororesorcinol were used respectively instead of the resorcinol, and 2-chloropropionitrile was used instead of the chloroacetonitrile.

TABLE 1

| Referential Example No. | Compound | Yield | Melting point (°C.) | $^1$H-NMR spectrum (DMSO-d$_6$-CDCl$_3$ solution, δ ppm) |
|---|---|---|---|---|
| 2 | (structure with CH$_3$, OH) | 52 | 247–248 | 2.41 (3H, s), 4.57 (2H, s), 6.54 (1H, s), 7.28 (1H, s) |
| 3 | (structure with CH$_3$, OH) | 47 | 240–243 | * 2.52 (3H, s), 4.74 (2H, s), 6.42 (2H, s) |
| 4 | (structure with OH, OCH$_3$) | 40 | 161–163 | ** 3.90 (3H, s), 4.72 (2H, s), 6.66 (1H, d, J=9Hz), 7.20 (1H, d, J=9Hz) |
| 5 | (structure with OH, CH$_3$) | 40 | 213–214 | * 2.18 (3H, s), 4.82 (2H, s), 6.76 (1H, d, J=9Hz), 7.44 (1H, d, J=9Hz) |
| 6 | (structure with Cl, OH) | 7 | 230–231 | 4.74 (2H, s), 6.74 (1H, s), 7.58 (1H, s) |
| 7 | (structure with CH$_3$, OH) | 60 | 131–134 | 1.43 (3H, d, J=7Hz), 4.64 (1H, q, J=7Hz), 6.47 (1H, s), 6.56 (1H, dd, J=2 and 9Hz), 7.42 (1H, d, J=9Hz) |

*DMSO-d$_6$ solution
**CDCl$_3$ solution

REFERENTIAL EXAMPLE 8

Production of heptylacetamide

[CH₃(CH₂)₆NHCOCH₃]

Heptylamine (39 g; 0.34 mole was added dropwise to 46.6 g (0.59 mole) of pyridine and 43.4 g (0.43 mole) of acetic anhydride over 30 minutes, and the mixture was further stirred for 2 hours. After the reaction, the mixture was concentrated and extracted by adding water and ether. The ethereal layer was washed successively with a saturated aqueous solution of sodium hydrogen carbonate and then a saturated aqueous solution of sodium chloride, and then dried over anhydrous magnesium sulfate and concentrated to give 51 g of the desired compound yield 96 %).

¹H-NMR spectrum (CDCl₃ solution, ppm): 0.90(3H, t, J=7 Hz), 1.30(10H, m), 1.98 (3H, s), 3.24(2H, m).

In the same way as above, tetrahydrofurfuryl acetamide (yield 52%) was obtained by using tetrahydrofurfurylamine instead of the heptylamine.

¹H-NMR spectrum (CDCl₃ solution, δppm): 1.92(3H, m), 2.0(3H, s), 3.18(1H, m), 3.52–4.1(5H, m).

REFERENTIAL EXAMPLE 9

Production of 2-methoxyethylpropylamine (CH₃OCH₂CH₂NCH₂CH₂CH₃):-
     |
     H

A solution composed of 15 g (0.2 mole) of 2-methoxyethylamine and 12.3 g (0.1 mole) of propylbromide was stirred at room temperature for 2 hours. Ether was added and mixed with the resulting reaction mixture. The ethereal layer was removed, and the residue was extracted with water-methylene chloride. The methylene chloride layer was dried over anhydrous magnesium sulfate and concentrated to give 2.6 g (yield (22%) of the desired compound.

¹H-NMR spectrum CDCl₃ solution, δppm): 0.93(3H, t, J=7 Hz), 1.54(2H, m), 2.72(4H, m), 3.39(3H, s), 3.48(2H, m).

REFERENTIAL EXAMPLE 10

Production of ethylheptylamine
[CH₃CH₂NH(CH₂)₆CH₃]

Heptylacetamide 50 g; 0.32 mole) was added dropwise to a mixture of 500 ml of dry ether and 12.8 g (0.34 mole) of lithium aluminum hydride so that the mixture refluxed gently. After the addition, the refluxing was continued for another 10 hours. After cooling, 25 ml of water and 25 ml of 6N potassium hydroxide was added dropwise. The mixture was filtered and concentrated. Simple distillation of the resulting concentrate gave 30.5 g (yield 68%) of the desired product.

Boiling point: 41°–42° C./2 mmHg.

¹H-NMR spectrum CDCl₃ solution, δppm): 0.87(3H, t, J=7 Hz), 1.09(3H, t, J=7 Hz), 1.28(10H, m), 2.64(4H, m).

REFERENTIAL EXAMPLE 11

Production of tetrahydrofurfurylethylamine

Referential Example 10 was repeated except that tetrahydrofurfurylacetamide was used instead of heptylacetamide. Tetrahydrofurfurylethylamine was obtained in a yield of 86%.

¹H-NMR spectrum (CDCl₃ solution, δppm): 1.12(3H, t, J=7 Hz), 1.88(6H, m), 2.68 (3H, m), 3.78(4H, m).

REFERENTIAL EXAMPLE 12

Production of 3-chloropropylethylheptylamine of the formula

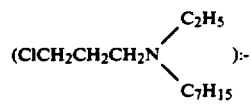

A mixture of 30 g 0.19 mole) of 1-bromo-3-chloropropane, 25 g (0.17 mole) of ethylheptylamine, 28 g (0.20 mole) of potassium carbonate and 250 ml of toluene was refluxed for 8 hours. After cooling, the solid was collected by filtration, and concentrated. The residue was purified by silica gel column chromatography (ethyl acetate) to give 17 g of the desired compound (yield 44%).

¹H-NMR spectrum (CDCl₃ solution, δppm): 0.90(3H, t, J=7 Hz), 1.02(3H, t, J=7 Hz), 1.30(10H, m), 1.90(2H, m), 2.50(6H, m), 3.60 (2H, t, J=7 Hz).

REFERENTIAL EXAMPLES 13 to 18

The amines indicated in Table 2 were produced from Referential Example 12.

TABLE 2

ClCH₂CH₂CH₂R¹

| Referential Example No. | R¹ | Yield (%) | Melting point (°C.) (%) | ¹H-NMR spectrum (CDCl₃ solution, δ ppm) |
|---|---|---|---|---|
| 13 |  | 41 | oil | 1.50–2.05 (12H, m), 2.56 (6H, m), 3.66 (2H, t, J=7Hz) |
| 14 |  | 17 | oil | 1.94 (3H, t, J=7Hz), 2.25 (2H, t, J=2Hz), 2.71 (2H, t, J=7Hz), 3.53 (2H, d, J=2Hz), 3.56 (4H, m) |

TABLE 2-continued

| Referential Example No. | R¹ (ClCH₂CH₂CH₂R¹) | Yield (%) | Melting point (°C.) | ¹H-NMR spectrum (CDCl₃ solution, δ ppm) |
|---|---|---|---|---|
| 15 | −N(CH₂−CH=CH₂)₂ | 33 | oil | 2.22 (2H, m), 2.98 (2H, t, J=7Hz), 3.60 (6H, m), 5.50 (4H, m), 6.00 (2H, m) |
| 16 | −N(Et)(CH₂-tetrahydrofuran) | 27 | oil | 1.04 (3H, t, J=7Hz), 1.90 (6H, m), 2.60 (6H, m), 3.70 (5H, m) |
| 17 | −N(C₃H₇)(CH₂CH₂OCH₃) | 33 | oil | 0.88 (3H, t, J=7Hz), 1.45 (2H, m), 1.90 (2H, m), 2.44 (2H, m), 2.63 (4H, t, J=7Hz), 3.36 (3H, s), 3.46 (2H, t, J=7Hz), 3.62 (2H, t, J=7Hz) |
| 18 | −N(3,4-dimethylpyrrolidine) | 15 | oil | 0.90 (12H, d, J=7Hz), 1.08 (2H, m), 2.08 (4H, d, J=7Hz), 2.47 (2H, t, J=7Hz), 3.64 (2H, t, J=7Hz) |

EXAMPLE 1

Production of 6-3-(N-ethyl-N-heptylamino)propoxy]coumaran-3-one (compound No. 100):

A mixture composed of 4.4 g 31.9 millimoles) of 6-hydroxycoumaran-3-one, 6 g (27.3 millimoles) of 3-chloropropylethylheptylamine, 4.8 g (34.8 millimoles) of potassium carbonate and 120 ml of toluene was refluxed for 30 hours. After cooling, the solid was collected by filtration and concentrated. The residue was purified by silica gel column chromatography (CH₂/MeOH=95/5) to give 3.4 g (yield 37%) of the desired compound as an oil.

¹H-NMR spectrum (CDCl₃ solution, δppm): 0.80(3H, t, J=7 Hz), 1.02(3H, t, J=7 Hz), 1.98(2H, m), 2.54(4H, m), 4.10(2H, t, J=7 Hz), 4.63(2H, s), 6.58(1H, d, J=2 Hz), 6.64 (1H, dd, J=2 and 9 Hz), 7.56(1H, d, J=9 Hz).

EXAMPLES 2 TO 20

In the same way as in Example 1, the compounds shown in Table 3 were produced from the corresponding starting compounds.

TABLE 3

| Example No. | Compound No. | Yield (%) | Melting point (°C.) | ¹H-NMR spectrum (CDCl₃ solution, δ ppm) |
|---|---|---|---|---|
| 2 | (150) | 14 | oil | 1.99(2H, t, J=7Hz), 2.24(2H, t, J=2Hz), 2.75(2H, t, J=7Hz), 3.47(4H, d, J=2Hz), 4.12(2H, t, J=7Hz), 4.63 (2H, s), 6.56(1H, d, J=2Hz), 6.64(1H, dd, J=2 and 9Hz), 7.55(1H, d, J=7Hz) |
| 3 | (154) | 25 | oil | 1.95(2H, m), 2.62(2H, t, J=7Hz), 3.10(4H, dt, J=1.5 and 7Hz), 4.08(2H, t, J=7Hz), 4.63(2H, s), 5.18(4H, m), 5.80(2H, m), 6.55(1H, d, J=2Hz), 6.62(1H, dd, J=2 and 9Hz), 7.56(1H, d, J=9Hz) |
| 4 | (182) | 39 | oil | 1.04(3H, t, J=7Hz), 1.90(6H, m), 2.60(6H, m), 3.84(3H, m), 4.12(2H, t, J=7Hz), 4.63(2H, s), 6.58(1H, d, J=2Hz), 6.64(1H, dd, J=2 and 9Hz), 7.56(1H, d, J=9Hz) |
| 5 | (178) | 39 | oil | 0.88(3H, t, J=7Hz), 1.47(2H, m), 1.95(2H, m), 2.47(2H, m), 2.67(4H, t, J=7Hz), 3.34(3H, s), 3.46(2H, t, J=7Hz), 4.12(2H, t, J=7Hz), 4.63(2H, s), 6.56(1H, d, J=2Hz), 6.64(1H, dd, J=2 and 9Hz), 7.57(1H, d, J=9Hz) |
| 6 | (130) | 15 | oil | 0.88(12H, d, J=7Hz), 1.76(4H, m), 2.10(4H, d, J=7Hz), 2.52(2H, t, J=7Hz), 4.12(2H, t, J=7Hz), 4.63(2H, s), 6.55(1H, d, J=2Hz), 6.64(1H, dd, J=2 and 9Hz), 7.58 (1H, d, J=9Hz) |
| 7 | (158) | 87 | — | 1.0-2.5(13H, m), 2.65(2H, t, J=7Hz), 2.15(2H, dt, J=1.5 and J=7Hz), 4.10(2H, t, J=7Hz), 4.63(2H, s), 4.9-5.3 (2H, m), 5.80(1H, m), 6.56(1H, d, J=2Hz), 6.64(1H, dd, J=2 and 9Hz), 7.57(1H, d, J=9Hz) |
| 8 | (170) | 15 | — | 1.35(3H, t, J=7Hz), 1.68-2.40(17H, m), 3.06(4H, m), 4.17(2H, t, J=7Hz), 4.64(2H, s), 6.56(1H, d, J=2Hz), 6.64(1H, dd, J=2 and 9Hz), 7.56(1H, d, J=9Hz) |
| 9 | (226) | 70 | oil | 0.88(3H, t, J=5Hz), 1.06(3H, t, J=7Hz), 1.27(10H, m), 2.00(2H, m), 2.18(3H, s), 2.56(6H, m), 4.12(2H, t, J=5Hz), 4.61(2H, s), 6.52(1H, s), 7.40(1H, s) |
| 10 | (222) | 20 | oil | 0.88(3H, t, J=5Hz), 1.06(3H, t, J=7Hz), 1.27(10H, m), 1.96(2H, m), 2.50(3H, s), 2.60(6H, m), 4.08(2H, t, J=5Hz), 4.58(2H, s), 6.38(2H, s) |
| 11 | (242) | 70 | oil | 0.88(3H, t, J=5Hz), 1.06(3H, t, J=7Hz), 1.28(10H, m), 2.02(2H, m), 2.60(6H, m), 4.00(3H, s), 4.20(2H, t, |

TABLE 3-continued

| Example No. | Compound No. | Yield (%) | Melting point (°C.) | 1H-NMR spectrum (CDCl3 solution, δ ppm) |
|---|---|---|---|---|
| | | | | J=5Hz), 4.67(2H, s), 6.74(1H, d, J=9Hz), 7.39(1H, d, J=9Hz) |
| 12 | (230) | 59 | oil | 0.88(3H, t, J=5Hz), 1.08(3H, t, J=7Hz), 1.28(10H, m), 2.00(2H, m), 2.18(3H, s), 2.58(6H, m), 4.16(2H, t, J=5Hz), 4.65(2H, s), 6.66(1H, d, J=9Hz), 7.53(1H, d, J=9Hz) |
| 13 | (234) | 54 | oil | 0.88(3H, t, J=5Hz), 1.07(3H, t, J=7Hz), 1.27(10H, m), 2.06(2H, m), 2.62(6H, m), 4.20(2H, t, J=5Hz), 4.66 (2H, s), 6.66(1H, s), 7.68(1H, s) |
| 14 | (246) | 35 | oil | 0.88(3H, t, J=5Hz), 1.03(3H, t, J=7Hz), 1.07(10H, m), 1.52(3H, d, J=7Hz), 1.94(2H, m), 2.53(6H, m), 4.10(2H, t, J=5Hz), 4.64(1H, q, J=7Hz), 6.52(1H, d, J=2Hz), 6.64 (1H, dd, J=2 and 9Hz), 7.56(1H, d, J=9Hz) |
| 15-1 | (800) | 30 | oil | — |
| 15-2 | (300) | 65 | oil | 0.88(3H, t, J=7Hz), 1.05(3H, t, J=7Hz), 1.28(10H, m), 1.96(2H, m), 2.60(8H, m), 3.10(2H, m), 4.12(2H, t, J=7Hz), 6.90(1H, dd, J=2 and 9Hz), 6.94(1H, d, J=2Hz), 7.70(1H, d, J=9Hz) |
| 16 | (400) | 39 | oil | — |
| 17 | (930) | 58 | oil | 0.86(3H, t, J=5Hz), 1.08(3H, t, J=7Hz), 1.2-1.7(10H, m), 2.0(2H, m), 2.3-3.0(6H, m), 4.13(2H, t, J=5Hz), 6.9-8.0 (7H, m) |
| 18 | (950) | 40 | oil | 0.88(3H, t, J=5Hz), 1.07(3H, t, J=7Hz), 1.27(10H, m), 2.0(2H, m), 2.60(6H, m), 4.04(2H, t, J=5Hz), 6.84(1H, dd, J=2 and 9Hz), 6.89(1H, d, J=2Hz), 7.26(1H, d, J=9Hz) |
| 19 | (608) | 87 | — | — |
| 20 | (700) | 73 | oil | 0.88(3H, t, J=5Hz), 1.04(3H, t, J=7Hz), 1.28(10H, m), 1.88(2H, m), 2.52(6H, m), 3.94(2H, t, J=5Hz), 5.92 (2H, s), 6.32(1H, dd, J=2 and 7Hz), 6.50(1H, d, J=2Hz), 6.70(1H, d, J=7Hz) |
| 21 | (750) | 85 | oil | 0.89(3H, t, J=5Hz), 1.04(3H, t, J=7Hz), 1.30(10H, m), 1.7-3.0(14H, m), 4.0(2H, t, J=5Hz), 6.70(1H, dd, J=2 and 9Hz), 6.80(1H, d, J=2Hz), 7.12(1H, d, J=9Hz) |
| 22 | (900) | 26 | oil | 0.90(3H, t, J=5Hz), 1.06(3H, t, J=7Hz), 1.36(16H, m), 1.6-2.1(4H, m), 2.3-2.8(8H, m), 3.96(2H, t, J=5Hz), 6.37(1H, d, J=2Hz), 6.42(1H, dd, J=2 and 9Hz), 6.94 (1H, d, J=9Hz) |
| 23 | (612) | 76 | — | 0.88(3H, t, J=7Hz), 1.04(3H, t, J=7Hz), 1.28(10H, m), 1.8-2.7(14H, m), 4.08(2H, t, J=Hz), 6.08(1H, d, J=2Hz), 6.86(1H, dd, J=2 and 9Hz), 7.50(1H, d, J=9Hz) |
| 24 | (850) | 56 | — | 0.88(3H, t, J=5Hz), 1.04(3H, t, J=7Hz), 1.2-2.1(20H, m), 2.3-2.7(6H, m), 4.02(2H, t, J=5Hz), 6.77(1H, dd, J=2 and 7Hz), 6.83(1H, d, J=2Hz), 7.0(1H, d, J=7Hz) |
| 25 | (804) | 76 | — | 0.8-2.0(26H, m), 2.3-2.7(8H, m), 4.05(2H, t, J=7Hz), 6.38(1H, d, J=2Hz), 6.52(1H, dd, J=2 and 9Hz), 7.78 (1H, d, J=9Hz) |
| 26 | (704) | 74 | oil | 0.8-1.6(22H, m), 1.8-2.2(4H, m), 2.3-2.7(6H, m), 3.60 (2H, q, J=7Hz), 3.94(2H, t, 5Hz), 6.2-6.8(3H, m) |
| 27 | (404) | 85 | oil | 0.8-2.1(29H, m), 2.52(6H, m), 3.12(1H, m), 3.96(2H, t, J=7Hz), 6.34(1H, t, J=2Hz), 6.38(1H, dd, J=2 and 9Hz), 6.94(1H, d, J=9Hz) |
| 28 | (616) | 34 | oil | 0.88(3H, t, J=7Hz), 1.06(3H, t, J=7Hz), 1.27(10H, m), 1.38(6H, d, J=7Hz), 2.00(2H, m), 2.43(3H, s), 2.56 (6H, m), 3.30(1H, m), 4.08(2H, t, J=7Hz), 6.80(1H, d, J=2Hz), 6.85(1H, dd, J=2 and 9Hz), 7.52(1H, d, J=9Hz) |
| 29 | (350) | 43 | oil | 0.92(3H, t, J=7Hz), 1.02(3H, t, J=7Hz), 1.26(10H, br, s), 1.97(2H, q, J=7Hz), 2.50(6H, m), 4.04(2H, t, J=7Hz), 6.68(1H, d, J=2Hz), 6.86(1H, dd, J=2 and 9Hz), 7.03 (1H, s), 7.43(1H, d, J=9Hz), 7.52(1H, d, J=2Hz) |

EXAMPLE 30

Production of
6-3-(N-ethyl-N-heptylamino)propyloxycoumaran-3-one hydrochloride (compound No. (102):

3.4 g (10.2 moles) of 6-[3-(N-ethyl-N-heptylamino)-propyloxy coumaran-3-one was dissolved in 30 ml of acetonitrile, and 1.0 g 10.2 millimoles) of concentrated hydrochloric acid was added. The mixture was stirred for 0.5 hour. Then, the solvent was evaporated under reduced pressure, and the residue was crystallized from ethyl acetate/ether to give 3.5 g (yield 95%) of the desired compound.

Melting point: 92°–93° C.

1H-NMR spectrum (CDCl3 solution, ppm): 0.90(3H, t, J=5 Hz), 1.34(11H, m), 1.88 (2H, m), 2.48(2H, m), 3.20(6H, m), 4.20 (2H, t, J=5 Hz), 4.64(2H, s), 6.58(1H, d, J=2 Hz), 6.62(1H, dd, J=2 and 9 Hz), 7.58 (1H, d, J=9 Hz).

EXAMPLES 31 TO 56

In the same way as in Example 30, the compounds indicated in Table 4 were obtained from the corresponding starting compounds.

TABLE 3

| Example No. | Compound No. | Yield (%) | Melting point (°C.) | ¹H-NMR spectrum (CDCl₃ solution, δ ppm) |
|---|---|---|---|---|
| 31 | (152) | 14 | 173-175 | 2.40(2H, m), 3.40(4H, m), 4.20(6H, m), 4.66(2H, s), 6.68(2H, m), 7.54(1H, d, J=9Hz) |
| 32 | (156) | 25 | 169-171 | 2.50(2H, m), 3.20(2H, m), 3.72(4H, m), 4.20(2H, t, J=5Hz), 4.62(2H, s), 5.58(4H, m), 6.20(2H, m), 6.56 (1H, d, J=2Hz), 6.62(1H, dd, J=2 and 9Hz), 7.59(1H, d, J=9Hz) |
| 33 | (184) | 31 | 50-53 | 1.46(3H, m), 1.8-2.6(6H, m), 3.30(6H, m), 3.86(2H, m), 4.18(2H, t, J=5Hz), 4.48(1H, m), 4.64(2H, s), 6.56 (1H, d, J=2Hz), 6.62(1H, dd, J=2 and 9Hz), 7.58(1H, d, J=9Hz) |
| 34 | (180) | 36 | 130-132 | 1.02(3H, t, J=7Hz), 1.94(2H, m), 2.47(2H, m), 3.20 (6H, m), 3.40(3H, s), 3.92(2H, m), 4.18(2H, t, J=5Hz), 4.64(2H, s), 6.56(1H, d, J=2Hz), 6.62(1H, dd, J=2 and 9Hz), 7.57(1H, d, J=9Hz) |
| 35 | (132) | 17 | 147-151 | 1.20(12H, d, J=7Hz), 2.2-2.4(4H, m), 2.97(4H, m), 3.22(2H, m), 4.18(2H, m), 4.64(2H, s), 6.55(1H, d, J=2Hz), 6.62(1H, dd, J=2 and 9Hz), 7.59(1H, d, J=9Hz) |
| 36 | (160) | 61 | 54-58 | 1.1-2.1(8H, m), 2.1-2.7(4H, m), 3.26(3H, m), 3.75(2H, t, J=5Hz), 4.20(2H, t, J=5Hz), 4.63(2H, s), 5.52 (2H, m), 6.30(1H, m), 6.56(1H, d, J=2Hz), 6.62(1H, dd, J=2 and 9Hz), 7.56(1H, d, J=9Hz), 12.1(1H, brs) |
| 37 | (172) | 81 | 105-108 (decomp.) | 1.22(3H, t, J=7Hz), 1.4-3.3(17H, m), 3.48(4H, m), 4.22(2H, m), 4.63(2H, s), 6.58(1H, d, J=2Hz), 6.64 (1H, dd, J=2 and 9Hz), 7.56(1H, d, J=9Hz) |
| 38 | (228) | 59 | 91-93 | 0.90(3H, m), 1.34(11H, m), 1.84(2H, m), 2.18(3H, s), 2.52(2H, m), 3.20(6H, m), 4.20(2H, t, J=5Hz), 4.62 (2H, s), 6.52(1H, s), 7.42(1H, s) |
| 39 | (224) | 19 | 69-73 | 0.90(3H, m), 1.34(11H, m), 1.84(2H, m), 2.48(2H, m), 2.56(3H, s), 3.18(6H, m), 4.16(2H, t, J=5Hz), 4.59 (2H, s), 6.36(2H, s) |
| 40 | (244) | 65 | 107-110 | 0.90(3H, t, J=5Hz), 1.36(11H, m), 1.88(2H, m), 2.48 (2H, m), 3.20(6H, m), 4.00(3H, s), 4.27(2H, t, J=5Hz), 4.68(2H, s), 6.70(1H, d, J=9Hz), 7.38(1H, d, J=9Hz) |
| 41 | (232) | 59 | 72-74 | 0.88(3H, t, J=5Hz), 1.33(13H, m), 1.84(2H, m), 2.14 (3H, s), 2.50(2H, m), 3.20(6H, m), 4.23(2H, t, J=5Hz), 4.64(2H, s), 16.65(1H, d, J=9Hz), 7.54(1H, d, J=9Hz) |
| 42 | (236) | 61 | 89-91 | 0.90(3H, m), 1.34(11H, m), 1.84(2H, m), 2.54(2H, m), 3.20(6H, m), 4.28(2H, t, J=5Hz), 4.66(2H, s), 6.66 (1H, s), 7.66(1H, s) |
| 43 | (248) | 30 | oil | 0.90(3H, t, J=5Hz), 1.34(11H, m), 1.54(3H, d, J=7Hz), 1.88(2H, m), 2.50(2H, m), 3.20(6H, m), 4.20(2H, m), 4.66(1H, q, J=7Hz), 6.54(1H, d, J=2Hz), 6.62(1H, dd, J=2 and 9Hz), 7.58(1H, d, J=9Hz) |
| 44 | (602) | 70 | 103-105 | — |
| 45 | (802) | 85 | 85-88 | 0.89(3H, t, J=5Hz), 1.1-1.6(11H, m), 1.84(2H, m), 2.44(2H, m), 2.76(2H, t, J=7Hz), 3.16(6H, m), 4.14 (2H, t, J=5Hz), 4.53(2H, t, J=7Hz), 6.40(1H, d, J=2Hz), 6.52(1H, dd, J=2 and 9Hz), 7.85(1H, d, J=9Hz), 12.3(1H, brs) |
| 46 | (302) | 58 | 71-75 | 0.89(3H, t, J=5Hz), 1.2-1.6(3H, m), 1.84(2H, t), 2.2-2.8(4H, m), 3.12(8H, m), 4.20(2H, t, J=5Hz), 6.86 (1H, dd, J=2 and 9Hz), 16.92(1H, d, J=2Hz), 7.68(1H, d, J=9Hz), 12.2(1H, brs) |
| 47 | (402) | 95 | 107-109 | 0.90(3H, t, J=5Hz), 1.34(11H, m), 1.80(2H, m), 2.37 (2H, m), 2.8-3.4(8H, m), 4.04(2H, t, J=5Hz), 4.58 (2H, t, J=7Hz), 6.32(1H, d, J=2Hz), 6.36(1H, d, J=2 and 9Hz), 7.07(1H, d, J=9Hz) |
| 48 | (932) | 80 | 63-68 | — |
| 49 | (952) | 75 | 108-111 | 0.90(3H, t, J=5Hz), 1.34(11H, m), 1.80(2H, t), 2.40 (2H, m), 3.20(6H, m), 4.10(2H, m), 6.82(1H, dd, J=2 and 9Hz), 6.88(1H, d, J=2Hz), 7.30(1H, d, J=9Hz), 12.4(1H, brs) |
| 50 | (610) | 98 | 84-85 | 0.90(3H, t, J=5Hz), 1.30(11H, m), 1.90(2H, m), 2.50 (2H, m), 3.20(6H, m), 4.20(2H, t, J=5Hz), 6.27(1H, d, J=11Hz), 6.81(1H, d, J=2Hz), 6.86(1H, dd, J=2 and 9Hz), 7.42(1H, d, J=9Hz), 7.67(1H, d, J=11Hz), 12.2 (1H, brs) |
| 51 | (702) | 65 | 54-58 | 0.90(3H, t, J=5Hz), 1.1-2.0(15H, m), 2.40(2H, m), 3.15(6H, m), 4.03(2H, t, J=5Hz), 6.30(1H, d, J=2 and 7Hz), 6.46(1H, d, J=2Hz), 6.72(1H, d, J=7Hz), 12.4 (1H, brs) |
| 52 | (752) | 98 | 89-92 | 0.90(3H, t, J=5Hz), 1.1-1.6(10H, m), 1.6-2.6(7H, m), 2.7-3.4(10H, m), 4.07(2H, t, J=5Hz), 6.66(1H, dd, J=2 and 9Hz), 6.76(1H, d, J=2Hz), 7.12(1H, d, J=9Hz), 12.4(1H, brs) |
| 53 | (902) | 74 | 91-95 | 0.90(3H, t, J=5Hz), 1.35(17H, m), 1.8-2.8(8H, m), 3.14(6H, m), 4.03(2H, t, J=5Hz), 6.33(1H, d, J=2Hz), 6.38(1H, dd, J=2 and 9Hz), 6.96(1H, d, J=9Hz), 12.4 (1H, brs) |
| 54 | (614) | 98 | 87-89 | 0.90(3H, t, J=5Hz), 1.1-1.6(11H, m), 1.90(2H, m), |

TABLE 3-continued

| Example No. | Compound No. | Yield (%) | Melting point (°C.) | ¹H-NMR spectrum (CDCl₃ solution, δ ppm) |
|---|---|---|---|---|
| | | | | 2.22(3H, s), 2.38(5H, m), 3.20(6H, m), 4.18(2H, t, J=5Hz), 6.79(1H, d, J=2Hz), 6.84(1H, dd, J=2 and 9Hz), 7.52(1H, d, J=9Hz) |
| 55 | (852) | 75 | 116-118 | 0.86(3H, t, J=5Hz), 1.28(17H, m), 1.66(2H, m), 2.0-3.4(10H, m), 4.08(2H, t, J=5Hz), 6.94(3H, m) |
| 56 | (806) | 90 | 107-110 | 0.88(3H, t, J=5Hz), 0.98(3H, t, J=7Hz), 1.1-2.7(28H, m), 4.12(2H, t, J=5Hz), 6.36(1H, d, J=2Hz), 6.48(1H, dd, J=2 and 9Hz), 7.78(1H, d, J=9Hz) |
| 56-1 | (253) | 68 | — | 0.7-1.7(20H, m), 1.89(2H, t, J=7Hz), 2.10(4H, m), 2.49(2H, t, J=7Hz), 4.10(2H, t, J=7Hz), 4.63(2H, s), 6.54(1H, s), 6.63(1H, dd, J=2 and 8Hz), 7.56(1H, d, J=8Hz) |
| 56-2 | (254) | 22 | — | 1.46(9H, s), 2.50(2H, m), 3.11(2H, m), 4.16(2H, t, J=7Hz), 4.61(2H, s), 6.53(1H, s), 6.62(1H, dd, J=2 and 8Hz), 7.55(1H, d, J=8Hz) |
| 56-3 | (255) | 38 | oil | 0.88(6H, t, J=7Hz), 1.26(18H, m), 1.94(2H, t, J=7Hz), 2.0-2.7(8H, m), 4.10(2H, t, J=7Hz), 4.62(2H, s), 6.54(1H, s), 6.64(1H, dd, J=2 and 8Hz), 7.56(1H, d, J=8Hz) |
| 56-4 | (256) | 64 | — | 1.95(2H, m), 2.33(3H, s), 2.57(2H, t, J=7Hz), 2.70(4H, m), 4.02(2H, t, J=7Hz), 4.62(2H, s), 6.52(1H, s), 6.60(1H, dd, J=2 and 8Hz), 7.22(5H, m), 7.56(1H, d, J=8Hz) |
| 56-5 | (257) | 20 | — | δ7.53(d, 1H, 7Hz), 6.5-6.7(m, 2H), 4.60(s, 2H), 4.20(t, 2H, 7Hz), 4.40(br, 1H), 3.50(t, 2H, 7Hz), 1.2-2.6(13H) |
| 56-6 | (253)' | 85 | 101-104 | 0.95(9H, t, J=7Hz), 1.20(3H, d, J=7Hz), 1.57(8H, m), 2.48(2H, m), 3.00(4H, m), 3.32(2H, m), 4.18(2H, t, J=7Hz), 4.62(2H, s), 6.55(1H, s), 6.60(1H, dd, J=2 and 8Hz), 7.56(1H, d, J=8Hz) |
| 56-7 | (254)' | 52 | 190-192 (decomp.) | 1.53(9H, s), 2.60(2H, m), 3.12(2H, m), 4.14(2H, t, J=7Hz), 4.60(2H, s), 6.50(1H, s), 6.60(1H, dd, J=2 and 8Hz), 7.53(1H, d, J=8Hz) |
| 56-8 | (256)' | 79 | 161-166 | 2.50(2H, m), 2.92(3H, m), 3.27(6H, m), 4.19(2H, t, J=7Hz), 4.62(2H, s), 6.55(1H, s), 6.61(1H, dd, J=2 and 8Hz), 7.30(5H, m), 7.56(1H, d, J=8Hz) |
| 56-9 | (257)' | 80 | 93-96 | δ7.57(d, 1H, 7Hz), 6.6-6.8(m, 2H), 4.63(s, 2H), 4.23(t, 2H, 7Hz), 4.18(br, 1H), 3.58(t, 2H, 7Hz), 1.2-2.5(13H), 11.9(br, 1H) |
| 56-10 | (258) | 61 | — | 0.88(3H, t, J=7Hz), 1.05(3H, t, J=7Hz), 1.28(10H, m), 2.03(2H, m), 2.60(6H, m), 4.19(2H, t, J=7Hz), 4.58(2H, s), 6.48(1H, d, J=7Hz), 6.66(1H, d, J=7Hz), 7.50(1H, t, J=7Hz) |
| 56-11 | (258)' | 70 | 105-108 | 0.88(3H, t, J=7Hz), 1.1-2.6(18H), 3.28(6H, m), 4.22(2H, t, J=7Hz), 4.56(2H, s), 6.44(1H, d, J=8Hz), 6.70(1H, d, J=8Hz), 7.15(2H, d, J=7Hz), 7.51(1H, t, J=8Hz), 7.76(2H, d, J=7Hz) |
| 56-12 | (259)' | 90 | 212-214 | δ7.56(d, 1H, J=9Hz), δ6.6-6.8(m, 2H), δ4.72(s, 2H), δ4.21(t, 2H, J=7Hz), δ2.8-3.4(m, 3H), δ2.17(dt, 2H, J=7.7Hz), δ1.32(d, 6H, J=7Hz), δ8.7(br, 2H) |
| 56-13 | (260)' | 83 | oil | δ7.56(d, 1H, J=9Hz), δ6.4-6.8(m, 2H), δ4.64(s, 2H), δ4.22(t, 2H, J=7Hz), δ2.9-3.4(m, 5H), δ2.4-2.8(m, 2H), δ1.2-1.7(m, 6H), δ1.16(d, 6H, J=7Hz), δ0.92(t, 3H, J=7Hz), δ11.6(br, 1H) |
| 56-14 | (261)' | 94 | 82-86 | δ7.55(d, 1H, J=9Hz), δ6.5-6.8(m, 2H), δ4.62(s, 2H), δ4.20(t, 2H, J=7Hz), δ2.8-3.4(m, 5H), δ2.2-2.7(m, 2H), δ1.3-1.8(m, 8H), δ1.17(d, 6H, J=7Hz), δ0.92(t, 3H, J=7Hz), δ11.8(br, 1H) |
| 56-15 | (262)' | 92 | 122-128 | δ7.57(d, 1H, J=9Hz), δ6.4-6.8(m, 2H), δ4.63(s, 2H), δ4.21(t, 2H, J=7Hz), δ2.9-3.3(m, 5H), δ2.4-2.8(m, 2H), δ1.1-1.7(m, 10H), δ1.14(d, 6H, J=7Hz), δ0.88(t, 3H, J=7Hz), δ11.6(br, 1H) |
| 56-16 | (263)' | 94 | 230-233 | δ7.58(d, 1H, J=9Hz), δ6.7-6.9(m, 2H), δ4.68(s, 2H), δ4.47(t, 2H, J=5Hz), δ3.4-3.6(m, 3H), δ1.41(d, 6H, J=7Hz) |
| 56-17 | (264)' | 92 | 78-86 | δ7.56(d, 1H, J=9Hz), δ6.5-6.8(m, 2H), δ4.62(s, 2H), δ4.43(t, 2H, J=5Hz), δ3.3-3.7(m, 4H), δ1.54(d, 6H, J=7Hz), δ1.60(d, 6H, J=7Hz), δ11.6(br, 1H) |
| 56-18' | (269)' | 87 | 185-187 | δ7.60(d, 1H, J=9Hz), δ6.6-6.9(m, 2H), δ7.3-7.7(m, 5H), δ4.66(s, 2H), δ4.24(t, 2H, J=7Hz), δ3.50(t, 2H, J=7Hz), δ2.40(dt, 2H, J=7, 7Hz) |
| 56-19 | (270)' | 96 | 48-56 | δ7.60(d, 1H, J=9Hz), δ7.6-8.0(m, 5H), δ6.4-6.7(m, 2H), δ4.62(s, 2H), δ4.05(t, 2H, J=7Hz), δ3.65(t, 2H, J=7Hz), δ3.22(s, 3H), δ2.30(dt, 2H, J=7,7Hz), δ10.8(br, 1H) |
| 56-20 | (271)' | 96 | 100-104 | δ7.56(d, 1H, J=9Hz), δ6.6-6.8(m, 2H), δ4.65(s, 2H), δ4.14(t, 2H, J=7Hz), δ3.88(t, 2H, J=7Hz), δ3.28(s, 3H), δ2.76(s, 3H), δ2.17(dt, 2H, J=7,7Hz) |
| 56-21 | (274)' | 74 | 112-118 | 1.00(6H, t, J=7Hz), 1.60(8H, m), 3.20(6H, m), 4.16(2H, m), 4.62(2H, s), 4.70(1H, m), 5.80(1H, m), 6.63 |

TABLE 3-continued

| Example No. | Compound No. | Yield (%) | Melting point (°C.) | ¹H-NMR spectrum (CDCl₃ solution, δ ppm) |
|---|---|---|---|---|
| 56-22 | (275)' | 92 | 105–109 | (2H, m), 7.57(1H, d, J=8Hz) δ7.56(d, 1H, J=9Hz), δ6.64(dd, 1H, J=2,9Hz), δ6.58 (d, 1H, J=2Hz), δ4.62(s, 2H), δ4.20(t, 2H, J=7Hz), δ3.90(s, 3H), δ3.8–4.1(m, 2H), δ3.0–3.6(m, 4H), δ2.3–2.7(m, 2H), δ1.7–2.1(m, 2H), δ1.2–1.7(m, 4H), 0.97(t, 3H, J=7Hz), δ12.0(br, 1H) |
| 56-23 | (276)' | 92 | 81–84 | δ7.57(d, 1H, J=9Hz), δ6.62(dd, 1H, J=2, 9Hz), δ6.54 (d, 1H, J=2Hz), δ4.62(s, 2H), δ4.17(t, 2H, J=7Hz), δ3.90(s, 6H), δ3.3–3.7(m, 8Hz), δ2.3–2.7(m, 8H), δ12.0(br, 1H) |
| 56-24 | (356) | 86 | 43–51 | δ7.95(d, 1H, J=10Hz), δ6.9–7.1(m, 2H), δ4.16(t, 2H, J=7Hz), δ2.8–3.5(m, 6H), δ2.45(s, 3H), δ2.2–2.6(m, 2H), δ1.2–2.0(m, 8H), δ1.00(t, 6H, J=5Hz), δ12.0 (br, 1H) |
| 56-25 | (360) | 83 | 70–76 | δ8.0–8.2(m, 2H), δ7.3–7.8(m, 4H), δ6.9–7.2(m, 2H), δ4.20(t, 2H, J=7Hz), δ2.9–3.6(m, 6H), δ2.3–2.7(m, 2H), δ1.2–2.1(m, 8H), δ1.00(t, 6H, J=5Hz) |
| 56-26 | (622) | 92 | 40–48 | δ7.2–7.7(m, 6H), δ6.7–7.0(m, 2H), δ6.21(s, 1H), δ4.22(t, 2H, J=7Hz), δ2.8–3.6(m, 8H), δ2.2–2.7(m, 2H), δ1.6–2.1(m, 4H), δ1.2–1.6(m, 4H), δ1.00(t, 6H, J=5Hz), δ12.1(br, 1H) |
| 56-27 | (943) | 89 | 56–61 | δ7.85(d, 1H, J=7Hz), δ7.2–7.6(m, 7H), δ4.24(t, 2H, J=7Hz), δ2.9–3.5(m, 6H), δ2.3–2.7(m, 2H), δ1.2–2.1 (m, 8H), δ1.00(t, 6H, J=5Hz), δ12.1(br, 1H) |
| 56-28 | (978) | 92 | 97–101 | δ7.80(d, 1H, J=7Hz), δ6.4–6.6(m, 2H), δ4.20(t, 2H, J=7Hz), δ3.94(s, 3H), δ2.8–3.6(m, 6H), δ2.57(s, 3H), δ2.2–2.7(m, 2H), δ1.2–2.1(m, 8H), δ1.00(t, 6H, J=5Hz), δ10.3(br, 1H) |
| 56-29 | (941) | 97 | 107–112 | 6.5(br, 1H), 7.0–7.9(m, 3H), 4.33(t, 2H, J=7Hz), 3.0–3.6(m, 6H), 2.1–2.6(m, 2H), 1.6–2.0(m, 4H), 1.2–1.6(m, 4H), 0.94(t, 6H, J=6Hz), 11.1(br, 1H) |

EXAMPLE 30-1

Production of 6-(3-N-methylamino)propyloxycoumaran-3-one hydrobromide (compound No. 267'):

By repeating Example 30 using hydrobromic acid instead of concentrated hydrochloric acid, compound No. 267' was obtained in a yield of 97%.

Melting point: 202°–204° C.

¹H-NMR spectrum (CDCl₃ solution, δppm): 7.45(d, 1H, J=9 Hz), 6.6–6.9(m, 2H), 4.69 (s, 2H), 4.20(t, 2H, J=7 Hz), 3.12(t, 2H, J=7 Hz), 2.24(dt, 2H, J=7, 7 Hz), 2.64(s, 3H).

REFERENTIAL EXAMPLE 19

Production of 6-(3-chloropropyloxy)coumaran-3-one of the following formula:

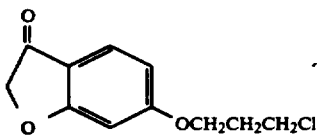

A mixture composed of 2 g (13.3 millimoles) of 6-hydroxycoumaran-3-one, 2.1 g (13.3 millimoles) of 1-bromo-3-chloropropane, 1.85 g (13.3 millimoles) of potassium carbonate and 40 ml of dimethylformamide was stirred at 80° C. for 2.5 hours. Then, the solvent was evaporated under reduced pressure, and the residue was extracted by adding water and ethyl acetate. The ethyl acetate layer was washed with a saturated aqueous solution of sodium chloride, dried over magnesium sulfate, and concentrated to give 2.6 g (yield 87%) of the desired compound.

¹H-NMR spectrum (CDCl₃ solution, δppm): 2.32(2H, m), 3.77(2H, t, J=7.2 Hz), 4.22 (2H, t, J=7.2 Hz), 4.64(2H, s), 6.60(1H, d, J=2 Hz), 6.65(1 H, dd, J=2 and 9 Hz), 7.58(1H, d, J=9 Hz).

REFERENTIAL EXAMPLES 20 TO 22

In the same way as in Referential Example 19 except that 1-bromo-2-chloroethane, 1-bromo-4-chlorobutane and 1-bromo-3-chloro-2-methylpropane were used respectively instead of 1-bromo-3-chloropropane. Thus, the compounds indicated in Table 5 were obtained.

TABLE 5

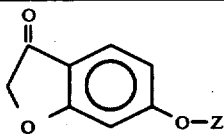

| Referential Example No. | Z | Yield (%) | ¹H-NMR spectrum (CDCl₃ solution, δ ppm) |
|---|---|---|---|
| 20 | CH₂CH₂Cl | 83 | 3.85 (2H, t, J=7.0Hz), 4.32 (2H, t, J=7Hz), 4.76 (2H, s), 6.60 (1H, d, J=2Hz), 6.65 (1H, dd, J=2 and 9Hz), 7.62 1H, d, J=9Hz). |
| 21 | CH₂CH₂CH₂CH₂Cl | 93 | 2.0 (4H, m), 3.63 (2H, m), 4.1 (2H, m), 4.64 (2H, s), 6.58 (1H, d, J=2Hz), 6.63 (1H, dd, J=2 and 9Hz), 7.59 (1H, d, J=9Hz). |

TABLE 5-continued

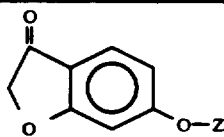

| Referential Example No. | Z | Yield (%) | $^1$H-NMR spectrum (CDCl$_3$ solution, δ ppm) |
|---|---|---|---|
| 22 | CH$_2$—CH—CH$_2$Cl<br>   \|<br>   CH$_3$ | 34 | 1.17 (3H, d, J=7.2Hz), 2.20 (1H, m), 3.68 (2H, d, J=7.2Hz), 4.03 (2H, d, J=7.2Hz), 4.64 (2H, s), 6.58 (1H, s), 6.64 1H, dd, J=2 and 9Hz), 7.58 (1H, d, J=9Hz). |

EXAMPLE 57

Production of 6-3-(N-ethyl-N-pentylamino)propyloxy)coumaran-3-one (compound No. 106):

A mixture of 2 g (8.8 millimoles) of 6-(3-chloropropyloxy)coumaran-3-one, 1.5 g (13.2 millimoles) of ethylpentylamine, 1.82 g (13.2 millimoles) of potassium hydrochloride and 30 ml of dimethylformamide was stirred at 70° C. for 10 hours. The solvent was then evaporated under reduced pressure. The residue was extracted by adding water and ether. The etheral layer was washed with water and dried over magnesium sulfate. The concentrate was purified by silica gel column chromatography (CH$_3$OH/CHCl$_3$=1/30) to give 0.9 g (yield 33%) of the desired compound.

$^1$H-NMR spectrum (CDCl$_3$ solution, δppm): 0.89(3H, t, J=4 Hz), 1.04(3H, t, J=4 Hz), 1.30(6H, m), 2.0(2H, q, J=7 Hz), 2.52 (6H, m), 4.10(2H, t, J=4 Hz), 4.62(2H, s), 6.59(1H, d, J=2 Hz), 6.64(1H, dd, J=2 and 9 Hz), 7.56(1H, d, J=9 Hz).

EXAMPLES 58 TO 65

The compounds indicated in Table 6 were produced from the corresponding starting compounds in the same way as in Example 57.

TABLE 6

| Example No. | Compound No. | Yield (%) | Melting point (°C.) | $^1$H-NMR spectrum (CDCL$_3$ solution, δ ppm) |
|---|---|---|---|---|
| 58 | (194) | 20 | | 0.89(3H, t, J=4Hz), 1.06(3H, t, J=4Hz), 1.3(10H, m), 2.52(2H, t, J=7.2Hz), 2.67(2H, t, J=7.2Hz), 2.90(2H, t, J=5Hz), 4.1(2H, t, J=5Hz), 4.63(2H, s), 6.58(1H, d, J=2Hz), 6.64(1H, dd, J=2 and 9Hz), 7.58(1H, d, J=9Hz) |
| 59 | (198) | 9 | | 0.89(3H, t, J=4Hz), 1.06(3H, t, J=4Hz), 1.29(14H, m), 2.52(2H, t, J=7.2Hz), 2.67(2H, t, J=7.2Hz), 2.90(2H, t, J=5Hz), 4.1(2H, t, J=5Hz), 4.63(2H, s), 6.58(1H, d, J=2Hz), 6.64(1H, dd, J=2 and 9Hz), 7.57(1H, d, J=9Hz) |
| 60 | (142) | 21 | | 0.9(6H, m), 1.36(8H, m), 1.97(2H, q, J=7.2Hz), 2.42(4H, t, J=8Hz), 2.59(2H, t, J=7.2Hz), 4.1(2H, t, J=5Hz), 4.63(2H, s), 6.58(1H, d, J=2Hz), 6.63(1H, dd, J=2 and 9Hz), 7.57(1H, d, J=9Hz) |
| 61 | (110) | 21 | | 0.88(3H, t, J=4Hz), 1.04(3H, to, J=4Hz), 1.28(14H, m), 1.98 (2H, q, J=7.2Hz), 2.53(6H, m), 4.1(2H, t, J=5Hz), 4.63(2H, s), 6.58(1H, d, J=2Hz), 4.64(1H, dd, J=2 and 9Hz), 7.57(1H, d, J=9Hz) |
| 62 | (218) | 8 | | 0.95(6H, m), 1.27(14H, brs), 2.2(6H, m), 4.0(2H, m), 4.63(2H, s), 6.60(1H, brs), 6.64(1H, d, J=9Hz), 7.57(1H, d, J=9Hz) |
| 63 | (206) | 16 | | 0.89(3H, t, J=4Hz), 1.16(3H, t, J=4Hz), 1.6(10H, m), 2.70(6H, m), 4.08(2H, t, J=5Hz), 4.63(2H, s), 6.58(1H, d, J=2Hz), 6.64 (1H, dd, J=2 and 9Hz), 7.57(1H, d, J=9Hz) |
| 64 | (210) | 13 | | 0.89(3H, t, J=4Hz), 1.16(3H, t, J=4Hz), 1.3(6H, brs), 1.6(8H, m), 2.66(6H, m), 4.08(2H, t, J=5Hz), 4.63(2H, s), 6.58(1H, d, J=2Hz), 6.64(1H, dd, J=2 and 9Hz), 7.57(1H, d, J=9Hz) |
| 65 | (202) | 21 | | 0.95(6H, t, J=5Hz), 1.40(8H, m), 2.54(4H, t, J=5Hz), 2.89(2H, t, J=5Hz), 4.09(2H, t, J=5Hz), 4.64(2H, s), 6.58(1H, d, J=2Hz), 6.64(1H, dd, J=2 and 9Hz), 7.58(1H, d, J=9Hz) |
| 65-1 | (259) | 28 | oil | δ7.54(d, 1H, J=9Hz), δ6.4–6.8(m, 2H), δ4.8(br, 1H), δ4.60(s, 2H), δ4.16(t, 2H, J=7Hz), δ2.9–3.4(m, 3H), δ2.32(m, 2H), δ1.36(d, 6H, J=7Hz) |
| 65-2 | (260) | 15 | oil | δ7.54(d, 1H, J=9Hz), δ6.4–6.7(m, 2H), δ4.62(s, 2H), δ4.15(t, 2H, J=7Hz), δ2.7–3.3(m, 5H), δ2.3–2.7(m, 2H), δ1.2–1.7(m, 6H), δ1.10(d, 6H, J=7Hz), δ0.90(t, 3H, J=7Hz) |
| 65-3 | (261) | 25 | oil | δ7.53(d, 1H, J=9Hz), δ6.5–6.8(m, 2H), δ4.60(s, 2H), δ4.17(t, 2H, J=7Hz), δ2.7–3.4(m, 5H), δ2.2–2.7(m, 2H), δ1.2–1.7(m, 8H), δ1.12(d, 6H, J=7Hz), δ0.91(t, 3H, J=7Hz) |
| 65-4 | (262) | 22 | oil | δ7.54(d, 1H, J=9Hz), δ6.4–6.7(m, 2H), δ4.62(s, 2H), δ4.16(t, 2H, J=7Hz), δ2.8–3.4(m, 5H), δ2.2–2.7(m, 2H), δ1.10(d, 6H, J=7Hz), δ0.87(t, 3H, J=7Hz), δ1.1–1.7(m, 10H) |
| 65-5 | (263) | 57 | oil | δ7.56(d, 1H, J=9Hz), δ6.7–6.9(m, 2H), δ4.64(s, 2H), δ4.43(t, 2H, J=5Hz), δ3.3–3.6(m, 3H), δ1.38(d, 6H, J=7Hz), δ3.8(br, 1H) |
| 65-6 | (264) | 38 | oil | δ7.54(d, 1H, J=9Hz), δ6.5–6.8(m, 2H), δ4.60(s, 2H), δ4.40(t, 2H, J=5Hz), δ3.1–3.6(m, 4H), δ1.50(d, 6H, J=7Hz), δ1.56(d, 6H, J=7Hz) |
| 65-7 | (265) | 80 | oil | 0.9–2.0(20H, m), 2.48(6H, m), 4.04(2H, t, J=7Hz), 4.63(2H, s), 6.52(1H, d, J=2Hz), 6.64(1H, dd, J=8Hz), 7.57(1H, d, J=8Hz) |
| 65-8 | (266) | 54 | — | 0.9–2.0(22H, m), 2.51(6H, m), 4.02(2H, t, J=7Hz), 4.63(2H, s), 6.52(1H, d, J=2Hz), 6.62(1H, dd, J=2 and 8Hz), 7.56(1H, d, J=8Hz) |
| 65-9 | (267) | 95 | oil | δ7.40(d, 1H, J=9Hz), δ6.6–6.9(m, 2H), δ4.62(s, 2H), δ4.16(t, 2H, J=7Hz), δ3.03(t, 2H, J=7Hz), δ2.19(dt, 2H, J=7, 7Hz), δ2.53(s, 3H), δ6.8(br, 1H) |

TABLE 6-continued

| Example No. | Compound No. | Yield (%) | Melting point (°C.) | 1H-NMR spectrum (CDCL3 solution, δ ppm) |
|---|---|---|---|---|
| 65-10 | (268) | 21 | — | 1.2–3.6(15H, m), 4.13(2H, t, J=7Hz), 4.62(2H, s), 6.53(1H, d, J=2Hz), 6.63(1H, dd, J=2 and 8Hz), 7.32(5H, m), 7.56(1H, d, J=8Hz) |
| 65-11 | (269) | 33 | oil | δ7.56(d, 1H, J=9Hz), δ7.1–7.4(m, 2H), δ6.5–6.9(m, 5H), δ4.61(s, 2H), δ4.16(t, 2H, J=7Hz), δ3.7(br, 1H), δ3.36(t, 2H, J=7Hz), δ2.20(dt, 2H, J=7, 7Hz) |
| 65-12 | (270) | 28 | oil | δ7.57(d, 1H, J=9Hz), δ7.2–7.4(m, 2H), δ6.5–6.9(m, 5H), δ4.62(s, 2H), δ4.08(t, 2H, J=7Hz), δ3.55(t, 2H, J=7Hz) δ2.95(s, 3H), δ2.10(dt, 2H, J=7, 7Hz) |
| 65-13 | (271) | 33 | oil | δ7.60(d, 1H, J=9Hz), δ6.5–6.8(m, 2H), δ4.65(s, 2H), δ4.12(t, 2H, J=7Hz), δ3.84(t, 2H, J=7Hz), δ3.26(s, 3H), δ2.80(s, 3H), δ2.18(dt, 2H, J=7, 7Hz) |
| 65-14 | (275) | 34 | oil | δ7.54(d, 1H, J=9Hz), δ6.6–6.8(m, 2H), δ4.60(s, 2H), δ4.16(t, 2H, J=7Hz), δ3.81(s, 3H), δ3.6–3.9(m, 2H), δ2.9–3.5(m, 4H), δ2.2–2.6(m, 2H), δ1.2–2.0(m, 6H), δ0.95(t, 3H, J=7Hz) |
| 65-15 | (276) | 34 | oil | δ7.55(d, 1H, J=9Hz), δ6.5–6.7(m, 2H), δ4.60(s, 2H), δ4.14(t, 2H, J=7Hz), δ3.86(s, 6H), δ3.3–3.7(m, 8H), δ2.2–2.6(m, 4H) |
| 65-16 | (277) | 39 | oil | 0.7–2.3(13H, m), 2.63(4H, m), 3.44(9H, m), 4.51(2H, t, J=7Hz), 4.62(2H, s), 7.62(2H, m), 7.55(1H, d, J=8Hz) |
| 65-17 | (278) | 73 | oil | 0.90(12H, d, J=7Hz), 1.2–2.7(14H, m), 4.11(2H, t, J=7Hz), 4.63(2H, s), 6.55(1H, d, J=2Hz), 6.65(1H, dd, J=2 and 8Hz), 7.58(1H, d, J=8Hz) |
| 65-18 | (279) | 55 | oil | 0.92(6H, d, J=7Hz), 1.18(3H, t, J=7Hz), 1.6–3.9(13H, m), 4.14(2H, t, J=7Hz), 4.64(2H, s), 6.54(1H, d, J=8Hz), 6.64(1H, dd, J=2 and 8Hz), 7.57(1H, d, J=8Hz) |
| 65-19 | (280) | 26 | oil | 0.87(3H, t, J=7Hz), 1.16(9H, s), 1.2–3.8(8H, m), 3.54(2H, s), 4.13(2H, t, J=7Hz), 4.62(2H, s), 6.62(2H, m), 7.55(1H, d, J=8Hz) |
| 65-20 | (281) | 7 | oil | 0.86(3H, t, J=7Hz), 1.25(3H, t, J=7Hz), 1.44(2H, m), 1.93(2H, m), 2.24–2.90(8H, m), 4.09(2H, t, J=7Hz), 4.12(2H, q, J=7Hz), 4.63(2H, s), 6.48–6.72(2H, m), 7.56(1H, d, J=8Hz) |
| 65-21 | (282) | 16 | — | 0.87(3H, t, J=7Hz), 1.47(9H, s), 1.5–2.9(8H, m), 3.22(2H, s), 4.10(2H, t, J=7Hz), 4.60(2H, s), 6.60(2H, m), 7.53(1H, d, J=8Hz) |
| 65-22 | (283) | 37 | oil | 1.04(3H, t, J=7Hz), 1.88(4H, m), 2.60(6H, m), 3.90(4H, m), 4.11(2H, t, J=7Hz), 4.64(2H, s), 4.91(1H, t, J=4Hz), 6.56(1H, d, J=2Hz), 6.66(1H, dd, J=2 and 8Hz), 7.57(1H, d, J=8Hz) |
| 65-23 | (284) | 40 | — | 1.8–4.2(15H, m), 4.64(2H, s), 6.60(2H, m), 7.12(4H, m), 7.58(1H, d, J=8Hz) |
| 65-24 | (285) | 33 | — | 1.98(2H, m), 2.38(3H, s), 2.67(2H, m), 3.07(3H, s), 3.74(2H, s), 4.02(2H, t, J=7Hz), 4.66(2H, s), 6.42(1H, d, J=2Hz), 6.55(1H, dd, J=2 and 8Hz), 7.16(2H, d, J=8Hz), 7.54(1H, d, J=8Hz), 7.98(2H, d, J=8Hz) |
| 65-25 | (354) | 43 | oil | δ7.93(d, 1H, J=10Hz), δ6.9–7.1(m, 2H), δ4.10(t, 2H, J=7Hz), δ2.4–3.0(m, 6H), δ2.44(s, 3H), δ1.8–2.2(m, 2H), δ1.1–1.8(m, 8H), δ0.93(t, 6H, J=5Hz) |
| 65-26 | (358) | 30 | oil | δ7.9–8.2(m, 2H), δ7.3–7.8(m, 4H), δ6.9–7.1(m, 2H), δ4.12(t, 2H, J=7Hz), δ2.4–3.0(m, 6H), δ1.9–2.3(m, 2H), δ1.1–1.8(m, 8H), δ0.92(t, 6H, J=5Hz) |
| 65-27 | (620) | 60 | oil | δ7.2–7.7(m, 6H), δ6.7–7.0(m, 2H), δ6.22(s, 1H), δ6.22(s, 1H), δ4.10(t, 2H, J=7Hz), δ2.4–2.9(m, 8H), δ1.9–2.2(m, 2H), δ1.1–1.7(m, 8H), δ0.92(t, 6H, J=5Hz) |
| 65-28 | (976) | 89 | oil | 0.90(6H, m), 1.36(8H, m), 1.93(2H, m), 2.50(9H, m), 3.90(3H, s), 4.07(2H, t, J=7Hz), 6.52(2H, m), 7.82(1H, d, J=8Hz) |
| 65-29 | (980) | 50 | oil | 0.94(6H, t, J=7Hz), 1.45(8H, m) 2.14(2H, m), 2.37(3H, s), 2.52(3H, s) 2.70(6H, m), 4.10(2H, d, J=7Hz), 6.61(1H, d, J=2Hz), 6.81(1H, dd, J=2 and 8Hz), 7.84(1H, d, J=8Hz) |
| 65-30 | (984) | 50 | oil | 1.00(6H, t, J=7Hz), 1.44(4H, m), 1.84(4H, m), 2.52(5H, m), 3.12(6H, m), 4.19(2H, t, J=8Hz), 6.7–8.7(8H, m), |

EXAMPLE 66

Production of 6-3-(N-ethyl-N-pentylamino)propyloxy)coumaran-3-one p-toluenesulfonate (compound No. 108):

0.78 g (2.5 millimoles) of 3-(N-ethyl-N-pentylamino)-propyloxycoumaran-3-one was dissolved in 5 ml of ethyl acetate. Separately, 0.49 g (2.5 millimoles) of p-toluenesulfonic acid monohydrate was heated under reflux with 10 ml of toluene to remove water. The solvent was evaporated under reduced pressure. To the residue was added 5 ml of ethyl acetate to dissolve it. The solution was gradually added at room temperature to the ethyl acetate solution prepared previously. The mixture was filtered, and dried to give 1.1 g (yield 89%) of the desired compound.

Melting point: 133° to 135° C.

1H-NMR spectrum (CDCl3 solution, δppm): 0.89 (3H, t, J=4 Hz), 1.35(6H, m), 1.80 (3H, br. s), 2.37(3H, s), 2.40(2H, m), 3.1(6H, m), 4.15(2H, t, J=4 Hz), 4.62 (2H, s), 6.54(1H, br. s), 6.58(1H, dd, J=2 and 9 Hz), 7.16(2H, d, J=9 Hz), 7.58 (1H, d, J=9 Hz), 7.79(2H, d, J=9 Hz), 10.8 (1H, m).

EXAMPLES 67 TO 75

The compounds indicated in Table 7 were produced from the corresponding starting compounds in the same way as in Example 66.

TABLE 7

| Example No. | Compound No. | Yield (%) | Melting point (°C.) | $^1$H-NMR spectrum (CDCl$_3$ solution, δ ppm) |
|---|---|---|---|---|
| 67 | (196) | 87 | 126–127 | 0.89(3H, t, J=4Hz), 1.3(7H, brs), 1.43(3H, t, J=4Hz), 1.75(2H, m), 1.88(1H, s,), 2.38(3H, s), 3.25(4H, m), 3.60(2H, m), 4.58(2H, t, J=5Hz), 4.64(2H, s), 6.56(1H, s), 6.60(1H, dd, J=2 and 9Hz), 7.16(2H, d, J=9Hz), 7.58(1H, d, J=9Hz), 7.78(2H, d, J=9Hz), 11.0(1H, m). |
| 68 | (200) | 67 | 123–124 | 0.89(3H, t, J=4Hz), 1.28(10H, brs), 1.42(3H, t, J=4Hz), 1.70(4H, brs), 2.38(3H, s), 3.24(4H, m), 3.58(2H, q, J=3.6Hz), 4.58(2H, t, J=5Hz), 4.64(2H, s), 6.56(1H, s), 6.60(1H, dd, J=2 and 9Hz), 7.16(2H, d, J=9Hz), 7.58(1H, d, J=9Hz), 7.78(2H, d, J=9Hz), 11.10(1H, m). |
| 69 | (144) | 78 | 67–69 | 0.96(6H, t, J=7.2Hz), 1.55(8H, m), 2.38(3H, s), 2.39(2H, m), 3.17(6H, m), 4.13(2H, t, J=4Hz), 4.64(2H, s), 6.53(1H, d, J=2Hz), 6.58(1H, dd, J=2 and 9Hz), 7.16(2H, d, J=9Hz), 7.58(1H, d, J=9Hz), 7.80(2H, d, J=9Hz), 10.8(1H, m). |
| 70 | (112) | 59 | 106–107 | 0.89(3H, t, J=4Hz),1.26(12H, br, s), 1.40(3H, t, J=4Hz), 1.75(2H, m), 2.37(3H, s), 2.39(2H, m), 3.20(6H, m), 4.14(2H, t, J=4Hz), 4.62(2H, s), 6.54(1H, d, J=2Hz), 6.59(1H, dd, J=2 and 9Hz), 7.16(2H, d, J=9Hz), 7.58(1H, d, J=9Hz), 7.79(2H, d, J=9Hz), 10.70(1H, m). |
| 71 | (220) | 72 | 92–96 | 0.88(3H, m), 1.30(13H, m), 1.72(2H, m), 2.38(3H, s), 3.20(6H, m), 4.08(2H, m), 4.64(2H, s), 6.57(1H, s), 6.60(1H, dd, J=2 and 9Hz), 7.18(2H, d, J=9Hz), 7.58(2H, d, J=9Hz), 7.78(2H, d, J=9Hz), 10.5(1H, m). |
| 72 | (208) | 34 | 100–102 | 0.80(3H, t, J=4Hz), 1.38(6H, t, J=7.2Hz), 1.80(7H, m), 2.37(3H, s), 3.15(6H, m), 4.04(2H, t, J=4Hz), 4.64(2H, s), 6.57(1H, d, J=2Hz), 6.59(1H, dd, J=2 and 9Hz), 7.17(2H, d, J=9Hz), 7.58(1H, d, J=9Hz), 7.80(2H, d, J=9Hz), 10.70(1H, m). |
| 73 | (212) | 55 | 104–105 | 0.88(3H, t, J=4Hz), 1.30(11H, m), 1.80(6H, m), 2.36(3H, s), 3.15(6H, m), 4.04(2H, t, J=4Hz), 4.64(2H, s), 6.53(1H, d, J=2Hz), 6.58(1H, dd, J=2 and 9Hz), 7.18(2H, d, J=9Hz), 7.58(1H, d, J=9Hz), 7.80(2H, d, J=9Hz), 10.70(1H, m). |
| 74 | (104) | 88 | 105–107 | 0.89(3H, t, J=5Hz), 1.1–2.6(18H, m), 2.9–3.5(6H, m), 4.14(2H, t, J=5Hz), 4.64(2H, s), 6.52(1H, d, J=2Hz), 6.59(1H, dd, J=2 and 9Hz), 7.18(2H, d, J=9Hz), 7.57(1H, d, J=9Hz), 7.78(2H, d, J=9Hz), 10.7(1H, brs). |
| 75 | (204) | 87 | 117–119 | 0.96(6H, t, J=5Hz), 1.56(8H, m), 2.37(3H, s), 3.20(2H, s), 3.62(2H, m), 4.57(2H, m), 4.64(2H, s), 6.53(1H, s), 6.60(1H, dd, J=2 and 9Hz), 7.17(2H, d, J=9Hz), 7.58(1H, d, J=9Hz), 7.78(2H, d, J=9Hz). |
| 75-1 | (265)' | 90 | Oil | 0.9–2.0(20H, m), 2.35(3H, s), 3.05(6H, m), 4.01(2H, t, J=7Hz), 4.63(2H, s), 6.58(2H, m), 7.16(2H, d, J=7Hz), 7.56(1H, d, J=8Hz), 7.78(2H, d, J=7Hz). |
| 75-2 | (266)' | 90 | Oil | 0.9–2.0(22H, m), 2.16(3H, s), 3.05(6H, m), 4.02(2H, t, J=7Hz), 4.63(2H, s), 6.52(1H, d, J=2Hz), 6.64(1H, dd, J=2 and 8Hz), 7.18(2H, d, J=7Hz), 7.57(1H, d, J=8Hz), 7.78(2H, d, J=7Hz). |
| 75-3 | (268)' | 90 | 130–136 | 2.0–4.1(20H, m), 4.56(2H, s), 6.48(2H, m), 7.0–7.9(10H, m). |
| 75-4 | (272)' | 79 | 169–175 (decomp.) | (CDCl$_3$—CD$_3$OD) 1.38(6H, d, J=7Hz), 2.37(3H, s), 3.0–4.5(6H, m), 4.67(2H, s), 6.68(2H, m), 7.22(2H, d, J=7Hz), 7.57(1H, d, J=8Hz), 7.76(2H, d, J=7Hz). |
| 75-5 | (277)' | 90 | Oil | 0.9–2.0(22H, m), 2.16(3H, s),3.05(6H, m), 4.02(2H, t, J=7Hz), 4.63(2H, s), 6.52(1H, d, J=2Hz), 6.64(1H, dd, J=2 and 8Hz), 7.18(2H, d, J=7Hz), 7.57(1H, d, J=8Hz), 7.78(2H, d, J=7Hz). |
| 75-6 | (278)' | 50 | Oil | 0.96(12H, d, J=7Hz), 1.4–3.5(17H, m), 4.16(2H, t, J=7Hz), 4.64(2H, s), 6.60(2H, m), 7.18(2H, d, J=7Hz), 7.58(1H, d, J=8Hz), 7.80(1H, d, J=8Hz). |
| 75-7 | (273)' | 92 | 186–190 | 1.44(9H, s), 2.36(3H, s), 3.23(2H, m), 4.08(2H, m), 4.60(2H, s), 4.68(1H, m), 6.50(1H, d, J=2Hz), 6.60(1H, dd, J=2 and 8Hz), 7.16(2H, d, J=7Hz), 7.52(1H, d, J=8Hz), 7.75(2H, d, J=7Hz). |
| 75-8 | (279)' | 85 | Oil | 1.08(6H, d, J=7Hz), 1.18(3H, t, J=7Hz), 2.2–4.2(18H, m), 4.62(2H, s), 6.56(2H, m), 7.16(2H, d, J=7Hz), 7.56(1H, d, J=8Hz), 7.76(2H, d, J=7Hz). |
| 75-9 | (280)' | 90 | Oil | 0.97(3H, t, J=7Hz), 1.21(9H, m), 1.5–4.5(15H, m), 4.62(2H, s), 6.60(2H, m), 7.16(2H, d, J=7Hz), 7.56(1H, d, J=8Hz), 7.76(2H, d, J=7Hz). |
| 75-10 | (281)' | 90 | Oil | 1.00(3H, t, J=7Hz), 1.25(3H, t, J=7Hz), 1.80(2H, m), 2.35(3H, s), 2.40(2H, m), 2.80–3.60(8H, m), 4.10(2H, t, J=7Hz), 4.14(2H, q, J=7Hz), 4.60(2H, s), 6.55(2H, m), 7.14(2H, d, J=7Hz), 7.52(1H, d, J=8Hz), 7.72(2H, d, J=7Hz). |
| 75-11 | (282)' | 90 | 52–60 | 0.99(3H, t, J=7Hz), 1.50(9H, s), 1.80(2H, m), 2.35(5H, m), 3.40(4H, m), 4.07(4H, m), 4.60(2H, s), 6.54(2H, m), 7.14(2H, d, J=7Hz), 7.52(1H, d, J=8Hz), 7.74(2H, d, J=7Hz). |
| 75-12 | (283)' | 90 | Oil | 1.38(3H, t, J=7Hz), 2.0–4.5(19H, m) 4.62(2H, s), 4.96(1H, t, J=4Hz), 6.47(1H, d, J=2Hz), 6.57(1H, dd, J=2 and 8Hz), 7.16(2H, d, J=7Hz), 7.54(1H, d, J=8Hz), 7.76(2H, d, J=7Hz). |
| 75-13 | (284)' | 72 | 55–64 | (CDCl$_3$—CD$_3$OD) 2.2–4.3(18H, m) 4.66(2H, s), 6.60(2H, m), 7.1–7.5(6H, m), 7.56(1H, d, J=8Hz), 7.76(2H, d, J=7Hz). |
| 75-14 | (285)' | 90 | 185–190 | (CDCl$_3$—CD$_3$OD) 2.2–3.6(13H, m), 4.20(2H, m), 4.66(2H, s), 4.92(2H, s), 6.67(2H, m), 7.16(2H, d, J=7Hz), 7.35(2H, d, J=8Hz), 7.55(1H, d, J=8Hz), 7.72(2H, d, J=7Hz), 7.98(2H, d, J=8Hz). |

TABLE 7-continued

| Example No. | Compound No. | Yield (%) | Melting point (°C.) | $^1$H-NMR spectrum (CDCl$_3$ solution, δ ppm) |
|---|---|---|---|---|
| 75-15 | (982) | 85 | Oil | 0.95(6H, t, J=7Hz), 1.60(8H, m), 2.06(3H, s), 2.36(5H, m), 2.52(3H, s), 3.16(6H, m), 4.10(2H, t, J=7Hz), 6.60(1H, d, J=2Hz), 6.78(1H, dd, J=2 and 8Hz), 7.18(2H, d, J=7Hz), 7.76(2H, d, J=7Hz), 7.84(1H, d, J=8Hz). |
| 75-16 | (986) | 75 | Oil | 0.96(6H, t, J=7Hz), 1.52(8H, m), 2.36(3H, s), 2.44(2H, m), 2.50(3H, s), 3.16(6H, m), 4.14(2H, t, J=7Hz), 6.7-8.3(12, m) |

REFERENTIAL EXAMPLE 23

Production of 6-(2,3-epoxypropyloxy)coumaran-3-one of the following formula:

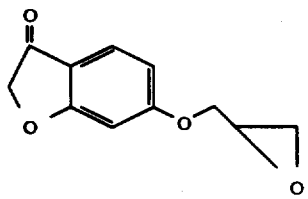

A mixture composed of 6.0 g (40 millimoles) of 6-hydroxycoumaran-3-one, 6.0 g (43 millimoles) of anhydrous potassium carbonate, 22.2 g (240 millimoles) of epichlorohydrin and 70 ml of DMF was stirred at 70° C. for 3 hours. The reaction mixture was cooled, and the solid was separated by filtration. DMF was evaporated from the filtrate. The residue was extracted by adding ethyl acetate and an aqueous solution of sodium hydroxide. The organic layer was washed with water, dried and concentrated under reduced pressure to give 7.4 g of a brown viscous oil. Ethyl acetate and ether (1:40) were added to the oil and the mixture was refluxed, and separated into a solution and a brown solid. The above mixed solvent was added to the solid, and the same operation was repeated three times. The solution was combined, and the mixture was concentrated under reduced pressure to give 5.9 g (yield 61%) of yellow crude crystals of the captioned compound. The crude crystals were recrystallized from ethyl acetate to form a final product.

Melting point: 107°-109° C.

$^1$H-NMR spectrum (CDCl$_3$ solution, δppm): 2.76(1H, dd, J=3 and 5 Hz), 2.94(1H, t, J=5 Hz), 3.38(1H, m), 4.00(1H, dd, J=7 and 10 Hz), 4.32(1H, dd, J=10 and 3 Hz), 4.63(2H, s), 6.58(1H, d, J=2 Hz), 6.68 (1H, dd, J=2 and 9 Hz), 7.58(1H, d, J=9 Hz).

EXAMPLE 76

Production of 6-[3-(N-ethyl-N-heptylamino)-2-hydroxypropyloxy]coumaran-3-one (compound No. 214):

2.24 g (9.23 millimoles) of 6-(2,3-epoxypropyloxy)-coumaran-3-one, 1.36 g 9.49 millimoles) of ethylheptylamine, 1.31 g (9.48 millimoles) of anhydrous potassium carbonate and 20 ml of acetonitrile were mixed and stirred at 77° C. for 12 hours. After cooling, the solid matter was removed by filtration and the filtrate was extracted by adding ethyl acetate and water. The organic layer was further extracted by adding 2N hydrochloric acid. The dark brown viscous matter in an oil-water interlayer and the aqueous layer were separated from the organic layer, and then extracted by adding ethyl acetate and a 6N aqueous solution of sodium hydroxide. The organic layer was dried and concentrated. The resulting reddish brown oil was dissolved in ether in a smallest required amount, and 2 to 3 times the weight of ether of hexane was gradually added. At this time, a dark reddish brown precipitate formed and adhered to the glass wall. The precipitate was again dissolved in ether, and hexane was added. This operation was repeated two or three times. The solutions were combined and concentrated to give 1.66 g of a yellowish oil. This oil was purified by silica gel column chromatography (eluted with ether), 1.11 g (yield 34%) of the captioned compound was obtained as a pale yellow oil.

$^1$H-NMR spectrum CDCl$_3$ solution, δppm): 0.88(3H, t, J=7 Hz), 1.03(3H, t, J=7 Hz), 1.0–1.6 10H, m), 2.60(6H, m), 3.95(1H, brs), 4.02(3H, m), 4.62(2H, s), 6.58 (1H, d, J=2 Hz), 6.67(1H, dd, J=2 and 9 Hz), 7.53(1H, d, J=9 Hz).

The compounds shown in Table 7' was obtained from the corresponding starting compounds in the same way as in Example 76.

TABLE 7'

| Example No. | Compound No. | Yield (%) | Melting point (°C.) | $^1$H-NMR spectrum (CDCl$_3$ solution, δ ppm) |
|---|---|---|---|---|
| 76-1 | (272) | 43 | — | 1.10(6H, d, J=7Hz), 2.4–4.1(6H, m), 4.63(2H, s), 6.57(1H, d, J=2Hz), 6.67(1H, dd, J=2 and 8Hz), 7.58(1H, d, J=8Hz) |
| 76-2 | (273) | 44 | — | 1.15(9H, s), 2.1–3.0(4H, m), 4.04(3H, m), 4.63(2H, s), 6.57(1H, d, J=2Hz), 6.67(1H, dd, J=2 and 8Hz), 7.57(1H, d, J=8Hz) |
| 76-3 | (274) | 54 | — | — |

EXAMPLE 77

Production of 6-[3-(N-ethyl-N-heptylamino)-2-hydroxypropyloxy]-coumaran-3-one p-toluenesulfonate (compound No. 216):

Anhydrous p-toluenesulfonic acid obtained by azeotropic dehydration of a toluene solution of 0.60 g (3.2 millimoles) of p-toluenesulfonic acid monohydrate was dissolved in ethyl acetate. The resulting solution was added to an ethyl acetate solution of 1.11 g (3.2 millimoles) of 6-[3-(N-ethyl-N-heptylamino)-2-hydroxypropyloxy]coumaran-3-one. While the mixed solution was stirred at room temperature, crystals were precipitated. The crystals were collected by filtration and dried under reduced pressure to give 1.15 g (yield 70%) of the captioned compound as pale yellow crystals.

Melting point: 120.9°-121.0° C.

REFERENTIAL EXAMPLE 24

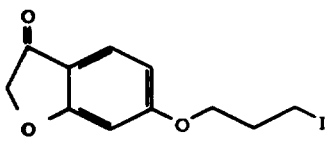

Twenty milliliters of DMF was added to 3.0 g (20 millimoles) of 6-hydroxycoumaran-3-one, 23.7 g (80 millimoles) of 1,3-diiodopropane and 5.52 g (40 millimoles) of potassium carbonate, and the mixture was stirred overnight at room temperature. The precipitate was separated by filtration, and DMF was evaporated under reduced pressure. The residue was purified by silica gel column chromatography (eluent: hexane/ethyl acetate = 7:3) to give 4.22 g (yield 66%) of the captioned compound as yellow crystals.

$^1$H-NMR spectrum (CDCl$_3$ solution, δppm): 2.32 (2H, quintet, J=6.3 Hz), 3.38 (2H, t, J=6.3 Hz), 4.14(2H, t, J=6 Hz), 4.64(2H, s), 6.5–6.8(2H, m), 7.58(1H, d, J=9 Hz).

EXAMPLE 78

Production of 6-3-(2-exo-norbornyl)aminopropyloxy]coumaran-3-one (compound No. 166):

Ten milliliters of acetonitrile was added to 0.954 g (3 millimoles) of 5-(3-iodopropyloxy)coumaran-3-one, 0.366 g (3.3 millimoles) of 2-exo-aminonorbornane and 0.690 g (5 millimoles) of potassium carbonate, and the mixture was stirred at room temperature for 4 hours. Acetonitrile was evaporated under reduced pressure, and the residue was purified by silica gel column chromatography (eluent: dichloromethane:methanol = 10:1). The product was further dissolved in hexane, and the insoluble matter was separated by filtration. Hexane was evaporated under reduced pressure to give 0.36 g of the captioned compound.

$^1$H-NMR spectrum CDCl$_3$ solution, δppm): 0.85–1.75(10H, m), 1.75–2.3(4H, m), 2.45–2.9(3H, m), 4.11(2H, t, J=6 Hz), 4.61(2H, s), 6.49–6.75(2H, m), 7.51(1H, d, J=9 Hz).

EXAMPLE 79

Production of 6-3-(2-exo-norbornyl)aminopropyloxy]coumaran-3-one p-toluenesulfonate (compound No. 168):

6- 3-(2-exo-norbornyl)aminopropyloxy)coumaran-3-one (0.6 millimole) was dissolved in ethanol, and an ethanol solution of 0.075 g (0.6 millimole) of ptoluenesulfonic acid monohydrate was added. Ethanol was evaporated under reduced pressure to give 0.24 g of the captioned compound as yellow crystals. The yield was quantitative.

Melting point: 118°–124° C.

EXAMPLE 80

Production of 6-3-(N-ethyl-N-heptylamino)propyloxy]3-hydroxycoumaran (compound No. 450):

0.5 g (1.5 millimoles) of 6-3-(N-ethyl-N-heptylamino)propyloxy]coumaran-3-one, 0.15 g (3.6 millimoles) of sodium borohydride and 10 ml of ethanol were stirred at room temperature for 3 hours. The solvent was evaporated under reduced pressure, and the residue was extracted by adding water and dichloromethane. The dichloromethane layer was washed with water, dried over sodium sulfate and concentrated to give 0.41 g (yield 80%) of the desired compound as an oil.

$^1$H-NMR spectrum (CDCl$_3$ solution, δppm): 0.88(3H, m), 1.01(3H, t, J=7.2 Hz), 1.30 (6H, m), 1.82(4H, m), 2.50(6H, m), 3.99 (2H, t, J=5 Hz), 4.50(2H, m), 5.30(1H, m), 6.45(1H, s), 6.50(1H, dd, J=2 and 9 Hz), 7.29(1H, d, J=9 Hz).

EXAMPLE 81

Production of 5-3-(N-ethylheptylamino)propyloxy]-1-hydroxyindane (compound No. 500.):

By using 5-3-(N-ethylheptylamino)propyloxy]indanone instead of 6-3-(N-ethylheptylamino)propyloxy]-coumaran-3-one, 5-[3-(N-ethylheptylamino)propyloxy]-1-hydroxyindane was obtained in the same way as an oil.

$^1$H-NMR spectrum (CDCl$_3$ solution, δppm): 0.89(3H, t, J=7 Hz), 1.03(3H, t, J=7 Hz), 1.2–2.2(12H, m), 2.3–3.1(8H, m), 3.72 (2H, q, J=7 Hz), 4.00(2H, t, J=7 Hz), 5.18 (1H, m), 6.80(2H, m), 7.30(1H, d, J=9 Hz).

EXAMPLE 82

Production of (3-oxo-6-coumaranoxypropyl)diethylheptyl ammonium bromide (compound No. 286):

A solution composed of 2.7 g (8.1 millimoles) of 3-(N-ethyl-N-heptylamino)propyloxycoumaran-3-one, 12 g of ethyl bromide and 40 ml of acetonitrile were refluxed for 8 hours. Then, the solvent was evaporated under reduced pressure. The residue was purified by silica gel column chromatography (CH$_2$Cl/CH$_3$OH=95-90/5-10) to give 2.8 g (yield 78%) of the desired compound.

Melting point: 106°–108° C.

$^1$H-NMR spectrum (CDCl$_3$ solution,δppm): 0.90(3H, t, J=5 Hz), 1.2–1.8(16H, m), 2.45 (2H, m), 3.3–3.8(8H, m), 4.30(2H, t, J=5 Hz), 4.63(2H, s), 6.58(1H, d, J=2 Hz), 6.63(1H, dd, J=2.9 Hz), 7.56(1H, d, J=9 Hz).

EXAMPLES 83 TO 102

In the same way as in Example 82, the compounds given in Table 8 were produced from the corresponding starting compounds.

TABLE 8

| Example No. | Compound No. | Yield (%) | Melting point (°C.) | $^1$H-NMR spectrum (CDCl$_3$ solution, δ ppm) |
|---|---|---|---|---|
| 83 | (287) | 35 | 145–149 (decomp.) | 0.88(3H, m), 1.2–1.9(16H, m), 2.16(3H, s), 2.45(2H, m), 3.3–3.9(8H, m), 4.30(2H, t, J=5Hz), 4.60(2H, s), 6.56(1H, s), 7.38(1H, s). |
| 84 | (288) | 48 | 47–50 | 0.88(3H, m), 1.46(16H, m), 2.44(2H, m), 2.52(3H, s), 3.3–3.8(8H, m), 4.26(2H, t, J=5Hz), 4.56(2H, s), 6.37(2H, s). |
| 85 | (289) | 72 | 66–70 | 0.88(3H, t, J=5Hz), 1.46(16H, m), 2.44(2H, m), 3.26–3.82(8H, m), 3.98(3H, s), 4.32(2H, t, J=5Hz), 4.66(2H, s), 6.74(1H, d, J=9Hz), 7.38(1H, d, J=9Hz). |

TABLE 8-continued

| Example No. | Compound No. | Yield (%) | Melting point (°C.) | $^1$H-NMR spectrum (CDCl$_3$ solution, δ ppm) |
|---|---|---|---|---|
| 86 | (291) | 59 | 142–144 (decomp.) | 0.90(3H, m), 1.48(16H, m), 2.52(2H, m), 3.58(8H, m), 4.40(2H, t, J=5Hz), 4.66(2H, s), 6.74(1H, s), 7.64(1H, s). |
| 87 | (293) | 52 | 103–107 | 0.9–2.0(21H, m), 2.44(2H, m), 3.2–4.0(8H, m), 4.30(2H, t, J=5Hz), 4.62(2H,s), 6.56(1H, d, J=2Hz), 6.60(1H, dd, J=2.9Hz) 7.56(1H, d, J=9Hz). |
| 88 | (470) | 91 | 110–114 | 0.90(3H, m), 1.38(18H, m), 1.70(2H, m), 2.24(2H, m), 3.42(7H, m), 4.05(2H, m), 4.50(2H, m), 5.35(1H, m), 6.38(1H, s), 6.40(1H, dd, J=9Hz), 7.38(1H, d, J=9Hz). |
| 89 | (634) | 87 | 51–61 | 0.68(3H, t, J=5Hz), 0.9–1.8(15H, m), 1.94(3H, s), 2.13(6H, m), 3.0–3.7(8H, m), 4.10(2H, t, J=5Hz), 6.56(1H, d, J=2Hz), 6.62(1H, dd, J=2 and 9Hz), 7.24(1H, d, J=9Hz). |
| 90 | (820) | 55 | 64–69 | 0.89(3H, t, J=5Hz), 0.98(3H, t, J=7Hz), 1.1.–2.7(25H, H, m), 3.2–3.8(8H, m), 4.20(2H, t, J=5Hz), 6.36(1H, d, J=2Hz), 6.48(1H, dd, J=2 and 9Hz), 7.76(1H, d, J=9Hz). |
| 91 | (870) | 70 | 63–72 | 0.88(3H, t, J=5Hz), 1.1–2.0(22H, m), 2.34(2H, m), 2.58(2H, s), 3.60(8H, s), 4.16(2H, t, J=5Hz), 6.84(3H, m). |
| 92 | (720) | 42 | 108–112 | 0.90(3H, t, J=5Hz), 1.02(3H, t, J=7Hz), 1.1–2.5(23H, m), 3.2–3.8(1H, m), 4.07(2H, t, J=5Hz), 6.2–6.8(3H, m). |
| 93 | (420) | 70 | 102–106 | 0.9(3H, t, J=5Hz),1.0(3H, t, J=7Hz). 1.1–2.0(24H, m), 2.3(2H, m), 3.0–3.8(9H, m), 4.10(2H, t, J=5Hz), 6.30(1H, d, J=2Hz), 6.36(1H, dd, J=2 and 9Hz), 6.96(1H, d, J=9Hz). |
| 94 | (636) | 70 | 91–93 | 0.88(3H, t, J=5Hz), 1.2–2.0(22H, m), 2.45(5H, m), 3.2–3.9(9H, m), 4.3(2H,t, J=5Hz), 6.76(1H, d, J=2Hz), 6.80(1H, dd, J=2 and 9Hz), 7.49(1H, d, J=9Hz). |
| 95 | (770) | 82 | 67–79 | 0.88(3H, t, J=5Hz), 1.1–2.5(20H, m), 2.85(4H, m), 3.2–3.8(8H, m), 4.10(2H, t, J=5Hz), 6.65(1H, dd, J=2 and 9Hz), 6.75(1H, d, J=2Hz), 7.10(1H, d, J=9Hz). |
| 96 | (920) | 67 | 51–56 | 0.90(3H, t, J=5Hz), 1.2–2.8(28H, m), 3.2–3.8(8H, m), 4.08(2H, t, J=5Hz), 6.32(1H, d, J=2Hz), 6.36(1H, dd, J=2 and 9Hz), 6.96(1H, d, J=9Hz). |
| 97 | (638) | 98 | 154–158 | 0.89(3H, t, J=5Hz), 1.1–2.0(16H, m), 3.46(2H, m), 3.3–3.9(8H, m), 4.32(2H, t, J=5Hz), 6.26(1H, d, J=11Hz), 6.81(1H, d, J=2Hz), 6.86(1H, dd, J=2 and 9Hz), 7.38(1H, d, J=9Hz), 7.66(1H, d, J=11 Hz). |
| 98 | (722) | 67 | 74–81 | 0.90(3H, t, J=5Hz), 1.1–2.0(16H, m), 2.3(2H, m), 3.1–3.8(8H, m), 4.10(2H, t, J=5Hz), 5.93(2H, s), 6.30(1H, dd, J=2 and 7Hz), 6.47(1H, d, J=2Hz), 6.70(1H, d, J=7Hz). |
| 99 | (422) | 85 | 117–119 | 0.90(3H, t, J=5Hz), 1.1–2.0(18H, m), 2.34(2H, m), 3.14(2H, t, J=7Hz), 3.2–3.8(6H, m), 4.10(2H, t, J=5Hz), 4.58(2H, t, J=7Hz), 6.34(1H, d, J=2Hz), 6.38(1H, dd, J=2 and 9Hz), 7.07(1H, d, J=9Hz). |
| 100 | (320) | 67 | 70–80 | 0.90(3H, t, J=5Hz), 1.1–2.2(20H, m), 2.2–2.8(10H, m), 4.30(2H, t, J=5Hz), 6.88(1H, dd, J=2 and 9Hz), 6.94(1H, d, J=2Hz), 7.66(1H, d, J=9Hz). |
| 101 | (294) | 58 | 142–146 | 1.0–2.2(9H, m), 2,44(6H, m), 3.70(5H, m), 4.30(4H, m), 4.62(2H, s), 5.6–6.2(3H, m), 6.60(1H, d, J=2Hz), 6.65(1H, dd, J=2 and 9Hz), 7.54(1H, d, J=9Hz). |
| 102 | (1024) | 91 | 139–141 | 0.88(3H, t, J=5Hz), 1.2–1.9(22H, m), 2.36(1H, m), 3.2–3.8(8H, m), 4.12(2H, t, J=5Hz), 6.7–7.4(9H, m). |

REFERENTIAL EXAMPLE 25

Production of 3-hydroxyphthalimide:

3.64 g (0.02 mole) of 3-hydroxyphthalic acid and 5.61 g (0.04 mole) of 25% aqueous ammonia were charged into a 50 ml SUS 314 stainless steel autoclave, and reacted with stirring at 190° C. for 6 hours. The reaction mixture was gradually cooled to room temperature, and then adjusted to pH 2 with concentrated hydrochloric acid. The crystals which precipitated were collected by suction-filtration and then dried in vacuum to give 1.45 g (yield 45%) of the desired compound.

$^1$H-NMR spectrum (CDCl$_3$, δpm):
6.9–7.5(m, 3H), 3.6–4.2(br, 2H).

REFERENTIAL EXAMPLE 26

Production of 3-(3-iodopropyloxy)phthalimide:

1.30 g (0.0080 mole) of 3-hydroxyphthalimide, 9.57 g (0.0319 mole) of 1,3-diiodopropane, 1.65 g (0.0120 mole) of potassium carbonate and 30 ml of dimethylformamide were charged into a 100 ml Pyrex round-bottomed flask, and reacted with stirring at room temperature and atmospheric pressure for 5 hours under nitrogen. The reaction mixture was applied to a rotary evaporator to evaporate the solvent. The residue was purified by silica gel column chromatography eluent:hexane/ethyl acetate=5/1 (v/v)] to give 1.24 g (yield 49%) of the desired compound.

$^1$H-NMR spectrum (CDCl$_3$, δppm): 7.0–7.8(m, 3H), 5.7(br, 1H), 4.40(t, 2H, J=7 Hz), 3.28(t, 2H, J=7 Hz), 2.30(tt, 2H, J=2, 7 Hz).

EXAMPLE 103

Production of 3-3-(N,N-di-n-butylamino)propyloxy]phthalimide (compound No. 940):

0.72 g (0.0022 mole) of 3-(3-iodopropyloxy)phthalimide, 0.36 g (0.0028 mole) of di-n-butylamine, 0.45 g (0.0032 mole) of potassium carbonate and 15 ml of acetonitrile were charged into a 100 ml Pyrex round-bottomed flask, and reacted under reflux under atmospheric pressure for 4 hours under nitrogen. The reaction mixture was cooled gradually to room temperature, and concentrated by a rotary evaporator. The residue was purified by silica gel column chromatography [eluent: dichloromethane/methanol=10/1 (v/v)] to give 3-0.52 g (yield 73%) of the desired compound.

$^1$H-NMR spectrum (CDCl$_3$ solution, δppm): 7.0–7.6(m, 3H), 4.36(t, 2H, J=7 Hz), 2.4–3.0(m, 6H), 1.8–2.2(m, 2H), 1.1–1.8 (m, 8H), 0.92(t, 6H, J=6 Hz).

EXAMPLE 104

In the same way as in Example 103, compound No. 942 was obtained in a yield of 43%.

$^1$H-NMR spectrum (CDCl$_3$ solution,δppm): 7.84(d, 1H, J=7 Hz , 7.3–7.6(m, 5H), 7.24 (dd, 2H J=2, 7 Hz), 4.17(t, 2H, J=7 Hz), 2.2–2.7(m, 6H), 1.93(m, 2H), 1.1–1.7(ml, 8H), 0.89(t, 6H, J=5 Hz).

EXAMPLE 105

Production of compound No. 1196:

A mixture composed of 4.4 g (31.9 millimoles) of 6-hydroxycoumaran-3-one, 5.5 g (27.3 millimoles) of the compound produced in Referential Example 13, 4.8 g (34.8 millimoles) of potassium carbonate and 120 ml of toluene was refluxed for 30 hours. After cooling, the solid was separated by filtration and concentrated. The residue was purified by silica gel column chromatography (CH$_2$Cl$_2$/MeOH=95/5) to give the desired compound as an oil in a yield of 42%.

$^1$H-NMR spectrum (CDCl$_3$ solution, δppm): 1.70(12H, m), 2.56 6H, m), 4.15(2H, t, J=7 Hz), 4.64(2H, s), 6.58(1H, d, J=2 Hz), 6.65(1H, dd, J=2 and 9 Hz), 7.57(1H, d, J=9 Hz).

EXAMPLES 106 TO 129

The compounds indicated in Table 9 were produced from the corresponding starting compounds in the same way as in Example 105.

TABLE 9

| Example No. | Compound No. | Yield (%) | Melting point (°C.) | $^1$H-NMR spectrum (CDCl$_3$ solution, δ ppm) |
|---|---|---|---|---|
| 106 | (1164) | 66 | — | 2.00(2H, m), 2.48(6H, m), 3.74(4H, m), 4.12(2H, t, J=7Hz), 4.64(2H, s), 6.58(1H, d, J=2Hz), 6.64(1H, fdd, J=2 and 9Hz), 7.58(1H, d, J=9Hz) |
| 107 | (1108) | 77 | Oil | 1.5–1.8(6H, m), 2.0–2.2(2H, m), 2.7–3.5(6H, m), 4.03(2H, t, J=7Hz) |
| 108 | (1188) | 59 | Oil | 1.6–2.7(10H, m), 2.2–2.8(6H, m), 4.20(2H, t, J=7Hz), 4.66(2H, s), 6.6(2H, m), 7.50(1H, d, J=8Hz) |
| 109 | (1136) | 62 | — | 1.8–2.2(7H, m), 2.6–3.9(6H, m), 4.18(2H, t, J=7Hz), 4.70(2H, s), 6.6–7.2(11H, m), 7.58(1H, d, J=8Hz) |
| 110 | (1184) | 53 | 178–182 | 2.08(2H, q, J=7Hz), 2.53(4H, m), 2.59(2H, t, J=7Hz), 3.20(3H, s), 3.43(2H, s), 3.86(4H, m), 4.15(2H, t, J=7Hz),4.63(2H, s), 6.59(1H, s), 6.64(1H, d, J=9Hz), 7.57(1H, d, J=9Hz), 7.92(1H, s) |
| 111 | (1100) | 25 | — | 1.7–2.3(6H, m), 2.65(6H, m), 4.14(2H, t, J=7Hz), 4.64(2H, s), 6.58(1H, s), 6.66(1H, dd, J=2 and 8Hz), 7.57(1H, d, J=8Hz) |
| 112 | (1104) | 20 | — | 7.50(d, 1H, 7Hz), 6.5–6.8(m, 2H),4.58(s, 2H), 4.16(t, 2H, 7Hz), 2.8–3.6(m, 6H), 2.0–2.6(m, 5H), 1.05(d, 3H, 7Hz) |
| 113 | (1112) | 30 | — | 7.54(d, 1H, 7Hz), 6.5–6.7(2H, 4.6(s, 2H), 4.08(t, 2H, 7Hz), 1.9–3.0(m, 7H), 1.3–1.8(6H), 1.08(d, 3H, 7Hz) |
| 114 | (1116) | 22 | — | 7.52(d, 1H, 7Hz), 6.5–6.7(2H, m), 4.50(s, 2H), 4.03(t, 2H, 7Hz), 2.7–3.6(6H, m),1.3–2.6(m, 7H), 0.83(s, 3H) |
| 115 | (1120) | 88 | — | 7.55(d, 1H, 7Hz), 6.5–6.7(2H, m), 4.60(s, 2H), 4.09(t, 2H, 7Hz) 2.90(t, 2H, 7Hz), 2.4–2.6(4H), 1.2–2.0(7H, m), 0.90(d, 3H, 7Hz) |
| 116 | (1124) | 28 | — | 7.51(d, 1H, 7Hz), 6.4–6.7(2H), 4.60(s, 2H), 4.04(t, 2H, 7Hz), 3.0(t, 2H, 7Hz), 2.4–2.8(2H), 1.9–2.1(2H), 1.3–1.8(6H) 1.20(d, 6H, 7Hz) |
| 117 | (1128) | 46 | — | 7.56(d, 1H, 7Hz), 6.5–6.7(2H, m), 4.61(s, 2H), 4.10(t, 2H, 7Hz), 2.2–2.6(6H, m), 1.6–2.2(4H, m), 1.28(dd, 2H, 7Hz), 0.95(d, 6H, 7Hz) |
| 118 | (1132) | 50 | — | 0.90(3H, t, J=7Hz), 1.1–3.1(17H, m), 4.10(2H, t, J=7Hz), 4.63(2H, s), 6.56(1H, s), 6.64(1H, dd, J=2 and 8Hz), 7.56(1H, d, J=8Hz) |
| 119 | (1144) | 82 | — | 7.55(d, 1H, 7Hz), 6.5–6.7(2H), 7.1–7.3(5H, m), 4.60(s, 2H), 4.08(t, 2H, 7Hz),2.90(t, 2H, 7Hz), 2.4–2.6(4H), 1.3–2.1(m, 9H) |
| 120 | (1148) | 64 | — | 7.0–7.7(m, 6H), 6.4–6.8(m, 2H), 4.60(s, 2H), 4.16(t, 2H, 7Hz), 2.7–3.0(m, 7H), 1.7–2.2(m, 6H) |
| 121 | (1152) | 48 | 150–153 | 7.2–7.6(m, 5H), 6.6–6.8(m, 2H), 4.56(5.2H), 4.16(t, 2H, 7Hz), 3.0–3.7(m, 7H), 1.7–2.6(m, 6H) |
| 122 | (1156) | 63 | — | 1.0–3.2(20H, m), 4.12(2H, t, J=7Hz),4.63(2H, s), 6.57(1H, s), 6.63(1H, dd, J=2 and 8Hz), 7.56(1H, d, J=8Hz) |
| 123 | (1160) | 20 | — | 7.52(d, 1H, 7Hz), 7.0–7.5(m, 4H), 6.6–6.8(m, 2H), 4.58(s, 2H), 4.58(s, 2H), 4.19(t, 2H, 7Hz), 2.7–3.3(m, 6H), 1.9–2.4(m, 4H) |
| 124 | (1168) | 26 | — | 1.25(6H, d, J=7Hz), 1.8–2.6(8H, m), 3.8–4.3(4H, m), 4.62(2H, s), 6.56(1H, s), 6.64(1H, dd, J=2 and 8Hz), 7.56(1H,d, J=8Hz) |
| 125 | (1172) | 64 | — | 1.97(2H, m), 2.56(2H, t, 7Hz), 2.74(8H, m), 4.09(2H, t, J=7Hz), 4.63(2H, s), 6.56(1H, s), 6.62(1H, dd, J=2 and 8Hz), 7.56(1H, d, J=8Hz) |
| 126 | (1176) | 52 | — | 7.53(d, 1H, 7Hz), 6.6–6.8(m, 2H), 4.60(s, 2H), 4.12(t, 2H, 7Hz) |
| 127 | (1180) | 69 | — | 7.55(d, 1H, 7Hz), 7.3–7.5(5H, m), 6.6–6.8(m, 2H), 4.43(s, 2H), 4.08(t, 2H, 7Hz), 2.8–3.5(m, 12H), 2.2–2.4(m, 2H) |
| 128 | (1192) | 37 | — | 0.88(3H, d, J=7Hz), 0.94(3H, d, J=7Hz), 1.1–2.9(14H, m), 4.12(2H, t, J=7Hz), 4.62(2H, s), 6.56(1H, s), 6.62(1H, dd, J=2 and 8Hz), 7.56(1H, d, J=8Hz) |
| 129 | (1129) | 75 | — | 7.55(d, 1H, 7Hz), 6.5–6.8(m, 2H), 4.60(s, 2H), 4.10(t, 2H, 7Hz), 2.3–3.0(6H, m), 1.2–2.2(6H, m), 0.87(d, 6H, 7Hz) |
| 129-1 | (1272) | 44 | Oil | δ7.55(d, 1H, J=9Hz), δ6.5–6.7(m, 2H), δ4.62(s, 2H), δ4.10(t, 2H, J=7Hz), δ2.8–3.1(m, 4H), δ2.4–2.8(m, 4H), δ1.1–2.2(m, 7H), δ0.90(t, 3H, J=6Hz) |
| 129-2 | (1276) | 52 | 171–175 | δ7.55(d, 1H, J=9Hz), δ6.6–6.8(m, 2H), δ4.62(s, 2H), δ4.16(t, 2H, J=7Hz), δ3.2–3.5(m, 2H), δ3.72(t, 2H, J=7Hz), δ1.2–2.8(m, 10H), δ0.92(d, 6H, J=7Hz) |
| 129-3 | (1280) | 82 | Oil | δ7.56(d, 1H, J=9Hz), δ6.6–6.8(m, 2H), δ4.72(s, 2H), δ4.12(t, 2H, J=7Hz), δ4.15(q, 2H, J=7Hz), δ3.70(t, 2H, J=7Hz), δ2.5–3.2(m, 4H), δ1.6–2.4(m, 7H), 1.24(t, 3H, J=7Hz) |

TABLE 9-continued

| Example No. | Compound No. | Yield (%) | Melting point (°C.) | 1H-NMR spectrum (CDCl3 solution, δ ppm) |
|---|---|---|---|---|
| 129-4 | (1284) | 51 | 148-153 | δ7.54(d, 1H, J=9Hz), δ6.5-6.7(m, 2H), δ6.0(br, 1H), δ4.62(s, 2H), δ4.09(t, 2H, J=7Hz), δ2.96(s, 3H), δ1.5-3.5(m, 13H) |
| 129-5 | (1288) | 28 | 96-98 | δ7.63(d, 1H, J=9Hz), δ6.6-6.8(m, 2H), δ4.68(s, 2H), δ4.14(t, 2H, J=7Hz), δ3.4-3.8(m, 2H), δ2.8-3.2(m, 2H), δ2.4-2.8(m, 3H), δ1.8-2.3(m, 4H), δ1.2-1.8(m, 5H) |
| 129-6 | (1292) | 7 | Oil | 1.10(3H, t, J=7Hz), 1.18(3H, t, J=7Hz), 1.4-3.1(13H, m), 3.36(4H, q, J=7Hz), 4.09(2H, t, J=7Hz), 4.62(2H, s), 6.55(1H, d, J=2Hz), 6.65(1H, dd, J=2 and 8Hz), 7.55(1H, d, J=8Hz) |
| 129-7 | (1296) | 39 | Oil | 1.73(4H, m), 1.97(2H, m), 2.54(6H, m), 3.94(4H, s), 4.07(2H, t, J=7Hz), 4.58(2H, s), 6.58(2H, m), 7.49(1H, d, J=8Hz) |
| 129-8 | (1300) | 48 | Oil | δ7.55(d, 1H, J=9Hz), δ6.5-6.7(m, 2H), δ4.60(s, 2H), δ4.17(t, 2H, J=7Hz), δ3.70(t, 2H, J=7Hz), δ2.8-3.3(m, 3H), δ2.2-2.7(m, 6H), δ2.10(dt, 2H, J=7, 7Hz), δ2.06(2, 3H), δ4.9(br, 1H) |
| 129-9 | (1302) | 23 | 116-120 | δ8.20(d, 2H, J=9Hz), δ7.62(d, 1H, J=9Hz), δ7.43(d, 2H, J=9Hz), δ6.5-6.8(m, 2H), δ4.64(s, 2H), δ4.22(t, 2H, J=7Hz), δ3.6-4.0(m, 2H), δ3.2-3.6(m, 3H), δ3.02(s, 3H), δ1.7-2.8(m, 9H), δ13.0(br, 1H) |
| 129-10 | (1308) | 70 | 180-182 | δ7.54(d, 1H, J=9Hz), δ7.2-7.4(m, 5H), δ6.6-6.8(m, 2H), δ4.63(s, 2H), δ4.50(t, 2H, J=5Hz), δ3.3-3.8(m, 6H), δ1.8-3.0(m, 5H) |
| 129-11 | (1312) | 55 | — | 1.4-2.6(15H, m), 3.08(2H, m), 4.04(2H, t, J=7Hz), 4.62(2H, s), 6.53(1H, d, J=2Hz), 6.63(1H, dd, J=2 and 8Hz), 7.27(5H, m), 7.56(1H, d, J=8Hz) |
| 129-12 | (1316) | 57 | — | 1.3-2.4(17H, m), 3.07(2H, m), 4.02(2H, t, J=7Hz), 4.62(2H, s), 6.53(1H, d, J=2Hz), 6.63(1H, dd, J=2 and 8Hz), 7.26(5H, m), 7.55(1H, d, J=8Hz) |
| 129-13 | (1320) | 60 | — | 1.1-3.4(13H, m), 4.05(3H, m), 4.62(2H, s), 6.58(1H, d, J=2Hz), 6.68(1H, dd, J=2 and 8Hz), 7.24(5H, m), 7.55(1H, d, J=8Hz) |
| 129-14 | (1324) | 95 | — | 2.3-4.1(13H, m), 4.20(1H, s), 4.58(2H, s), 6.53(1H, d, J=2Hz), 6.63(1H, dd, J=2 and 8Hz), 7.27(9H, m), 7.52(1H, d, J=8Hz) |
| 129-15 | (1328) | 68 | Oil | δ7.0-7.6(m, 1H), δ6.7-6.9(m, 2H), δ6.21(s, 1H), δ4.09(t, 2H, J=7Hz), δ2.9-3.1(m, 2H), δ2.5-2.8(m, 4H), δ1.1-2.2(m, 9H) |
| 129-16 | (1332) | 89 | Oil | δ7.0-7.6(m, 8H), δ4.32(t, 2H, J=7Hz), δ2.9-3.2(m, 4H), δ2.4-2.7(m, 3H), δ1.2-2.3(m, 8H) |
| 129-17 | (1336) | 79 | Oil | δ7.73(d, 1H, J=7Hz), δ7.0-7.4(m, 7H), δ4.12(t, 2H, J=7Hz), δ3.16(s, 3H), δ2.7-3.2(m, 2H), δ1.0-2.7(m, 13H) |
| 129-18 | (1340) | 85 | Oil | δ7.73(d, 1H, J=7Hz), δ7.1-7.4(m, 5H), δ6.4-6.6(m, 2H), δ4.14(t, 2H, J=7Hz), δ3.90(s, 3H), δ2.56(s, 3H), δ1.8-3.6(m, 15H) |
| 129-19 | (1344) | 69 | 66-70 | δ7.62(d, 1H, J=9Hz), δ7.0-7.4(m, 5H), δ6.4-6.7(m, 2H), δ7.94(s, 1H), δ4.22(t, 2H, J=7Hz), δ3.2-3.6(m, 2H), δ2.9-5.2(m, 2H), δ1.6-2.8(m, 11H), δ2.04(s, 3H) |

EXAMPLE 130

Production of compound No. 1198:

Two grams (10 millimoles) of compound No. 1196 was dissolved in 30 ml of acetonitrile, and 1.0 9 (10.2 millimoles) of concentrated hydrochloric acid was added. The mixture was stirred for 0.5 hour. Then, under reduced pressure, the solvent was evaporated. The residue was crystallized from ethyl acetate/ether to give the desired compound in a yield of 29%.

Melting point: 258°-260° C.

1H-NMR spectrum CDCl3 solution, δppm): 1.8-3.8(18H, m), 4.17(2H, t, J=5 Hz), 4.64(2H, s), 6.60(1H, d, J=2 Hz), 6.64(1H, dd, J=2 and 9 Hz), 7.52(1H, d, J=9 Hz).

EXAMPLES 131 TO 149

The compounds indicated in Table 10 were produced from the corresponding starting compounds in the same way as in Example 130.

TABLE 10

| Example No. | Compound No. | Yield (%) | Melting point (°C.) | 1H-NMR spectrum (CDCl3 solution, δ ppm) |
|---|---|---|---|---|
| 131 | (1110) | 81 | 147-151 | 1.8-2.0(6H, m), 2.1-2.3(2H, m), 2.8-3.6(6H, m), 4.27(2H, t, J=7Hz), 4.80(2H, s), 6.83(1H, dd, J=5 and 8Hz), 6.9(1H, d, J=5Hz), 7.62(1H, d, J=8Hz), 10.3(1H, br, s) |
| 132 | (1186) | 76 | >300 | 2.33(2H, br, s), 3.14(3H, s), 3.28(6H, m), 3.56(2H, s), 3.76(4H, m), 4.24(2H, t, J=7Hz), 4.75(2H, s), 6.71(1H, d, J=9Hz), 6.80(1H, s), 7.53(1H, d, J=9Hz) |
| 133 | (1114) | 95 | 170-173 | 7.58(d, 1H, 7Hz), 6.5-6.8(2H), 4.62(s, 2H), 4.20(t, 2H, 7Hz), 3.4-3.6(m, 2H), 2.8-3.3(m, 2H), 1.2-2.6(m, 9H), 1.58(d, 3H, 7Hz) |
| 134 | (1118) | 88 | 183-184 | 7.58(d, 1H, 7Hz), 6.4-6.8(2H), 4.55(s, 2H), 4.10(t, 2H, 7Hz), 3.0-3.8(6H), 1.0-3.0(m, 7H), 0.85(d, 3H, 7Hz), 11.2(br, 1H) |
| 135 | (1122) | 85 | 204-207 | 7.57(d, 1H, 7Hz), 6.5-6.7(2H), 4.61(s, 2H), 4.8(t, 2H, 7Hz), 3.5-3.8(m, 2H), 3.0-3.4(m, 2H), 2.4-2.8(m, 2H), 1.6-2.2(7H, br), 1.05(d, 3H, 7Hz), 12.4(br, 1H) |
| 136 | (1126) | 93 | 183-187 | 7.59(d, 1H, 7Hz), 6.6-6.8(2H), 4.70(s, 2H), 4.20(t, 2H, 7Hz), 2.9-4.0(4H), 1.9-2.2(2H), 1.5-2.0(6H), 1.4(d, 6H, 7Hz), 10.4(br, 1H) |
| 137 | (1130) | 90 | 206-209 | 7.56(d, 1H, 7Hz), 6.6-6.8(m, 2H), 4.62(m, 2H), 4.20(t, 2H, 7Hz), 3.1-3.5(m, 2H), 2.2-2.7(m, 8H), 1.8-2.0(2H), 1.00(d, 6H, 7Hz) |
| 138 | (1131) | 86 | 166-169 | 7.48(d, 1H, 7Hz), 6.5-6.7(2H, m), 4.60(s, 2H), 4.13(t, 2H, 7Hz), 2.2-2.6(m, 6H), 1.3-1.8(m, 6H), 1.36(d, 2H, 7Hz), 0.93(d, 3H, 7Hz), 11.4(br, 1H) |
| 139 | (1134) | 71 | 112-116 | 0.96(3H, t, J=7Hz), 1.2-3.8(17H), 4.20(2H, m), 4.63(2H, s), 6.56(1H, s), 6.62(1H, dd, J=2 and 8Hz), 7.55(1H, d, J=8Hz) |

TABLE 10-continued

| Example No. | Compound No. | Yield (%) | Melting point (°C.) | $^1$H-NMR spectrum (CDCl$_3$ solution, δ ppm) |
|---|---|---|---|---|
| 140 | (1138) | 86 | 222-223 | Same to Compound No. 1139 |
| 141 | (1146) | 81 | 199-203 | 7.57(d, 1H, 7Hz), 7.0-7.4(5H), 6.5-6.7(2H, m), 4.61(s, 2H), 4.18(t, 2H, 7Hz), 3.0-3.4(m, 2H), 2.3-2.8(m, 4H), 1.7-2.2(br, 9H), 12.4(br, 1H) |
| 142 | (1150) | 90 | 228-233 | 7.1-7.7(m, 6H), 6.4-6.8(m, 2H), 4.61(s, 2H), 4.20(t, 2H, 7Hz), 2.9-3.6(m, 9H), 2.4-2.6(m, 2H), 1.6-2.1(br, 4H) |
| 143 | (1154) | 83 | 203-206 | 7.2-7.7(m, 5H), 6.6-6.8(m, 2H), 4.66(s, 2H), 4.24(t, 2H, 7Hz), 3.2-3.8(m, 7H), 1.8-2.8(m, 6H), 12.5(br, 1H) |
| 144 | (1158) | 70 | 138-144 | 1.2-3.8(20H), 4.20(2H, t, J=7Hz), 4.64(2H, s), 6.56(1H, s), 6.63(1H, dd, J=2 and 9Hz), 7.58(1H, d, J=9Hz) |
| 145 | (1162) | 85 | 209-213 | 7.55(d, 1H, 7Hz), 7.1-7.5(m, 4H), 6.6-6.8(m, 2H), 4.62(s, 2H), 4.23(t, 2H, 7Hz),3.0-3.8(m, 6H), 2.3-2.8(m, 4H), 11.3(br, 1H) |
| 146 | (1178) | 86 | 242-245 | 7.55(d, 1H, 7Hz), 6.6-6.8(2H), 4.64(s, 2H), 4.16(t, 2H, 7Hz), 2.8-3.5(m, 10H), 2.8(s, 3H), 1.9-2.2(m, 2H), 10.8(br, 1H) |
| 147 | (1182) | 83 | 247-249 | 7.4-7.8(m, 6H), 6.7-6.9(2H), 4.70(s, 2H), 4.25(t, 2H, 7Hz), 3.0-3.7(m, 12H), 2.2-2.4(m, 2H), 10.3(br, 1H) |
| 148 | (1194) | 89 | 115-123 | 0.8-3.8(20H), 4.18(2H, t, J=7Hz),4.63(2H, s), 6.55(1H, s), 6.62(1H, dd, J=2 and 8Hz), 7.57(1H, d, J=8Hz) |
| 149 | (1106) | 80 | 172-177 | 7.56(d, 1H, 7Hz), 6.5-6.8(m, 2H),4.61(s, 2H), 4.20(t, 2H, 7Hz), 3.8-4.0(m, 2H), 3.2-3.6(m, 4H), 2.0-2.8(m, 5H), 1.20(t, 3H), 11.3(br, 1H) |
| 149-1 | (1274) | 93 | 169-175 | δ7.56(d, 1H, 9Hz), δ6.6-6.8(m, 2H), δ4.65(s, 2H), δ4.20(t, 2H, 7Hz), δ3.5-3.8(m, 2H), δ3.1-3.4(m, 2H), δ1.8-3.0(m, 11H), δ0.94(t, 3H, J=6Hz), δ11.6(br, 1H) |
| 149-2 | (1278) | 91 | 157-163 | δ7.58(d, 1H, 9Hz), δ6.6-6.8(m, 2H), δ4.64(s, 2H), δ4.20(t, 2H, J=7Hz), δ3.6-3.8(m, 2H), δ3.1-3.5(m, 2H), δ1.1-3.0(m, 10H), δ0.96(d, 6H, J=7Hz), δ11.5(br, 1H) |
| 149-3 | (1282) | 89 | 188-192 | δ7.58(d, 1H, J=9Hz), δ6.6-6.8(m, 2H), δ4.80(s, 2H), δ4.16(t, 2H, J=7Hz, δ4.18(q, 2H, J=7Hz),δ3.5-3.8(m, 2H), 2.6-3.2(m, 4H), δ1.8-2.5(m, 7H), δ1.26(t, 3H, J=7Hz), δ11.6(br, 1H) |
| 149-4 | (1286) | 86 | 229-231 | δ7.60(d, 1H, J=9Hz), δ6.7-6.9(m, 2H), δ4.77(s, 2H), δ4.18(t, 2H, J=7Hz), δ1.8-3.9(m, 13H), δ3.08(s, 3H) |
| 149-5 | (1290) | 93 | 197-200 | δ7.66(d, 1H, J=9Hz), δ6.6-6.8(m, 2H), δ4.70(s, 2H), δ4.14(t, 2H, J=7Hz), δ3.4-3.8(m, 2H), δ2.8-3.2(m, 2H), δ2.4-2.8(m, 2H), δ1.0-2.2(m, 10H) |
| 149-6 | (1302) | 86 | 186-189 | δ7.58(d, 1H, J=9Hz), δ6.5-6.8(m, 2H), δ4.64(s, 2H), δ4.19(t, 2H, J=7Hz), δ3.80(t, 2H, J=7Hz), δ2.8-3.4(m, 3H), δ2.2-2.7(m, 6H), δ2.13(dt, 2H, J=7, 7Hz), δ2.10(s, 3H), δ11.3(br, 1H), δ5.2(br, 1H) |
| 149-7 | (1310) | 95 | 237-239 | δ7.56(d, 1H, J=9Hz), δ6.84(d, 1H, J=2Hz), δ6.80(dd, 1H, J=2, 9Hz), δ4.72(s, 2H), δ4.64(t, 2H, J=5Hz), δ3.4-4.0(m, 6H), δ1.8-3.0(m, 5H), δ11.2(br, 1H), δ7.2-7.4(m, 5H) |
| 149-8 | (1322) | 95 | 124-132 | 1.6-4.4(15H, m), 4.60(2H, s), 4.74(1H, m), 6.62(2H, m), 7.25(5H, m), 7.52(1H, d, J=8Hz) |
| 149-9 | (1326) | 83 | 98-105 | 2.7-4.2(12H, m), 4.32(1H, s), 4.58(3H, m), 6.50(1H, s), 6.55(1H, dd, J=2 and 8Hz), 7.24(9H, m), 7.50(1H, d, J=8Hz) |
| 149-10 | (1330) | 93 | 178-182 | δ7.0-7.6(m, 11H), δ6.7-6.9(m, 2H), δ6.23(s, 1H), δ4.16(t, 2H, J=7Hz), δ3.5-3.8(m, 2H), δ3.0-3.4(m, 2H), δ2.3-2.9(m, 4H), δ2.64(d, 2H, J=7Hz), δ1.6-2.3(m, 5H), δ12.5(br, 1H) |
| 149-11 | (1334) | 94 | 162-167 | δ7.0-7.6(m, 8H), δ4.34(t, 2H, J=7Hz), δ3.3-3.8(m, 2H), δ1.4-3.3(m, 13H), δ11.0(br, 1H) |
| 149-12 | (1338) | 95 | 206-208 | δ7.74(d, 1H, J=7Hz), δ7.0-7.4(m, 7H), δ4.24(t, 2H, J=7Hz), δ3.4-3.8(m, 2H), δ2.8-3.4(m, 4H), δ1.7-2.8(m, 9H), δ3.09(s, 3H) |
| 149-13 | (1342) | 90 | Oil | δ7.76(d, 1H, J=7Hz), δ7.1-7.4(m, 5H), δ6.4-6.6(m, 2H), δ4.16(t, 2H, J=7Hz), δ3.92(s, 3H), δ3.2-3.8(m, 4H), δ2.56(s, 3H), δ1.8-3.2(m, 11H), δ10.7(br, 1H) |

EXAMPLE 150

Production of compound No. 1140:

Example 130 was repeated except that phosphoric acid was used instead of concentrated hydrochloric acid. The desired compound was obtained in a yield of 80%.

Melting point: 146°-155° C.

$^1$H-NMR spectrum (CDCl$_3$ solution, δppm): Same as compound No. 1139.

EXAMPLE 151

Production of compound No. 1142:

In the same way as in Example 130 except that sulfuric acid was used instead of concentrated hydrochloric acid, the desired compound was obtained in a yield of 92%.

Melting point: 107°-110° C.

$^1$H-NMR spectrum (CDCl$_3$ solution, δppm): Same as in compound No. 1139.

EXAMPLE 152

Production of compound No. 1171:

A mixture of 0.35 g (1.1 millimoles) of compound No. 1168, 2 ml (26.8 millimoles) of ethyl bromide and 12 ml of acetonitrile was refluxed for 10 hours. After cooling, the reaction mixture was concentrated and the residue was washed with ether to obtain the desired compound in a yield of 40%.

Melting point: 205°-209° C.

$^1$H-NMR spectrum (CDCl$_3$ solution,δppm): 1.23(6H, d, J=7 Hz), 1.32(3H, t, J=7 Hz), 2.28(2H, m), 2.94(2H, m), 3.54(6H, m), 4.16(4H, m), 4.58(2H, s), 6.55(1H, s), 6.60(1H, dd, J=2 and 8 Hz), 7.30(1H, d, J=8 Hz).

EXAMPLE 153

Production of compound No. 1166:

0.69 g (2.5 millimoles) of compound No. 1164 was dissolved in 5 ml of ethyl acetate. Separately, 0.49 g (2.5 millimoles) of p-toluenesulfonic acid monohydrate was heated under reflux with 10 ml of toluene to remove water. The solvent was evaporated under reduced pressure, and the residue was dissolved by adding 5 ml of ethyl acetate. The resulting solution was gradually added to the previously prepared ethyl acetate solution at room temperature. The mixed solution was filtered and then dried to give the desired compound in a yield of Melting point: 162°–164° C.

$^1$H-NMR spectrum (CDCl$_3$, δppm): 2.36(3H, s), 2.4–3.4(6H, m), 3.60(2H, m), 4.03(6H, m), 4.62(2H, s), 6.47(1H, d, J=2 Hz), 6.54(1H, dd, J=2 and 9 Hz), 7.16(2H, d, J=9 Hz), 7.53(1H, d, J=9 Hz), 7.76(2H, d, J=9 Hz), 11.2(1H, brs).

EXAMPLES 154 TO 191

In the same way as in Example 153, the compounds indicated in Table 11 were produced from the corresponding starting materials.

TABLE 11

| Example No. | Compound No. | Yield (%) | Melting point (°C.) | $^1$H-NMR spectrum (CDCl$_3$ solution, δ ppm) |
|---|---|---|---|---|
| 154 | (1190) | 90 | 100–102 | 1.6–2.7(10H, m), 2.2–2.8(6H, m), 2.42(3H, s), 4.28(2H, t, J=7Hz), 4.78(s, 2H), 7.30(2H, d, J=7Hz), 7.60(1H, d, J=8Hz), 7.80(2H, d, J=7Hz) |
| 155 | (1139) | 68 | 184–189 | 1.8–2.2(7H, m), 2.35(s, 3H), 4.23(2H, t, J=7Hz), 2.6–3.9(6H, m), 4.75(s, 2H), 6.7–7.4(11H, m), 7.65(1H, d, J=8Hz), 9.4(1H, br) |
| 156 | (1102) | 60 | 106–108 | 2.0–3.1(11H), 3.32(2H, m), 3.84(2H, m), 4.08(2H, t, J=7Hz), 4.61(2H, s), 6.48(1H, s), 6.56(1H, dd, J=2 and 8Hz), 7.15(2H, d, J=7Hz), 7.52(1H, d, J=8Hz), 7.74(2H, d, J=7Hz) |
| 157 | (1170) | 80 | 163–167 | 1.24(6H, d, J=7Hz, 2.35(3H, s), 2.42(4H, m), 3.40(4H, m), 4.09(2H, t, J=7Hz), 4.12(2H, m), 4.62(2H, s), 6.48(1H, s), 6.55(1H, dd, J=2 and 8Hz), 7.16(2H, d, J=7Hz), 7.55(1H, d, J=8Hz), 7.76(2H, d, J=7Hz) |
| 158 | (1174) | 72 | 188–195 | 2.2–4.1(15H), 4.16(2H, t, J=7Hz), 4.67(2H, s), 6.59(1H, s), 6.64(1H, dd, J=2 and 8Hz), 7.23(2H, d, J=7Hz), 7.59(1H, d, J=8Hz), 7.76(2H, d, J=7Hz) |
| 159 | (1200) | 84 | — | 7.53(d, 1H, 7Hz), 6.6–6.8(2H, m), 4.62(s, 2H), 4.14(t, 2H, 7Hz), 2.5–3.4(m, 6H), 1.0–2.4(m, 7H), 0.90(s, 9H) |
| 160 | (1204) | 65 | 170–173 | 7.56(d, 1H, 7Hz), 6.5–6.7(m, 2H), 4.66(s, 2H), 4.08(t, 2H, 7Hz), 2.8–3.1(m, 2H), 2.4–2.6(m, 2H), 0.8–2.2(m, 20H) |
| 161 | (1208) | 66 | — | 7.55(d, 1H, 7Hz), 6.5–6.7(m, 2H), 4.60(s, 2H), 4.10(t, 2H, 7Hz), 2.6–2.9(m, 2H), 2.3–2.6(m, 2H), 0.8–2.2(m, 14H) |
| 162 | (1212) | 72 | — | 7.58(d, 1H, 7Hz, 6.5–6.7(m, 2H), 4.62(s, 2H), 4.09(t, 2H, 7Hz), 3.5–3.7(m, 2H), 1.1–3.0(m, 4H) |
| 163 | (1216) | 55 | 72–74 | 7.55(d,1H, 7Hz), 6.4–6.7(m, 2H), 4.62(s, 2H),4.18(t, 7Hz, 2H), 2.0–4.0(m, 13H), 11.1(br, 1H) |
| 164 | (1218) | 46 | — | 7.57(d, 1H, 7Hz), 6.5–6.7(m, 2H), 5.5(br, 2H), 4.61(s, 2H), 4.10(t, 2H, 7Hz, 2.8–3.2(m, 2H), 2.52(5, 7Hz, 2H), 1.6–2.4(m, 9H) |
| 165 | (1222) | 45 | — | 7.55(d, 1H, 7Hz), 6.5–6.7(m, 2H), 4.62(s, 2H), 4.10(t, 2H, 7Hz), 2.6–3.8(m, 6H), 1.9–2.5(m, 6H) |
| 166 | (1226) | 47 | — | 7.56(d, 1H, 7Hz), 6.5–6.7(m, 2H),4 .61(s, 2H), 4.08(t, 2H, 7Hz), 1.3–3.2(m, 23H) |
| 167 | (1230) | 52 | — | 8.03(d, 2H, 8Hz), 7.38(d, 2H, 8Hz), 7.56(d, 1H, 7Hz), 6.5–6.7(m, 2H), 4.60(s, 2H), 4.10(t, 2H, 7Hz), 1.7–3.7(m, 13H) |
| 168 | (1234) | 78 | — | 1.92(8H, m), 2.55(2H, t, J=7Hz), 3.07(3H, m), 4.12(2H, t, J=7Hz), 4.62(2H, s), 6.58(1H, s), 6.64(1H, dd, J=1 and 8Hz), 7.14(2H, m), 7.56(1H, d, J=8Hz), 7.96(2H, m) |
| 169 | (1238) | 69 | — | 7.56(d, 1H, 7Hz), 6.5–6.7(m, 2H), 4.62(s, 2H), 4.09(t, 2H, 7Hz), 1.3–3.1(m, 14H) |
| 170 | (1242) | 32 | 150–153 | 7.2–7.6(m, 5H), 6.6–6.8(m, 2H), 4.56(s, 2H), 4.16(t, 2H, 7Hz), 3.0–3.7(m, 7H), 1.7–2.6(m, 6H) |
| 171 | (1246) | 81 | — | 1.6–3.0(12H, m), 4.14(2H, t, J=7Hz), 4.64(2H, s), 4.75(2H, s), 6.60(1H, s), 6.65(1H, dd, J=2 and 9Hz), 6.7–7.4(5H, m), 7.57(1H,d, J=9Hz) |
| 172 | (1250) | 20 | — | 7.50(d, 1H, 7Hz), 7.0–7.5(m, 4H), 6.6–6.8(m, 2H), 4.58(s, 2H), 4.19(t, 2H, 7Hz), 2.7–3.3(m, 6H), 1.9–2.4(m, 4H) |
| 173 | (1254) | 69 | — | 6.5–7.7(m, 8H), 4.60(s, 2H), 4.18(t, 2H, 7Hz), 3.0–3.8(10H, m), 2.2–2.6(m, 2H) |
| 174 | (1258) | 69 | — | 7.55(d, 1H, 7Hz), 7.3–7.5(m, 5H), 6.6–6.8(m, 2H), 4.43(s, 2H), 4.08(t, 2H, 7Hz,2.8–3.5(m, 12H), 2.2–2.4(m, 2H) |
| 175 | (1262) | 55 | — | 2.24(2H, m), 2.58(6H, m), 3.56(4H, m), 4.14(2H, t, J=7Hz), 4.62(2H, s), 6.6–8.2(7H, m) |
| 176 | (1202) | 95 | 175–178 | 7.57(d, 1H, 7Hz), 6.53–6.75(m, 2H), 4.60(s, 2H), 4.16(t, 2H, 7Hz), 3.5–3.9(m, 2H), 3.0–3.5(m, 2H), 2.5–3.0(m, 2H), 1.6–2.3(m, 6H), 1.30(m, 1H), 0.93(s, 9H) |
| 177 | (1206) | 90 | 203–207 | 7.60(d, 1H, 7Hz), 6.5–6.7(m, 2H), 4.62(s, 2H), 4.18(t, 2H, 7Hz), 3.6–3.9(m, 2H), 3.0–3.4(m, 2H), 2.2–3.0(m, 4H), 0.8–2.2(m, 16H), 12.2(br, 1H) |
| 178 | (1210) | 85 | 204–207 | 7.59(d, 1H, 7Hz), 6.6–6.8(m, 2H), 4.69(s, 2H), 4.15(t, 2H, 7Hz), 3.3–3.7(m, 4H), 3.0–3.2(m, 2H), 2.7–3.0(m, 2H), 0.9–2.3(m, 10H), 11.8(br, 1H) |
| 179 | (1214) | 94 | 177–182 | 7.65(d, 1H, 7Hz), 6.6–6.8(m, 2H), 4.70(s, 2H), 4.17(t, 2H, 7Hz), 3.6–3.9(m, 2H), 3.3–3.6(m, 2H), 2.9–3.2(m, 2H), 1.2–2.8(m, 10H), 11.6(br, 1H) |
| 180 | (1220) | 85 | 201–203 | 7.60(d, 1H, 7Hz), 6.6–6.8(m, 2H), 4.70(s, 2H), 4.20(t, 2H, 7Hz), |

TABLE 11-continued

| Example No. | Compound No. | Yield (%) | Melting point (°C.) | $^1$H-NMR spectrum (CDCl$_3$ solution, δ ppm) |
|---|---|---|---|---|
| 181 | (1224) | 83 | 168–172 | 1.8–3.8(m, 15H), 10.3(br, 1H) 7.58(d, 1H, 7Hz), 6.6–6.8(m,2H), 4.72(s, 2H), 4.20(t, 2H, 7Hz), 2.8–4.0(m, 6H), 2.0–2.7(m, 6H), 12.2(br, 1H) |
| 182 | (1228) | 93 | 280–282 | 7.65(d, 1H, 7Hz), 6.6–6.8(m, 2H), 4.69(s, 2H), 4.18(t, 2H, 7Hz), 1.5–3.8(m, 23H), 11.9(br, 2H) |
| 183 | (1232) | 88 | 172–179 | 8.16(d, 2H, 8Hz), 7.50(d, 2H, 8Hz), 7.66(d, 1H, 7Hz), 6.6–6.8(m, 2H), 4.70(s, 2H), 4.24(t, 2H, 7Hz), 1.8–3.9(m, 13H), 12.2(br, 1H) |
| 184 | (1236) | 83 | 224–226 | 2.2–4.0(11H, m), 4.22(2H, t, J=7Hz), 4.42(2H, s), 4.66(2H, s), 6.64(1H, s), 6.69(1H, dd, J=2 and 9Hz), 7.20(2H, m), 7.57(1H, d, J=9Hz), 8.06(2H, m) |
| 185 | (1240) | 93 | 195–197 | 7.56(d, 1H, 7Hz), 6.6–6.8(m, 2H), 4.70(s, 2H), 4.20(t, 2H, 7Hz), 1.6–3.3(m, 14H), 11.8(br, 1H) |
| 186 | (1244) | 86 | 203–206 | 7.2–7.7(m, 5H), 6.6–6.8(m, 2H), 4.66(s, 2H), 4.24(t, 2H, 7Hz), 3.2–3.8(m, 7H), 1.8–2.8(m, 6H), 12.5(br, 1H) |
| 187 | (1248) | 86 | 243–246 | 1.8–2.5(4H, m), 3.1–3.9(10H, m), 4.20(2H, t, J=7Hz), 4.67(2H, s), 4.78(2H, s), 6.62(1H, s), 6.66(1H, dd, J=2 and 9Hz), 6.8–7.5(5H, m), 7.59(1H, d, J=9Hz) |
| 188 | (1252) | 80 | 209–213 | 7.55(d, 1H, 7Hz), 7.1–7.5(m, 4H), 6.6–6.8(m, 2H), 4.62(s, 2H), 4.23(t, 2H, 7Hz), 3.0–3.8(m, 6H), 2.3–2.8(m, 4H), 11.3(br, 1H) |
| 189 | (1256) | 83 | 209–212 | 7.57(d, 1H, 7Hz), 6.9–7.5(m, 5H), 6.6–6.8(m, 2H), 4.63(s, 2H), 4.13(t, 2H, 7Hz), 2.9–3.8(10H, m), 2.3–2.5(m, 2H), 11.8(br, 1H) |
| 190 | (1260) | 93 | 247–249 | 7.4–7.8(m, 6H), 6.7–6.9(2H, m), 4.70(s, 2H), 4.25(t, 2H, 7Hz), 3.0–3.7(m, 12H), 2.2–2.4(m, 2H), 10.3(br, 1H) |
| 191 | (1264) | 84 | 221–223 (decomp.) | 2.48(2H, m), 3.2–4.4(12H, m), 4.66(2H, s,) 6.6–8.3(7H, m) |
| 191-1 | (1294) | 90 | Oil | 1.10(3H, t, J=7Hz), 1.26(3H, t, J=7Hz), 1.5–3.8(19H, m), 4.09(2H, t, J=7Hz), 4.63(2H, s), 6.55(2H, m), 7.16(2H, d, J=7Hz), 7.54(1H, d, J=8Hz), 7.77(2H, d, J=7Hz) |
| 191-2 | (1298) | 97 | 111–114 | 1.90–3.76(15H, m), 3.98(4H, s), 4.10(2H, t, J=7Hz), 4.62(2H, s), 6.58(2H, m), 7.16(2H, d, J=7Hz), 7.52(1H, d, J=8Hz), 7.70(2H, d, J=7Hz) |
| 191-3 | (1314) | 80 | 207–210 | 1.5–4.1(22H, m), 4.67(2H, s), 6.64(2H, m), 7.27(7H, m), 7.57(1H, d, J=8Hz), 7.80(2H, d, J=7Hz) |
| 191-4 | (1318) | 67 | 175–178 | 1.3–3.9(22H, m), 4.00(2H, t, J=7Hz), 4.63(2H, s), 6.53(1H, d, J=2Hz), 6.63(1H, dd J=2 and 8Hz), 7.25(7H, m), 7.57(1H, d, J=8Hz), 7.85(2H, d, J=7Hz) |

EXAMPLE 1B

Tablets containing 10 mg of an active ingredient are prepared by the following procedure.

|  | Per tablet |
|---|---|
| Active ingredient | 10 mg |
| Corn starch | 55 mg |
| Crystalline cellulose | 35 mg |
| Polyvinyl pyrrolidone (as 10% aqueous solution) | 5 mg |
| Carboxymethyl cellulose calcium | 10 mg |
| Magnesium stearate | 4 mg |
| Talc | 1 mg |
| Total | 120 mg |

The active ingredient, corn starch and crystalline cellulose are passed through an 80-mesh sieve, and thoroughly mixed. The resulting powder is mixed with the polyvinyl pyrrolidone solution, and the mixture is granulated and passed through an 18-mesh sieve. The resulting granules are dried at 50° to 60° C., and again passed through an 18-mesh sieve to adjust their size. The carboxymethyl cellulose calcium, magnesium stearate and talc, previously passed through an 80-mesh sieve, are added to the granules, and they are mixed. The mixture is tableted by a tableting machine to produce tablets each having a weight of 120 mg.

EXAMPLE 2B

Tablets containing 100 mg of an active ingredient are produced by the following procedure.

|  | Per tablet |
|---|---|
| Active ingredient | 100 mg |
| Corn starch | 50 mg |
| Crystalline cellulose | 42 mg |
| soft silicic anhydride | 7 mg |
| Magnesium stearate | 1 mg |
| Total | 200 mg |

The above ingredients are passed through an 80-mesh sieve and thoroughly mixed. The resulting powder is compression-molded to produce tablets each having a weight of 200 mg.

EXAMPLE 3B

Capsules containing 50 mg of an active ingredient are produced by the following procedure.

|  | Per capsule |
|---|---|
| Active ingredient | 50 mg |
| Corn starch | 40 mg |
| Lactose | 5 mg |
| Magnesium stearate | 5 mg |
| Total | 100 mg |

The above ingredients are mixed, passed through an 80-mesh sieve, and thoroughly mixed. The resulting powder is filled into capsules in an amount of 100 mg for each.

EXAMPLE 4B

Injectable preparations containing 5 mg of an active ingredient in a vial for dissolution before use are produced by the following procedure.

| | Per vial |
|---|---|
| Active ingredient | 5 mg |
| Mannitol | 50 mg |

Just before use, these ingredients are dissolved in 1 ml of injectable distilled water, and the resulting preparations are used.

EXAMPLE 5B

Injectable preparations containing 20 mg of an active ingredient in an ampoule are produced by the following procedure.

| | Per ampoule |
|---|---|
| Active ingredient | 20 mg |
| Sodium chloride | 18 mg |
| Injectable distilled water | proper amount |
| Total | 2 ml |

EXAMPLE 6B

An adhesive patch preparation containing 17.5 mg of an active ingredient is produced by the following procedure.

Ten parts of poly(ammonium acrylate) is dissolved in 60 parts of water. Separately, 2 parts of glycerin diglycidyl ether is dissolved in 10 parts of water while heating. Furthermore, 10 parts of polyethylene glycol (grade 400), 10 parts of water and 1 part of the active ingredient are dissolved with stirring. Then, while the aqueous solution of poly(ammonium acrylate) is stirred, the aqueous solution of glycerin diglycidyl ether and the aqueous solution containing polyethylene glycol and the active ingredient are mixed to form a hydrogel-like solution containing the drug. The solution is coated on a pliable plastic film so that the rate of the active ingredient is 0.5 mg per cm$^2$. The coated surface is covered with releasing paper and cut to a size of 35 cm$^2$ to form the adhesive patch preparation.

EXAMPLE 7B

An adhesive patch containing 10 mg of an active ingredient is produced by the following procedure.

An aqueous sol is prepared from 100 parts of poly(sodium acrylate), 100 parts of glycerol, 150 parts of water, 0.2 part of triepoxypropyl isocyanurate, 100 parts of ethanol, 25 parts of isopropyl myristate, 25 parts of propylene glycol and 15 parts of the active ingredient. The sol is then coated to a thickness of 100 micrometers on the non-woven fabric surface of a composite film composed of a rayon non-woven fabric and a polyethylene film to form an adhesive layer containing the drug. The amount of the release aids (isopropyl myristate and propylene glycol) contained in this layer is about 20% by weight. The adhesive layer is then crosslinked at 25° C. for 24 hours, and a releasing film is bonded to the adhesive layer surface. The entire film is then cut into pieces each having an area of 35 cm$^2$.

The pharmacological effects of the compounds of this invention represented by general formula (1) were studied. By using the heart of an adult mongrel dog, the activity of the compounds of general formula (1) were tested in vitro and in vivo. The heart of an anaethetized dog was extracted and suspended in a chamber at 37° C. in Tyrode's solution. The drug was added to Tyrode's solution being perfused through the heart specimen, and electrophysiological effects of the drug on cardiac action potential duration (APD) and maximum rate of depolarization were studied. An anaethetized dog was cut open at the chest. The sinus node was crushed to extinguish the pacemaker activity and under ventricular pacing via an electrode sutured on the right ventricle, the effective refractory period (ERP) of the right ventricle was measured before and after administration of the drug.

Furthermore, the anaethetized dog was cut open at the chest. Bipolar electrodes were sutured to the right atrial surface, and stimulation electrodes were attached to the vagus nerves at both sides of the cervical region. Atrial fibrillation was induced by the method of Goldberger et al. A. L. Goldberger et al.: International Journal of Cardiology, 13, 47 (1986), and the effect of the drug to cause disappearance of fibrillation was examined. Further, the anaethetized dog was cut open at the chest. Left anterior descending coronary artery was ligated, and ninety minutes later, reperfused to prepare a myocardial infarction which was liable to develop tachycardia. At that time, a bipolar plunge electrode was placed in the interventricular septum near the ligated site. Several days after the operation, programmed electrical stimulation was applied to induce tachycardia. The effect of the drug to cause disappear of tachycardia was examined.

These tests showed that the compounds of general formula (1) are valuable as class III-type antiarrhythmic agents having marked APD and ERP prolonging activity, and exhibit anti-arrhythmic activity in arrhythmic models. It was confirmed that some of the compounds of general formula (1) also have the activity of inhibiting the maximum rate of depolarization (Vmax) of the myocardial action potential which the class I-type antiarrhythmic agents have, but the others have the characteristics of pure class III anti-arrhythmic agents having no Vmax inhibiting activity. It was also found that the compounds of general formula (1) have equivalent or greater APD and ERP prolonging activity to or than clofilium and sotalol used as controls. Furthermore, the pharmacological effects of the compounds of this invention on the central nervous system were examined in vitro and in vivo.

Striatal membranes fractions were prepared from a rat brain, and the affinity of the compounds of this invention on dopamine 2 receptors was determined by using [$^3$H] spiperone assay from membranes fractions as an index. Moreover, frontal cortex membranes were prepared from a rat brain, and the affinity of the test drugs on serotonine 2 receptor was determined by using [$^3$H] ketenserin binding assay. It was shown that the compounds of general formula (1) of the invention have marked anti-dopamine activity and anti-serotonine activity.

The effects of the compounds of general formula (1) on the apomorphine-induced climbing behavior of mice (i.e. anti-dopamine activity) and the the effects of the test drugs of the invention on the quipazine-induced head twitching of mice (i.e. anti-serotonine activity) were also examined. It was made clear that the compounds of this invention represented by general formula (1) have marked anti-dopamine activity and anti-serotonine activity both in vivo and in vitro, and have potentiality as an anti-psychotic agent, an anti-depressant, an antianxiety agent, a sedative or as an anti-dementia agent. A toxicity test on the compounds of general formula (1) showed that these compounds have relatively weak toxicity and can be used as a medicine having a broad safety range.

TEST EXAMPLE 1D (EFFECT ON APD)

An adult mongrel dog was anaethetized with intravenous administration of pentobarbital, 30 mg/kg. The heart was quickly removed, and the right ventricular free wall was dissected in the Tyrode's solution. The right ventricular free wall was fixed within an incubator at 37° C., and field stimulation at 1 Hz was carried out. Intracellular potentials were measured by piercing glass microelectrodes (10–20 megaohms) into the Purkinje fiber and the wave form of cardiac action potential drawn on an oscilloBraun tube via an amplifier was analyzed by a computer. Value of APD was obtained at 75% of full repolarization ($APD_{75}$). The drug was added to Tyrode's solution (20 ml) perfused through the specimen. The effect of the drug was expressed by a percent change in $APD_{75}$ after incubation for 20 minutes with the control value of APD before application of the drug being taken as 100%. The results are shown in Tables 4D, 9D and 10D.

TABLE 9D

| Compound | $APD_{75}$ % Dose (μg/ml) | | |
|---|---|---|---|
| | 1 | 3 | 10 |
| 100 | 21 | 31 | — |
| 404 | — | 4 | — |
| 102 | 20 | 30 | — |
| 104 | 21 | 30 | — |
| 214 | 15 | 15 | — |
| 216 | 13 | 17 | — |
| 144 | 13 | 26 | 33 |
| 196 | 7 | 10 | 11 |
| 204 | 3 | 7 | 8 |
| 952 | 0 | 3 | 7 |
| 212 | 4 | 8 | — |
| 108 | 0 | 2 | — |
| 208 | 0 | 5 | 9 |
| 244 | 6 | 9 | 11 |
| 180 | 5 | 11 | 15 |
| 184 | — | 16 | 31 |
| 132 | 7 | 18 | 21 |
| 168 | 0 | 3 | — |
| 160 | 0 | 7 | 11 |
| 172 | 0 | 8 | — |
| 116 | 14 | 38 | 44 |
| 128 | 9 | 18 | — |
| 188 | 17 | 19 | 19 |
| 289 | 7 | 8 | — |
| Clofilium | — | — | 15 |

TABLE 10D

| Compound | $APD_{75}$ % Dose (μg/ml) | | |
|---|---|---|---|
| | 1 | 3 | 10 |
| 630 | — | 25 | 48 |
| 1020 | 10 | 14 | 19 |
| 1022 | 0 | 11 | 18 |
| 634 | 4 | 7 | 11 |
| 820 | 4 | 5 | — |
| 286 | 17 | 29 | — |
| 770 | 0 | 7 | — |
| 638 | 0 | 7 | — |
| 422 | 0 | 3 | — |
| 470 | 13 | 16 | 20 |
| 292 | 15 | 25 | 28 |

TABLE 10D-continued

| Compound | $APD_{75}$ % Dose (μg/ml) | | |
|---|---|---|---|
| | 1 | 3 | 10 |
| 293 | 0 | 4 | — |
| 294 | — | 11 | 35 |
| 290 | — | 11 | 35 |
| 632 | — | 44 | 18 |
| 276' | 5 | 12 | 23 |
| 272' | — | 8 | 10 |
| 268' | — | 7 | 15 |
| Clofilium | — | — | 15 |

TABLE 4D

| Compound | $ADP_{75}$ % Dose (μg/ml) | | |
|---|---|---|---|
| | 1 | 3 | 10 |
| 1198 | 4 | 6 | — |
| 1108 | 0 | 7 | 9 |
| 1110 | — | 10 | 20 |
| 1139 | 33 | 55 | 65 |
| 1126 | — | 19 | 27 |
| 1171 | 0 | 10 | — |
| 1266 | — | 5 | — |
| 1114 | 11 | 22 | 35 |
| 1118 | 10 | 13 | 24 |
| 1122 | 4 | 15 | 42 |
| 1146 | 18 | 25 | 34 |
| 1119 | — | 4 | — |
| 1171 | — | 10 | — |
| 1166 | 4 | 6 | — |
| 1102 | — | 6 | — |
| 1106 | — | 8 | 13 |
| 1158 | — | 10 | 13 |
| 1129 | — | 7 | — |
| 1131 | — | 7 | — |
| 1134 | 7 | 9 | — |
| 1194 | 16 | 19 | — |
| 1150 | 4 | 12 | 14 |
| 1214 | — | 4 | — |
| 1302 | — | 5 | 13 |
| 1274 | 6 | 19 | — |
| 1282 | — | 11 | 19 |
| 1278 | — | 9 | 24 |
| 1286 | — | 7 | — |
| 1290 | — | 11 | 28 |
| Clofilium | — | — | 15 |

TEST EXAMPLE 2D (ACTIVITY ON ERP)

In an anaethetized and open-chested adult mongrel dug, a silver-silver chloride electrode was sutured to the right ventricle, and ventricular pacing was performed at a stimulation interval of 400 msec for a duration time of 4 msec, twice diastolic threshold. Then, a small amount of alcohol was injected through the sinus artery to extinguish the pacemaker activity, and under ventricular pacing, ERP was measured. Ten stimulations were taken as one train, and the interval between trains when the response to the first stimulation disappeared was defined as ERP. Programmable cardiac stimulator (DHM-226-3 made by Daiya Medical Co., Ltd.) was used to determine ERP. ERP before drug administration (intravenously or intraduodenally) was taken as 100%, and ERP prolonging activity of the drugs was expressed by %. The results are shown in Tables 5D, 11D and 12D.

TABLE 5D

| Compound | ERP % Dose mg/kg i.v. | | | |
|---|---|---|---|---|
| | 0.1 | 0.3 | 1 | 3 |
| 1114 | — | — | 3 | 8 |

TABLE 5D-continued

| | ERP % Dose mg/kg i.v. | | | |
|---|---|---|---|---|
| Compound | 0.1 | 0.3 | 1 | 3 |
| 1118 | 5 | 9 | 22 | 26 |
| 1122 | — | — | 9 | 15 |
| 1126 | — | 8 | 12 | 15 |
| 1139 | — | 5 | 11 | — |
| 1146 | 4 | 16 | 20 | — |
| 1274 | 0 | 6.7 | 13.3 | 13.3 |
| 1282 | 0 | 0 | 6 | 6 |
| 1278 | 1.6 ± 1.6 | 4.8 ± 1.6 | 13.0 ± 2.4 | 19.8 ± 0.6 |
| 1286 | 8.3 | 8.3 | 16.6 | 16.6 |
| 1290 | 0 | 5.9 | 11.8 | 17.7 |
| Clofilium | 7.0 ± 1.3 | 15.2 ± 2.4 | 22.4 ± 1.6 | — |
| Sotalol | 1.7 ± 1.7 | 6.7 ± 0.9 | 8.7 ± 1.2 | 15.5 ± 0.5 |

TABLE 11D

| | ERP % Dose mg/kg i.v. (*mg/kg i.d.) | | | |
|---|---|---|---|---|
| Compound | 0.1 | 0.3 | 1 | 3 |
| 102 | 11.7 ± 3.2 | 21.3 ± 3.3 | 23.3 ± 2.9 | — |
| | *0 | *13 | *27 | — |
| 216 | 8 | 8 | 8 | 8 |
| 144 | 10.0 ± 1.7 | 15.5 ± 4.9 | 21.1 ± 6.2 | — |
| 196 | 5 | 5 | 18 | — |
| 212 | 7.1 ± 3.4 | 7.1 ± 3.4 | 13.8 ± 3.6 | 13.8 ± 3.6 |
| 244 | 0 | 9 | 9 | 17 |
| 184 | 4.3 ± 2.2 | 6.3 ± 3.4 | 6.3 ± 3.4 | — |
| 132 | 2.4 ± 2.4 | 2.4 ± 2.4 | 4.8 ± 4.8 | 4.8 ± 4.8 |
| 116 | 3 | 7 | 9 | 9 |
| Clofilium | 7.0 ± 1.3 | 15.2 ± 2.4 | 22.4 ± 1.6 | — |
| Sotalol | 1.7 ± 1.7 | 6.7 ± 0.9 | 8.7 ± 1.2 | 15.5 ± 0.5 |

Average value for three animals
— not performed

TABLE 12D

| | ERP % Dose mg/kg i.v. (*mg/kg i.d.) | | | |
|---|---|---|---|---|
| Compound | 0.1 | 0.3 | 1 | 3 |
| 286 | 5.7 ± 0.3 | 15.7 ± 5.5 | 15.7 ± 5.5 | 17.7 ± 7.3 |
| | *0 | *0 | *10 | *19 |
| 630 | 3 | 5 | 8 | — |
| 470 | 0 | 0 | 2 | 8 |
| 292 | 8 | 8 | 8 | — |
| 276' | 0 | 0 | 7 | 7 |
| 268' | 0 | 0 | 0 | 6.3 |
| Clofilium | 7.0 ± 1.3 | 15.2 ± 2.4 | 22.4 ± 1.6 | — |
| Sotalol | 1.7 ± 1.7 | 6.7 ± 0.9 | 8.7 ± 1.2 | 15.5 ± 0.5 |

TEST EXAMPLE 3D (ATRIAL FIBRILLATION MODEL)

In an anaethetized and open-chested mongrel dog, bipolar electrodes (silver and silver-silver chloride electrodes) were sutured respectively to the right atrium for stimulation and recording. The vagus nerves on both sides of the cervical region were isolated and cut, and stimulation electrodes were attached to the peripheral end. The atrial fibrillation was induced in accordance with the method of Goldberger et al. After cardiac arrest induced by stimulating the vagus nerves, electrical stimulation was applied to the right atria at a high frequency. Compounds Nos. 102, 144, 1126, 1118, 1139 and 1146 could cause disappearance fibrillation occurring continuously when they are administered in a dose of 0.3 to 3 mg/kg or 1 to 10 mg/kg.

TEST EXAMPLE 4D (ACUTE TOXICITY)

By using male ddY-strain 5-week old mice (3 to 4 per group), the compounds of general formula (1) were each administered orally or intraperitoneally as a solution in saline or as a suspension in methyl cellulose, and 24 hours after the administration, the toxicity of the compounds was evaluated. The results are shown in Tables 6D and 13D.

TABLE 6D

| Compound | LD$_{50}$ mg/kg p.o. (*mg/kg i.p.) |
|---|---|
| 1110 | >300 |
| 1139 | >1,000 |
| 1114 | >300 |
| 1126 | >300 |
| 1118 | >300 |
| 1171 | >300 |
| 1122 | >300 |
| 1146 | >300 |
| 1158 | >300 |
| 1194 | >300 |
| 1150 | >300 |
| 1171 | >300 |
| 1175 | >300 |
| 1282 | >300 |
| 941 | >300 |
| 268.1 | >300 |
| 1298 | >300 |
| 1290 | <300 |
| 1278 | >300 |
| 1282 | >300 |
| 1274 | <300 |
| 1140 | >300 |
| 1236 | <300 |
| 1286 | >300 |
| 1304 | >300 |
| 1302 | >300 |
| 281.1 | >300 |
| 1400 | >300 |
| 271.1 | >300 |
| 1404 | >300 |
| Clofilium | >1,000 |
| | *≈30 |

TABLE 13D

| Compound | LD$_{50}$ mg/kg p.o. (*mg/kg i.p.) |
|---|---|
| 102 | ≈300 |
| | *≈100 |
| 216 | 300–600 |
| 144 | >300 |
| | ≈100 |
| 196 | ≈300 |
| 212 | 300–600 |
| 208 | ≈300 |
| 244 | ≈300 |
| 184 | ≈300 |
| 132 | >300 |
| 160 | >300 |
| 286 | 300–1000 |
| | *100–500 |
| 188 | >300 |
| 470 | >300 |
| 295 | >300 |
| 630 | >300 |
| 632 | >300 |
| 116 | >300 |
| 128 | >300 |
| 268' | >300 |
| Clofilium | >1,000 |
| | *≈30 |

TEST EXAMPLE 5 (AFFINITY FOR DOPAMINE 2 RECEPTOR)

[$^3$H]spiperone binding assay

The affinity of the compounds of this invention to the dopamine 2 receptor was determined on the basis of the ability to substitute [$^3$H] spiperone from stratal membrane fractions prepared from the brain a Wistarstrain male rat.

The rat was decapitated, and the brain was obtained. The striatum was homogenized in 40 volumes of 50 mM Tris-HCl buffer (pH 7.6), and then centrifuged. The pellets were again homogenized in 50 volumes of the same buffer, and used in a binding test. The binding test was conducted by the following procedure.

The stria (original tissue weight 20 mg/ml), 100 microliters of a test drug and 0.5 nM of [$^3$H] spiperone were incubated at 37° C. for 10 minutes in 50 mM Tris-HCl buffer (pH 7.6). Then, the reaction mixture was suction-filtered through a glass fiber filter (Watmann GF/B) and washed with a buffer three times.

The filter was put in a scintillation cocktail (ACSII, Amersham Co.), and after mixing, left to stand overnight. The radioactivity held on the filter was measured by a liquid scintillation counter. The nonspecific binding was measured in the presence of 1 μM of (+) butaclamol. The concentration of the test drug which inhibited 50% of a specific binding was determined from the graph and defined as IC$_{50}$. Ki was calculated from the following equation.

$$Ki = \frac{IC_{50}}{1 + \frac{[^3H] \text{ spiperone concentration (nM)}}{0.28}}$$

The Ki values of the test drugs are shown in Table 14.

TEST EXAMPLE 6 (AFFINITY FOR A SEROTONINE 2 RECEPTOR)

[$^3$H] ketanserin binding assay

The affinity of the compound of the invention was determined on the basis of the ability to substitute [$^3$H] ketanserin from a frontal cortex fraction prepared from the brain of a Wistar male rat.

The rat was decapitated, and the brain was obtained. The frontal cortex was homogenized in 40 volumes of 50 mM Tris-HCl buffer (pH 7.6), and then centrifuged. The pellets were again homogenized in 100 volumes of the same buffer, and used in a binding test. The binding test was conducted by the following procedure.

The frontal cortex (original tissue weight 1 mg/ml), 100 microliters of a test drug and 1 nM of [$^3$H] ketanserin were incubated at 37° C. for 10 minutes in 50 mM Tris-HCl buffer (pH 7.6). Then, the reaction mixture was suction-filtered through a glass fiber filter (Watmann GF/B) and washed with a buffer three times.

The filter was put in a scintillation cocktail (ACSII, Amersham Co.), and after mixing, left to stand overnight. The radioactivity held on the filter was measured by a liquid scintillation counter. The nonspecific binding was measured in the presence of 1 μM of methysergide. The concentration of the test drug which inhibited 50% of a specific binding was determined from the graph and defined as IC$_5$. Ki was calculated from the following equation.

$$Ki = \frac{IC_{50}}{1 + \frac{[^3H] \text{ ketanserin concentration (nM)}}{1.75}}$$

The Ki values of the test drugs are shown in Table 14.

TABLE 14

| Test compound | [3H] spiperone Ki (nM) | [$^3$H] ketanserin Ki (nM) |
|---|---|---|
| 1256 | 286 | 175 |
| 1178 | >400 | >600 |
| 1182 | >400 | >600 |
| 1264 | >400 | >600 |
| 1186 | >400 | 315 |
| 176 | >400 | >600 |
| 1150 | >400 | 306 |
| 1138 | 329 | 173 |
| 1236 | 122 | 9.1 |
| 1146 | >400 | 441 |
| 1228 | >400 | >600 |
| 1162 | >400 | >600 |
| 1246 | >400 | >600 |
| 1154 | >400 | >298 |
| 1344 | >400 | >600 |
| 1334 | >400 | 227 |
| 1330 | >400 | >600 |
| 1298 | >400 | 382 |
| 1286 | >400 | 475 |

TEST EXAMPLE 7 (ANTI-PSYCHOTIC ACTIVITY)

By using 5 week old ddY-strain male mice (10 per group), the anti-dopamine (anti-DA hereinafter) and anti-serotonine (anti-5-HT hereinafter) activities were examined by the following procedures. All does of test drugs were adjusted to 1 mg/ml. They were each suspended in 0.5% carboxymethyl cellulose (CMC)/saline so that their volume administered was 0.1 ml/10 g. The suspension was administered intraperitoneally.

1. Effect of apomorphine on the climbing behavior (anti-DA activity):

Apomorphine (3 mg/kg) was subcutaneously administered 30 minutes after the intraperitoneal administration of each test drug, and 20 minutes later, the climbing time of each mouse was measured.

2. Effect of quipazine on the head twitch (anti-5-HT activity):

Quipazine (3 mg/kg) was administered intraperitoneally 30 minutes after the intraperitoneal administration of each test drug. After the lapse of 10 minutes, 20 minutes and 30 minutes from then, the number of head twitchings of each mouse which occurred for 2 minutes was counted.

The results are shown in Tables 15 and 16. Compound No. 1236 significantly inhibited the apomorphine-induced climbing behavior and quipazine-induced head twitching of the mice, and was found to have strong anti-DA activity and anti-5-HT activity.

These results correspond to the results obtained in vitro in Test Examples 5 and 6 and shown in Table 14.

TABLE 15

| Apomorphine-induced climbing of mice | | | | |
|---|---|---|---|---|
| Drug | Dose (mg/kg i.p.) | Number mice | Apomorphine-induced climbing (mean ± S.E.) (sec/2 min.) | Percent inhibition (%) |
| Control | 0 | 20 | 72.9 ± 8.5 | — |
| 1236 | 1 | 20 | 32.0 ± 8.6** | 56 |

Control: 0.5% CMC/saline
**p < 0.01

TABLE 16

| | Quipazine-induced head twitching of mice | | | |
|---|---|---|---|---|
| Drug | Dose (mg/kg i.p.) | Number mice | Quipazine-induced head twitching (number/2 min.) | Percent inhibition (%) |
| Control | 0 | 10 | 6.7 ± 0.8 | — |
| 1256 | 1 | 10 | 3.8 ± 0.9** | 43 |
| 1236 | 1 | 10 | 0.1 ± 0.1*** | 99 |

Control: 0.5% CMC/saline
**p < 0.05
***p < 0.001

Examples 1D and 2D and Tables 4D, 5D and 9D-12D show that the compounds of general formula (1) of this invention have equivalent or greater electrophysiological activities and anti-arrhythmic activity to or than clofilium, etc. used as a control. Furthermore, Test Examples 5 to 7 and Tables 14 to 16 clearly show that the compounds of general formula (1) provided by this invention have anti-dopamine and anti-serotonine activities. The toxicitiy of the compounds of general formula (1) in accordance with this invention is generally weak, as shown in Test Example 3 and Table 13. The compounds of general formula (1) are thus considered to be drugs which generally have high activity, weak toxicity and high safety.

Accordingly, the compounds of general formula (1) in accordance with this invention are useful as therapeutic and prophylactic agents for arrhythmia, ischemic heart diseases, myocardial infarction, angina pectoris and heart failure. The compounds of this invention represented by general formula (1) can be used especially favorably for that type of arrhythmia which is difficult to cure with conventional anti-arrhythmic agents belonging to classes I to IV. They are applicable to, and expected to be effective for, patients who are suffering, or likely to suffer, from ventricular tachycardia entailing sudden death or ventricular arrhythmia involving ventricular fibrillation.

Furthermore, the compounds of general formula (1) in accordance with this invention are expected to be effective as therapeutic and prophylactic agents for mania, melanchoria, schizophrenia, delirium, dementia and anxiety.

We claim:

1. An amine represented by the following formula (1), or its acid addition salt or its quaternary ammonium salt

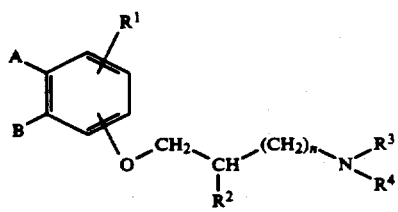

(1)

wherein
A and B together form a group selected from the group of the following formulae:
—CO—CR$^5$R$^6$—O—,
—CR$^{13}$R$^{14}$—CR$^{15}$R$^{16}$—O— and
—CH(OH)—CR$^{17}$R$^{18}$—O—;
R$^1$ is hydrogen, lower alkyl, lower alkoxy, halogen, amino, nitro or lower alkylsulfamoyl;
R$^2$ is hydrogen, hydroxyl or lower alkyl;

R$^3$ is hydrogen, alkyl, lower alkoxy-lower alkyl, lower alkoxy-lower alkoxy-lower alkyl, lower alkoxycarbonyl-lower alkyl, lower acyl-lower alkyl, ethylenedioxy lower alkyl, lower alkenyl, lower alkynyl, cycloalkyl, phenyl, benzyl,

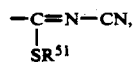

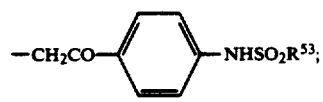

R$^4$ is alkyl, lower alkenyl, lower alkynyl, lower alkoxy-lower alkyl, hydroxyalkyl, cycloalkyl, benzyl or adamantyl;
R$^5$, R$^6$, R$^{13}$, R$^{14}$, R$^{15}$, R$^{16}$, R$^{17}$ and R$^{18}$ are identical or different, and each represents hydrogen or lower alkyl;
R$^{51}$, R$^{52}$ and R$^{53}$ are identical or different, and each represents lower alkyl;
n is a number of 0, 1, 2, 3 or 4; and
with the proviso that when A and B, taken together, represent —CR$^{13}$R$^{14}$—CR$^{15}$R$^{16}$—O—, R$^2$ is hydrogen or lower alkyl.

2. An amine represented by the following formula (1), or its acid addition salt or its quaternary ammonium salt

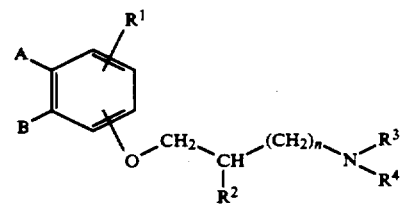

wherein A and B together form the group —CO—CR$^5$R$^6$—O—, wherein
R$^1$ is hydrogen, lower alkyl, lower alkoxy, halogen, amino, nitro or lower alkylsulfamoyl;
R$^2$ is hydrogen, alkyl, lower alkoxy-lower alkyl, lower alkoxy-lower alkoxy-lower alkyl, lower alkoxycarbonyl-lower alkyl, lower acyl-lower alkyl, ethylenedioxy lower alkyl, lower alkenyl, lower alkynyl, cycloalkyl, phenyl, benzyl

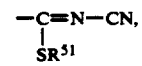

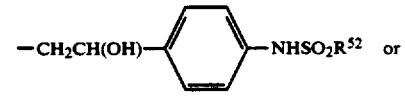

-continued

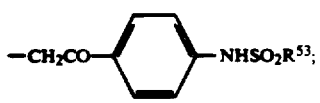

R$^4$ is alkyl, lower alkenyl, lower alkynyl, lower alkoxy-lower alkyl, hydroxyalkyl, cycloalkyl, benzyl, phenethyl, cyclohexyloxy, 2-bicyclo[2.2.1]-heptanyl or adamantyl;

R$^5$ and R$^6$ are identical or different, and each represents hydrogen or lower alkyl;

R$^{51}$, R$^{52}$ and R$^{53}$ are identical or different, and each represents lower alkyl; and n is a number of 0, 1, 2, 3 or 4.

3. An amine according to claim 1 represented by the following formula (1)-1, or its acid addition salt or its quaternary ammonium salt,

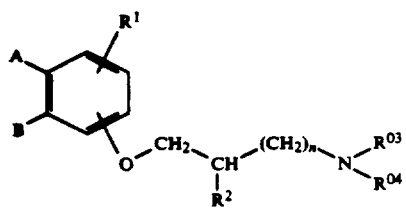 (1)-1 wherein
A, B, R$^1$, R$^2$ and n are the same as defined in formula (1);

R$^{03}$ is hydrogen, alkyl, lower alkoxy-lower alkyl, lower alkoxy-lower alkoxy-lower alkyl, lower alkoxycarbonyl-lower alkyl, lower acyl-lower alkyl, ethylenedioxy-lower alkyl, lower alkenyl, lower alkynyl, cycloalkyl, phenyl, benzyl,

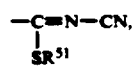

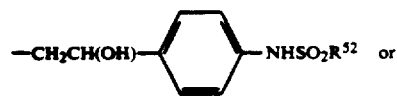 or

R$^{04}$ is alkyl, lower alkenyl, lower alkynyl, lower alkoxy-lower alkyl, hydroxyalkyl, cycloalkyl, benzyl, phenethyl, cyclohexyloxy, 2-bicyclo[2.2.1-]heptanyl or adamantyl; and, R$^{51}$, R$^{52}$ and R$^{53}$ are as defined as in formula (1).

4. A pharmaceutical composition comprising an effective amount of the compound of claim 1 as an active ingredient and a pharmaceutically acceptable carrier.

5. A pharmaceutical composition having antiarrhythimic activity containing an effective amount of the compound of claim 3 as an active ingredient and a pharmaceutically acceptable carrier.

6. A method for treatment of arrythmia in a patient in need thereof, comprising administering to said patient a pharmacologically effective amount of the compound of claim 1 as an active ingredient.

7. A method for treatment of arrythmia in a patient in need thereof, comprising administering to said patient a pharmacologically effective amount of the compound of claim 3 as an active ingredient.

8. A method for treating psychoneurological diseases treatable with dopamine or serotonin antagonists in a patient in need thereof, comprising administering to said patient a psychoneurologically effective amount of the compound of claim 1 as an active ingredient.

9. An amine according to claim 1 wherein A and B, taken together, represent the group—CH(OH)—CR$^{17}$R$^{18}$—O—.

10. An amine compound according to claim 3 wherein A and B, taken together, represent the group—CH(OH)—CR$^{17}$R$^{18}$—O—.

11. An amine compound according to claim 2 wherein said compound is selected from the group consisting of

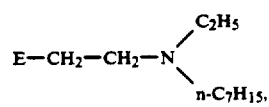 (100)

| | |
|---|---|
| Hydrochloride of (100), | (102) |
| p-Toluenesulfonate of (100), | (104) |

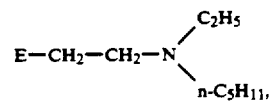 (106)

| | |
|---|---|
| p-Toluenesulfonate of (106), | (108) |

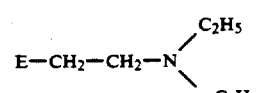 (110)

| | |
|---|---|
| p-Toluenesulfonate of (110), | (112) |

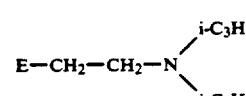 (114)

| | |
|---|---|
| Hydrochloride of (114), | (116) |
| E—CH$_2$—CH$_2$—NH-i-C$_4$H$_9$, | (118) |
| Hydrochloride of (118), | (120) |

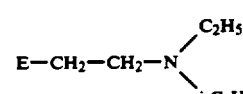 (122)

| | |
|---|---|
| Hydrochloride of (122), | (124) |

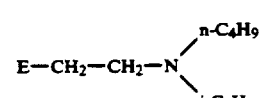 (126)

| | |
|---|---|
| Hydrochloride of (126), | (128) |
| E—CH$_2$—CH$_2$—N(i-C$_4$H$_9$)$_2$, | (130) |
| Hydrochloride of (130), | (132) |

-continued $E-CH_2-CH_2-N\begin{smallmatrix}i\text{-}C_4H_9\\t\text{-}C_4H_9,\end{smallmatrix}$ (134)

Hydrochloride of (134), (136)

$E-CH_2-CH_2-N\begin{smallmatrix}i\text{-}C_4H_9\\n\text{-}C_7H_{15},\end{smallmatrix}$ (138)

Hydrochloride of (138), (140)

$E-CH_2-CH_2-N(n\text{-}C_4H_9)_2,$ (142)

p-Toluenesulfonate of (142), (144)

$E-CH_2-CH_2-N(CH_2-C\equiv CH)_2,$ (150)

Hydrochloride of (150), (152)

$E-CH_2-CH_2-N(CH_2-C=CH_2)_2,$ (154)

Hydrochloride of (154), (156)

$E-CH_2-CH_2-N\begin{smallmatrix}CH_2-CH=CH_2,\\C_6H_{11}\end{smallmatrix}$ (158)

Hydrochloride of (158), (160)

$E-CH_2-CH_2-N-(C_6H_{11})_2,$ (162)

Hydrochloride of (162), (164)

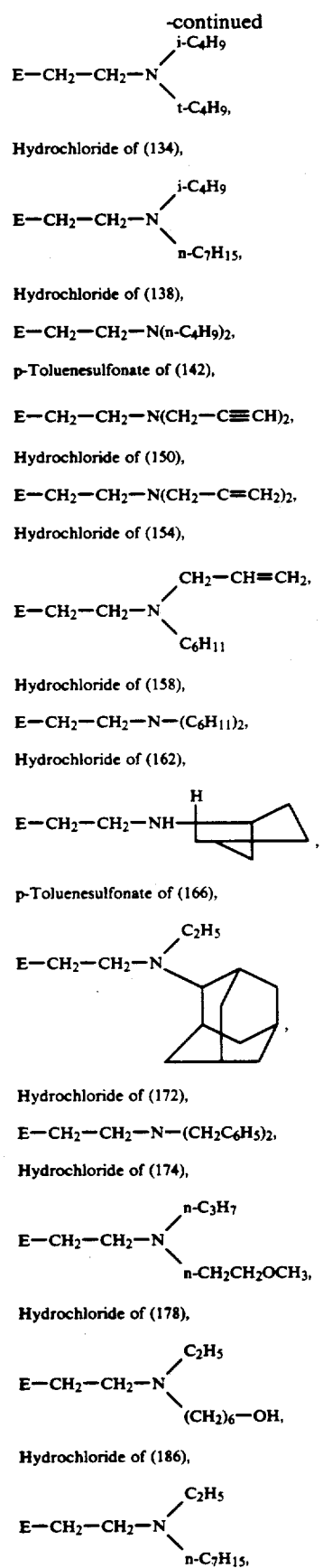

(166)

p-Toluenesulfonate of (166), (168)

(170)

Hydrochloride of (172), (172)

$E-CH_2-CH_2-N-(CH_2C_6H_5)_2,$ (174)

Hydrochloride of (174), (176)

$E-CH_2-CH_2-N\begin{smallmatrix}n\text{-}C_3H_7\\n\text{-}CH_2CH_2OCH_3,\end{smallmatrix}$ (178)

Hydrochloride of (178), (180)

$E-CH_2-CH_2-N\begin{smallmatrix}C_2H_5\\(CH_2)_6-OH,\end{smallmatrix}$ (186)

Hydrochloride of (186), (188)

$E-CH_2-CH_2-N\begin{smallmatrix}C_2H_5\\n\text{-}C_7H_{15},\end{smallmatrix}$ (194)

-continued p-Toluenesulfonate of (194), (196)

$E-CH_2-CH_2-N\begin{smallmatrix}C_2H_5\\n\text{-}C_9H_{19},\end{smallmatrix}$ (198)

p-Toluenesulfonate of (198), (200)

$E-CH_2-N+n\text{-}C_4H_9)_2,$ (202)

p-Toluenesulfonate of (202), (204)

$E-CH_2-CH_2-N\begin{smallmatrix}C_2H_5\\n\text{-}C_5H_{11},\end{smallmatrix}$ (206)

p-Toluenesulfonate of (206), (208)

$E-CH_2-CH_2-N\begin{smallmatrix}C_2H_5\\n\text{-}C_7H_{15},\end{smallmatrix}$ (210)

p-Toluenesulfonate of (210), (212)

$E-CH-CH_2-N\begin{smallmatrix}OH\phantom{xx}C_2H_5\\\phantom{xxxxxx}n\text{-}C_7H_{15},\end{smallmatrix}$ (214)

p-Toluenesulfonate of (214), (216)

$E-CH-CH_2-N\begin{smallmatrix}CH_3\phantom{xx}C_2H_5\\\phantom{xxxxxx}n\text{-}C_7H_{15},\end{smallmatrix}$ (218)

p-Toluenesulfonate of (218), (220)

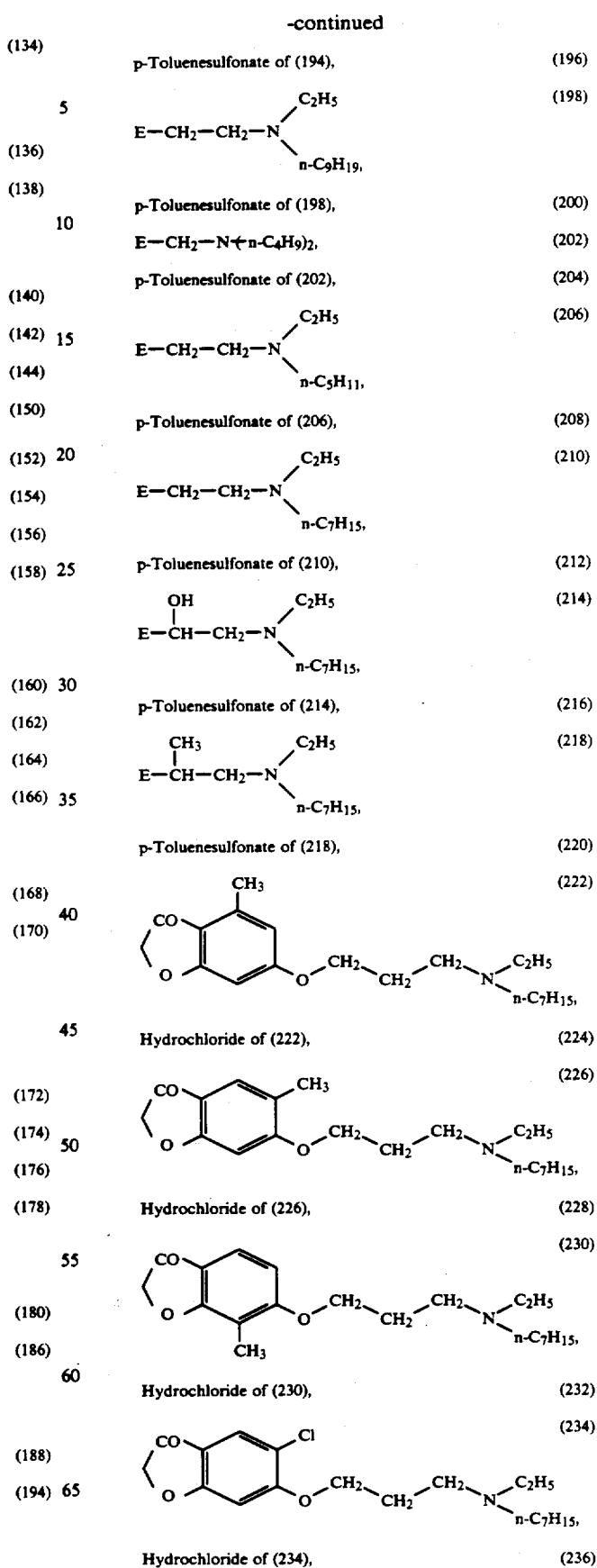

Hydrochloride of (222), (224)

(226)

Hydrochloride of (226), (228)

(230)

Hydrochloride of (230), (232)

(234)

Hydrochloride of (234), (236)

-continued

[Structure with OCH₃, dioxole-fused cyclohexene, OCH₂CH₂CH₂N(C₂H₅)(n-C₇H₁₅)] (238)

p-Toluenesulfonate of (238), (240)

[Structure with dioxole-fused cyclohexene, OCH₃, OCH₂CH₂CH₂N(C₂H₅)(n-C₇H₁₅)] (242)

Hydrochloride of (242), (244)

[Structure CH₃-substituted dioxole-fused cyclohexene with OCH₂CH₂CH₂N(C₂H₅)(n-C₇H₁₅)] (246)

Hydrochloride of (246), (248)

[Structure dioxole-fused cyclohexene with OCH₂CH₂CH₂N(C₂H₅)(n-C₇H₁₅)] (250)

p-Toluenesulfonate of (250), (252)

$$E-CH_2CH_2N\begin{matrix}CH_2-CH\begin{matrix}CH_3\\C_2H_5\end{matrix}\\CH_2-CH\begin{matrix}C_2H_5\\C_2H_5\end{matrix}\end{matrix}$$ (253)

Hydrochloride of (254), (253)'

$E-CH_2CH_2-NH-t-C_4H_9$, (254)

Hydrochloride of (254), (254)'

$E-CH_2CH_2-N(n-C_7H_{15})_2$, (255)

$E-CH_2CH_2-N\begin{matrix}CH_3\\CH_2CH_2-\text{Ph}\end{matrix}$ (256)

Hydrochloride of (256), (256)'

$E-CH_2CH_2-NH-O-\text{Cyclohexyl}$, (257)

Hydrochloride of (257), (257)'

[Structure with dioxole-fused cyclohexene, OCH₂CH₂CH₂N(C₂H₅)(C₇H₁₅)] (258)

p-Toluenesulfonate of (258), (258)'

$E-CH_2CH_2NH-iso-C_3H_7$, (259)

Hydrochloride of (259), (259)'

$E-CH_2CH_2-N\begin{matrix}iso-C_3H_7\\n-C_5H_{11}\end{matrix}$ (260)

Hydrochloride of (260), (260)'

$E-CH_2CH_2-N\begin{matrix}iso-C_3H_7\\n-C_6H_{13}\end{matrix}$ (261)

Hydrochloride of (261), (261)'

$E-CH_2CH_2-N\begin{matrix}iso-C_3H_7\\n-C_7H_{15}\end{matrix}$ (262)

Hydrochloride of (262), (262)'

$E-CH_2-NH-iso-C_3H_7$, (263)

Hydrochloride of (263), (263)'

$E-CH_2-NH(iso-C_3H_7)_2$, (264)

Hydrochloride of (264), (264)'

$E(CH_2)_2N(n-C_4H_9)_2$, (265)

p-Toluenesulfonate of (265), (265)'

$E(CH_2)_3N(n-C_4H_9)_2$, (266)

p-Toluenesulfonate of (266), (266)'

$E(CH_2)_2NHCH_3$, (267)

Hydrobromide of (267), (267)'

$E(CH_2)_2NH-\text{Ph}$, (269)

Hydrochloride of (269), (269)'

$E(CH_2)_2N\begin{matrix}CH_3\\\text{Ph}\end{matrix}$ (270)

Hydrochloride of (270), (270)'

$E(CH_2)_2N\begin{matrix}CH_3\\|\\C=N-CN\\|\\SCH_3\end{matrix}$ (271)

-continued

| | |
|---|---|
| Hydrochloride of (271), | (271)' |
| E—CHCH₂NH-iso-C₃H₇,<br>     |<br>     OH | (272) |
| p-Toluenesulfonate of (272), | (272)' |
| E—CHCH₂NH-tert-C₄H₉,<br>     |<br>     OH | (273) |
| p-Toluenesulfonate of (273), | (273)' |
| E—CHCH₂—N(n-C₄H₉)₂,<br>     |<br>     OH | (274) |
| Hydrochloride of (274), | (274)' |
| E(CH₂)₂N(CH₃)—CH₂CH(OH)—C₆H₄—NHSO₂CH₃, | (284) |
| p-Toluenesulfonate of (284), | (284)' |
| E(CH₂)₂N(CH₃)—CH₂CO—C₆H₄—NHSO₂CH₃, | (285) |
| p-Toluenesulfonate of (285), | (285)' | wherein E represents the moiety of the following structure

[structure: methylenedioxyphenyl-CH₂—O—]

12. An amine compound according to claim 1 wherein A and B, taken together, represent a group of formula —CR¹³R¹⁴—CR¹⁵R¹⁶—O— and said compound is selected from the group consisting of (400) [2,3-dihydrobenzofuran-5-yl—O—CH₂—CH₂—CH₂—N(C₂H₅)(n-C₇H₁₅)]

(402) Hydrochloride of (400)

(404) [3-(tert-pentyl)-4-(O—CH₂—CH₂—CH₂—N(C₂H₅)(n-C₇H₁₅))phenyl structure]

13. An amine compound according to claim 1 having the formula

[structure with OH, phenyl, —O—CH₂—CH₂—CH₂—N(C₂H₅)(n-C₇H₁₅)]

14. A pharmaceutical composition comprising an effective amount of the compound of claim 2 as an active ingredient and a pharmaceutically acceptable carrier.

15. A method for treatment of arrythmia in a patient in need thereof, comprising administering to said patient a pharmacologically effective amount of the compound of claim 2 as an active ingredient.

16. A method for treating psychoneurological diseases and psychoneurological diseases in a patient in need thereof, comprising administering to said patient a psychoneurologically effective amount of the compound of claim 2 as an active ingredient.

* * * * *

UNITED STATES PATENT AND TRADEMARK OFFICE
CERTIFICATE OF CORRECTION

PATENT NO. : 5,192,799
DATED : March 9, 1993
INVENTOR(S) : Ikuo Tomino, et. al.

It is certified that error appears in the above-indentified patent and that said Letters Patent is hereby corrected as shown below:

On the Title page, item [73], Assignee: should read --after "Mitsui Petrochemical Industries, Ltd." insert --Mitsui Pharmaceuticals, Inc.--

Signed and Sealed this

Eleventh Day of October, 1994

Attest:

BRUCE LEHMAN

Attesting Officer

Commissioner of Patents and Trademarks